US011648317B2

(12) United States Patent
Patel et al.

(10) Patent No.: US 11,648,317 B2
(45) Date of Patent: May 16, 2023

(54) STABLE ANTI-CD79B IMMUNOCONJUGATE FORMULATIONS

(71) Applicant: Genentech, Inc., South San Francisco, CA (US)

(72) Inventors: Ankit R. Patel, Foster City, CA (US); Jun Liu, Pacifica, CA (US)

(73) Assignee: Genentech, Inc., South San Francisco, CA (US)

( * ) Notice: Subject to any disclaimer, the term of this patent is extended or adjusted under 35 U.S.C. 154(b) by 927 days.

(21) Appl. No.: 16/383,478

(22) Filed: Apr. 12, 2019

(65) Prior Publication Data

US 2019/0314517 A1 Oct. 17, 2019

Related U.S. Application Data

(60) Provisional application No. 62/657,185, filed on Apr. 13, 2018.

(51) Int. Cl.

| A61K 39/395 | (2006.01) |
|---|---|
| A61K 47/68 | (2017.01) |
| A61J 1/10 | (2006.01) |
| A61K 47/22 | (2006.01) |
| A61K 47/26 | (2006.01) |
| A61K 47/34 | (2017.01) |
| A61K 47/10 | (2017.01) |
| A61K 47/02 | (2006.01) |
| A61K 47/54 | (2017.01) |
| A61K 38/08 | (2019.01) |
| C07K 16/28 | (2006.01) |
| A61K 47/14 | (2017.01) |

(52) U.S. Cl.
CPC ........... *A61K 47/6811* (2017.08); *A61J 1/10* (2013.01); *A61K 38/08* (2013.01); *A61K 47/02* (2013.01); *A61K 47/10* (2013.01); *A61K 47/14* (2013.01); *A61K 47/22* (2013.01); *A61K 47/26* (2013.01); *A61K 47/34* (2013.01); *A61K 47/542* (2017.08); *A61K 47/6873* (2017.08); *C07K 16/2803* (2013.01); *C07K 2317/24* (2013.01); *C07K 2317/56* (2013.01)

(58) Field of Classification Search
None
See application file for complete search history.

(56) References Cited

U.S. PATENT DOCUMENTS

| 4,816,567 A | 3/1989 | Cabilly |
|---|---|---|
| 4,933,294 A | 6/1990 | Waterfield |
| 5,362,852 A | 11/1994 | Geoghegan |
| 5,401,638 A | 3/1995 | Carney |
| 5,500,362 A | 3/1996 | Robinson |
| 5,591,828 A | 1/1997 | Bosslet |
| 5,635,483 A | 6/1997 | Pettit |
| 5,641,870 A | 6/1997 | Rinderknecht |
| 5,663,149 A | 9/1997 | Pettit |
| 5,780,588 A | 7/1998 | Pettit |
| 5,821,337 A | 10/1998 | Carter |
| 6,075,181 A | 6/2000 | Kucherlapati |
| 6,150,584 A | 11/2000 | Kucherlapati |
| 6,194,551 B1 | 2/2001 | Idusogie |
| 8,088,378 B2 | 1/2012 | Chen |
| 8,088,387 B2 | 1/2012 | Steeves |
| 8,545,850 B2 | 10/2013 | Chen |
| 8,722,857 B2 | 5/2014 | Chen |
| 9,896,506 B2 | 2/2018 | Chen |
| 2005/0238649 A1 | 10/2005 | Doronina |
| 2007/0031402 A1* | 2/2007 | Zhang ................ A61K 47/6849 424/178.1 |
| 2009/0028856 A1 | 1/2009 | Chen |
| 2010/0215669 A1 | 8/2010 | Chen |
| 2011/0135667 A1 | 6/2011 | Chen |
| 2014/0099260 A1 | 4/2014 | Chen |
| 2014/0335107 A1 | 11/2014 | Chen |
| 2015/0314016 A1 | 11/2015 | Chen |
| 2017/0058032 A1 | 3/2017 | Chen |

FOREIGN PATENT DOCUMENTS

| EP | 0404097 B1 | 9/1996 |
|---|---|---|
| EP | 0616812 B1 | 11/1999 |
| EP | 0600517 B1 | 8/2000 |
| WO | WO199105264 A1 | 4/1991 |
| WO | WO199311161 A1 | 6/1993 |
| WO | WO199411026 A2 | 5/1994 |
| WO | WO199411026 A3 | 8/1994 |
| WO | 199704801 A1 | 2/1997 |
| WO | WO199845479 A1 | 10/1998 |
| WO | WO199951642 A1 | 10/1999 |
| WO | WO200042072 A2 | 7/2000 |
| WO | WO200042072 A3 | 11/2000 |
| WO | WO2002088172 A2 | 11/2002 |

(Continued)

OTHER PUBLICATIONS

Adem, Y.T. et al. (Feb. 24, 2014). "Auristatin Antibody Drug Conjugate Physical Instability And The Role Of Drug Payload," Bioconjugate Chemistry 25:656-664.

Alley, S. et al. (2004). "Controlling The Location Of Drug Attachment In Antibody-Drug Conjugates," Proceedings of the AACR, vol. 45, Abstract # 627, 1 page.

Barbas, C.F. et al. (Apr. 1994). "In vitro Evolution of a Neutralizing Human Antibody to Human Immunodeficiency Virus Type 1 to Enhance Affinity and Broaden Strain Cross-Reactivity," Proc. Nat. Acad. Sci. USA 91:3809-3813.

Bardin, C. et al. (2011). "Guidelines for the Practical Stability Studies of Anticancer Drugs: A European Consensus Conference," Annales Pharmaceutiques Francaises 69:221-231.

(Continued)

*Primary Examiner* — Yunsoo Kim
(74) *Attorney, Agent, or Firm* — Morrison & Foerster LLP

(57) ABSTRACT

The disclosure provides stable pharmaceutical compositions comprising an anti-CD79b immunoconjugate and a surfactant. The disclosure also provides methods for using such compositions for the treatment of cancer.

32 Claims, 20 Drawing Sheets

Specification includes a Sequence Listing.

(56) References Cited

FOREIGN PATENT DOCUMENTS

| WO | WO2002088172 A3 | 2/2003 |
|---|---|---|
| WO | WO2009012268 A1 | 1/2009 |
| WO | WO2009099728 A1 | 8/2009 |
| WO | WO2010081004 A1 | 7/2010 |
| WO | WO2014011521 A1 | 1/2014 |
| WO | WO2014177615 A3 | 12/2014 |
| WO | 2015164581 A1 | 10/2015 |
| WO | WO2016049214 A1 | 3/2016 |
| WO | 2015164581 A8 | 10/2016 |

OTHER PUBLICATIONS

Beckley, N. et al. (Sep. 12, 2013). "Investigation Into Temperature-Induced Aggregation of an Antibody Drug Conjugate," Bioconjugate Chemistry. 24:1674-1683.
Boerner, P. et al. (Jul. 1, 1991). "Production of Antigen-Specific Human Monoclonal Antibodies From in Vitro-Primed Human Splenocytes," J. Immunol. 147(1):86-95.
Borrebaeck, C.A.K. (1995). "Strategies for Humanizing Antibodies," in Antibody Engineering 2nd Ed. pp. 179-181.
Capel, P.J.A. et al. (1994). "Heterogeneity of Human IgG Fc Receptors," Immunomethods 4:25-34.
CAS Registration No. 1313206-42-6—"Polatuzumab Vedotin," retrieved from https://chem.nlm.nih.gov/chemidplus/m/1313206-42-6, last visited May 31, 2019, 2 pages.
Chen, Y. et al. (1999). "Selection and Analysis of An Optimized Anti-VEGF Antibody: Crystal Structure of an Affinity-Matured Fab in Complex with Antigen," J. Mol. Biol. 293:865-881.
Chothia, C. et al. (Aug. 20, 1987). "Canonical Structures for the Hypervariable Regions of Immunoglobulins," J. Mol. Biol. 196(4):901-917.
Clackson, T. et al. (Aug. 15, 1991). "Making Antibody Fragments Using Phage Display Libraries," Nature 352:624-628.
Cleland, J.L. et al. (1993). "The Development of Stable Protein Formulations: A Close Look at Protein Aggregation, Deamidation, and Oxidation," Critical Reviews In Therapeutic Drug Carrier Systems 10(4):307-377.
Clynes, R. et al. (Jan. 1998). "Fc Receptors Are Required in Passive and Active Immunity to Melanoma," Proc. Natl. Acad. Sci. USA 95:652-656.
Cole, S.P.C. et al. (1985). "The EBV-Hybridoma Technique and Its Applicaton to Human Lung Cancer," in Monoclonal Antibodies and Cancer Therapy, Alan R. Liss, p. 77-96.
Daeron, M. (1997). "Fc Receptor Biology," Annu. Rev. Immunol. 15:203-234.
DCDS4501A—"A Study of Polatuzumab Vedotin (DCDS4501A) in Combination With Rituzimab or Obinutuzumab Plus Bendamustine in Participants With Relapsed or Refractory Follicular of Diffuse Larg B-Cell Lymphoma," retrieved from https://clincialtrials.gov/ct2/show/NCT02257567, last visited May 31, 2019.
De Haas, M. et al. (Oct. 1995). "Fcγ Receptors of Phagocytes," J. Lab. Clin. Med. 126:330-341.
Donbrow, M. et al. (Dec. 1978). "Autoxidation of Polysorbates," Journal of Pharmaceutical Sciences 67 (12):1676-1681.
Doronina, S.O. et al. (Jul. 2003). "Development of Potent Monoclonal Antibody Auristatin Conjugates for Cancer Therapy," Nat. Biotechnol. 21(7):778-784.
Fischer, S. et al. (2008, e-pub. Apr. 30, 2008). "Glycation During Storage and Administration of Monoclonal Antibody Formulations," European J. Pharma. and Biopharm. 70:42-50.
Gazzano-Santoro, H. et al. (1996). "A Non-Radioactive Complement-Dependent Cytotoxicity Assay for Anti-CD20 Monoclonal Antibody," J. Immunol. Methods 202:163-171.
Geoghegan, K. F. et al. (1992). "Site-Directed Conjugation of Nonpeptide Groups to Peptides and Proteins via Periodate Oxidation of a 2-Amino Alcohol. Application to Modification at N-Terminal Serine," Bioconjugate Chem. 3(2): 138-146.

Guyer, R.L. et al. (Aug. 1976). "Immunoglobulin Binding By Mouse Intestinal Epithelial Cell Receptors," J. Immunol. 117(2):587-593.
Hamann, P.R. et al. (2005). "Monoclonal Antibody-Drug Conjugates," Expert Opin. Ther. Patents 15:1087-1103.
Hamblett, K.J. et al. (Oct. 15, 2004). "Effects of Drug Loading on the Antitumor Activity of a Monoclonal Antibody Drug Conjugate," Clin. Cancer Res. 10:7063-7070.
Hamblett, K.J. et al. (Mar. 2004). "Effect of Drug Loading on the Pharmacology, Pharmacokinetics, and Toxicity of an Anti-CD30 Antibody-Drug Conjugate," Proceedings of the AACR, vol. 45, Abstract # 624, 2 pages.
Harris, W.J. (1995). "Therapeutic Monoclonal. Production of Humanized Monoclonal Antibodies for In Vivo Imaging and Therapy," Biochem. Soc. Transactions 23:1035-1038.
Hawkins, R.E. et al. (1992). "Selection of Phage Antibodies by Binding Affinity: Mimicking Affinity Maturations," J. Mol. Biol. 226:889-896.
Holliger, P. et al. (Jul. 1993). "'Diabodies': Small Bivalent and Bispecific Antibody Fragments," Proc. Natl. Acad. Sci. USA 90:6444-6448.
Hoogenboom, H.R. et al. (1992). "By-Passing Immunisation. Human Antibodies From Synthetic Repertoires of Germline VH Gene Segments Rearranged in Vitro," J. Mol. Biol. 227:381-388.
Hudson, P.J. et al. (Jan. 2003). "Engineered Antibodies," Nat. Med. 9(1):129-134.
Hurle, M.R. et al. (1994). "Protein Engineering Techniques for Antibody Humanization," Curr. Op. Biotech. 5:428-433.
Idusogie, E.E. et al. (2000). "Mapping of the C1q Binding Site on Rituxan, a Chimeric Antibody With a Human IgG1 Fc," J. Imrmmol. 164:4178-4184.
International Search Report and Written Opinion, dated Jun. 24, 2019, for PCT Application No. PCT/US2019/027329, filed Apr. 12, 2019, 14 pages.
IUPHAR/BPS No. 8404—"Polatuzumab Vedotin,", retrieved from http://www.guidetopharmacology.or/GRAC/Ligand-DisplayForwardJligandid=8404, last visited May 31, 2019, 1 page.
Jackson, J.R. et al. (1995). "In Vitro Antibody Maturation," J. Immunol. 154(7):3310-3319.
Jones, A.J.S. (1993). "Analysis of Polypeptides and Proteins," Adv. Drug Delivery Rev. 10:29-90.
Jones, P.T. et al. (May 29, 1986). "Replacing the Complementarity-Determing Regions in a Human Antibody With Those From a Mouse," Nature 321:522-525.
Kabat, E.A. et al. (1991). Sequences of Proteins of Immunological Interest, 5th ed., Public Health Service, National Institutes of Health, Bethesda, MD. TOC, 21 pages.
KEGG No. D10761—"Drug Polatuzumab Vedotin," retrieved from https://www.kegg.jp/entry/D10761, last visited May 31, 2019, 1 page.
Kerwin, B.A. (Aug. 2008). "Polysorbates 20 and 80 Used In The Formulation Of Protein Biotherapeutics: Structure and Degradation Pathways," Journal of Pharmaceutical Sciences 97(8):2924-2935.
Kim, J-K. et al. (1994). "Localization of the Site of the Murine IgGI Molecule That is Involved in Binding to the Murine Intestinal Fc Receptor," Eur. J. Immunol. 24:2429-2434.
Köhler, G. et al. (Aug. 7, 1975). "Continuous Culture of Fused Cells Secreting Antibody of Predefined Specificity," Nature, 256:495-497.
Lam, X, et al. (2011). "Site-Specific Tryptophan Oxidation Induced by Autocatalytic Reaction of Polysorbate 20 in Protein Formulation," Pharm Res. 28:2543-2555.
Lam, X.M. et al. (Nov. 1997). "Antioxidants For Prevention Of Methionine Oxidation In Recombinant Monoclonal Antibody HER2," Journal of Pharmaceutical Sciences 86(11):1250-1255.
Li, J. et al. (Mar. 7, 2006). Human Antibodies for Immunotherapy Development Generated Via a Human B Cell Hybridoma Technology, Proc. Natl. Acad. Sci. USA 103(10):3557-3562.
Lyon, R. et al. (Apr. 2013) Self-Stabilizing ADCs: Conjugates Prepared with Maleimido Drug-Linkers That Catalyze their own Thiosuccinimide Ring Hydrolysis., Abstract No. 4333, American Association for Cancer Research. Abstract Only.

(56) References Cited

OTHER PUBLICATIONS

Marks, J.D. et al. (1991). "By-Passing Immunization. Human Antibodies From V-Gene Libraries Displayed on Phage," J. Mol. Biol. 222:581-597.

Marks, J.D. et al. (Jul. 1992). "By-Passing Immunization: Building High Affinity Human Antibodies by Chain Shuffling," Bio/Technology 10: 779-783.

Mason, B. et al. (Mar. 2010, e-pub. Feb. 2, 2010). "Oxidation of Free L-Histidine By tert-Butylhydroperoxide," Pharma. Res. 27(3):447-456.

McDonagh, C.F. et al. (2006, e-pub. Apr. 27, 2006). "Engineered Antibody-Drug Conjugates With Defined Sites and Stoichiometries of Drug Attachment," Prot. Engr. Design & Selection 19(7):299-307.

Morrison, S.L. et al. (Nov. 1984). "Chimeric Human Antibody Molecules: Mouse Antigen-Binding Domains With Human Constant Region Domains," Proc. Natl. Acad. Sci. USA 81:6851-6855.

Pettit, R.K. et al. (Nov. 1998). "Specific Activities of Dolastatin 10 and Peptide Derivatives Against Cryptococcus neoformans," Antimicrobial Agents and Chemotherapy 42(11):2961-2965.

Plückthun, A. (1994). "Antibodies from *Escherichia coli*," in Chapter 11 The Pharmacology of Monoclonal Antibodies, vol. 113, Rosenburg and Moore eds., SpringerVeriag, New York, pp. 269-315.

Presta, L.G. (1992). "Antibody Engineering," Current Opinion in Structural Biology, 2:593-596.

Presta, L.G. et al. (Oct. 15, 1997). "Humanization of an Anti-Vascular Endothelial Growth Factor Monoclonal Antibody for the Therapy of Solid Tumors and Other Disorders," Cancer Res. 57:4593-4599.

Ravetch, J.V. et al. (1991). "Fc Receptors," Annu. Rev. Immunol. 9:457-492.

RG7596—"Polatuzumab Vedotin," retrieved from https://en.wikipedia.org/wiki/Polatuzumab_vedotin, last visited May 31, 2019, 2 pages.

Riechmann, L. et al. (1988). "Reshaping Human Antibodies for Therapy," Nature 332:323-329.

Schier, R. et al. (1995). "Identification of Functional and Structural Amino-Acid Residues by Parsimonious Mutagenesis," Gene 169:147-155.

Shieh, I. et al. (Sep. 8, 2015, e-pub. Aug. 5, 2015). "Predicting the Agitation-Induced Aggregation of Monoclonal Antibodies Using Surface Tensiometry," Mol. Pharm. 12:3184-3193.

Shields, R.L. et al. (Mar. 2, 2001). "High Resolution Mapping of the Binding Site of Human IgG1 for FcγRI, FcγRII, FcγIII, and Fc Rn and Design of IgG1 Variants With Improved Binding to the FcγR," J. Biol. Chem. 9(2):6591-6604.

Shire, S. (Apr. 23, 2015). Monoclonal Antibodies: Meeting the Challenges in Manufacturing, Formulation, Delivery and Stability of Final Drug Product Woodhead Publishing, 1st Ed. pp. 93-117.

Sias, P.E. et al. (1990). "ELISA for Quantitation of the Extracellular Domain of p185HER2 in Biological Fluids," J. Immunol. Methods 132:73-80.

Sreedhara, A. et al. (Jan. 2012, e-pub. Sep. 8, 2011). "Stability of IgG1 Monoclonal Antibodies in Intravenous Infusion Bags Under Clinical In-Use Conditions," J. Pharm. Sci. 101(1):21-30.

Van Dijk, M.A. et al. (2001). "Human Antibodies as Next Generation Therapeutics," Curr. Opin. Pharmacol 5:368-374.

Vaswani, S.K. et al. (Aug. 1998). "Humanized Antibodies as Potential Therapeutic Drugs," Ann. Allergy, Asthma and Immunol. 81:105-115.

Vitetta, E.S. et al. (Nov. 20, 1987). "Redesigning Nature's Poisons to Create Anti-tumor Reagents," Science 238:1098-1104.

Woyke, T. et al. (Dec. 2001). "In Vitro Activities and Postantifungal Effects of the Potent Dolastatin 10 Derivative Auristatin PHE," Antimicrob. Agents and Chemother. 45(12):3580-3584.

Yelton, D.E. et al. (1995). "Affinity Maturation of the BR96 Anti-Carcinoma Antibody by Codon-Based Mutagenesis," J. Immunol. 155:1994-2004.

Zapata, G. et al. (1995). "Engineering Linear F(ab')2 Fragments for Efficient Production in *Escherichia coli* and Enhanced Antiproliferative Activity," Protein Eng. 8(10):1057-1062.

International Preliminary Report on Patentability, dated Oct. 13, 2020, for PCT Application No. PCT/US2019/027329, filed Apr. 12, 2019, 6 pages.

Palanca-Wessels, M.C.A.. et al. (2015, e-pub. Apr. 27, 2015). "Safety and Activity of the Anti-CD79B Antibody-Drug Conjugated Polotuzumab Vedotin in Relapsed or Refractory B-Cell Non-Hodgkin Lymphoma and Chronic Lymphocytic Leukaemia: A Phase 1 Study," The Lancet 16:704-715.

Shah, S.A. (Sep. 1, 2017). "Deep Insights—Antibody-Drug Conjugates for the Treatment of Hematological Malignancy," Atlas of Genetics and Cytogenetics in Oncology and Haematology, 22 pages.

Jorgensen, L. et al. (2009, e-pub. Aug. 13, 2009). "Recent Trends In Stabilising Peptides and Proteins In Pharmaceutical Formulation—Considerations In The Choice Of Excipients," Expert Opinion on Drug Delivery 6(11):1219-1230.

Tyagi, R. et al. (1998). "Chemical Modification and Chemical Crosslinking for Proteins/Enzymes Stabilization," Biochemistry (Mosc.) 63(3):395-407.

Wang, W. et al. (Jan. 2007). "Antibody Structure, Instability, and Formulation," Journal of Pharmaceutical Science 96(1):1-26.

\* cited by examiner

FIG. 15A — 10 mg/mL 260mM sucrose Moisture ~2.4%
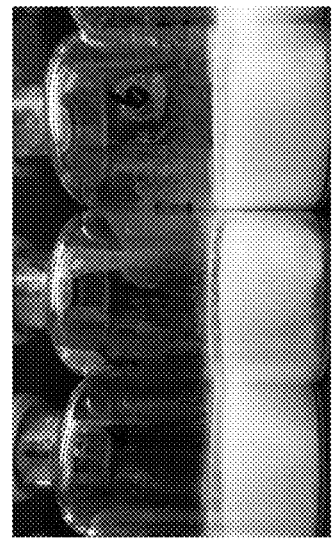
FIG. 15B — 10 mg/mL 180 mM sucrose Moisture ~1.9%
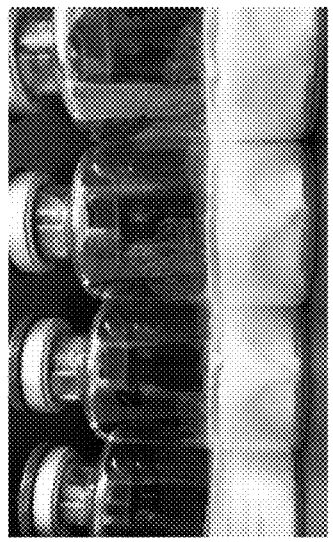
FIG. 15C — 10 mg/mL 120mM sucrose Moisture ~1.5%

STABLE ANTI-CD79B IMMUNOCONJUGATE FORMULATIONS

CROSS REFERENCE TO RELATED APPLICATIONS

This application claims the benefit of U.S. Provisional Application Ser. No. 62/657,185, filed Apr. 13, 2018, which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392044300SEQLIST.TXT, date recorded: Apr. 9, 2019, size: 12 KB).

FIELD

The present disclosure is directed to stable pharmaceutical compositions comprising an anti-CD79b immunoconjugate and a surfactant. The disclosure also provides methods for using such compositions for the treatment of cancer.

BACKGROUND

Intravenous (IV) administration using infusion bags is the most common route of delivery for biologics in the commercial setting. To support the delivery and compatibility of a biologic, such as an immunoconjugate, by IV administration, it is necessary to design a suitable therapeutic formulation that maintains stability after dilution in the infusion bag, during transportation, and throughout the course of administration (Bardin, C. et al. *Annales pharmaceutiques francaises* 69 (2011) 221-231).

One challenge of administering biologics, especially using IV infusion bags, is that the materials of construction and infusion solution can present a destabilizing environment for the therapeutic protein. Additionally, the protein also encounters interfacial stresses in the IV bag. Protein adsorption at the solid-liquid and air-water interfaces may cause protein denaturation at the surface, leading to protein aggregation (Shieh, I., et al. *Mol Pharm.* 12 (2015): 3184-93; Sreedhara, A., et al. *Pharm. Sci.* 101 (2012): 21-30). Further complicating IV administration, agitation of the infusion bags causes continuous regeneration of the air-liquid interface, resulting in repeated damage to the protein over time. Aggregation, caused by either the destabilizing solution conditions of the IV bag or by interfacial stress, can significantly and negatively impact the product quality, potency, and immunogenicity of a biologic.

The deleterious effects of IV administration on biologics can be mitigated, in part, through the use of surfactants in formulation development. Non-ionic surfactants, such as polysorbate-20 (PS20) or polysorbate-80 (PS80) are commonly used in protein formulations to protect and stabilize the molecule against air-water interfacial stress (Kerwin, B A. *J. Pharm. Sci.* 97 (2008) 2924-2935). Surfactants can protect the drug product (DP) against surface-induced damage by competing with the protein at both air-water and solid-water interfaces (Kerwin, B A. *J. Pharm. Sci.* 97 (2008) 2924-2935). In addition, surfactants also reduce the surface tension of the system (Cleland, J L., et al. *Critical reviews in therapeutic drug carrier systems* 10 (1993) 307-377). However, a critical drawback in using a non-ionic surfactant at a concentration suitable for IV bag delivery is that prolonged exposure of a biologic to the surfactant can lead to oxidation of specific amino acid residues, thereby reducing therapeutic potency. Lam X, et al., *Pharm Res.* (2011) 28:2543-2555.

Importantly, prior to IV administration, biologics must also possess a long, stable shelf-life under storage conditions without comprising the structure and activity of the therapeutic protein. Liquid formulations of antibody-drug conjugates (ADCs) employing a linker, for example, may be susceptible to acid-catalyzed hydrolysis of the linker during storage. Such instability can cause premature release of the drug compound upon IV administration to a patient, negatively affecting the pharmacokinetics and safety of the biologic.

Thus, there is a need for the development of a stable pharmaceutical composition that is both stable for IV administration and possesses a long shelf life under storage conditions. The present disclosure fulfills this need and offers other related advantages.

BRIEF SUMMARY

In one aspect, the disclosure provides a pharmaceutical composition including an anti-CD79b immunoconjugate and a surfactant, wherein the surfactant is at a concentration of at least 0.06% w/v (i.e., 0.6 mg/ml) and wherein the anti-CD79b immunoconjugate comprises the formula:

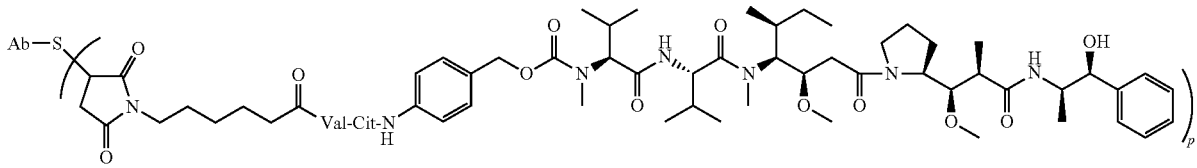

wherein:
Ab is an anti-CD79b antibody, wherein the anti-CD79b antibody comprises a heavy chain and a light chain, wherein the light chain comprises (a) an HVR-L1 sequence of KASQSVDYEGDSFLN (SEQ ID NO: 1); (b) an HVR-L2 sequence of AASNLES (SEQ ID NO: 2); and (c) an HVR-L3 sequence of QQSNEDPLT (SEQ ID NO: 3); wherein the heavy chain comprises (a) an HVR-H1 sequence of GYTFSSYWIE (SEQ ID NO: 4); (b) an HVR-H2 sequence of GEILPGGGDTNYNEIFKG (SEQ ID NO: 5); and (c) an HVR-H3 sequence of TRRVPIRLDY (SEQ ID NO: 6); Val is valine; Cit is citrulline; and p is a value from about 1 to about 8 (e.g., between about 2 and about 5, such as about 3.5).

In some embodiments, the anti-CD79b immunoconjugate is at a concentration of about 5 mg/ml to about 60 mg/ml, about 10 mg/ml to about 50 mg/ml, about 10 mg/ml to about 40 mg/ml, about 10 mg/ml to about 30 mg/ml, or about 10 mg/ml to about 20 mg/ml.

In some embodiments, the anti-CD79b immunoconjugate is at a concentration of about 10 mg/ml to about 20 mg/ml. In one embodiment, the anti-CD79b immunoconjugate is at a concentration of about 10 mg/ml. In another embodiment, the anti-CD79b immunoconjugate is at a concentration of about 20 mg/ml.

In some embodiments, the anti-CD79b immunoconjugate is at a concentration of 5 mg/ml to 60 mg/ml, 10 mg/ml to 50 mg/ml, 10 mg/ml to 40 mg/ml, 10 mg/ml to 30 mg/ml, or 10 mg/ml to 20 mg/ml.

In some embodiments, the anti-CD79b immunoconjugate is at a concentration of 10 mg/ml to 20 mg/ml. In one embodiment, the anti-CD79b immunoconjugate is at a concentration of 10 mg/ml. In another embodiment, the anti-CD79b immunoconjugate is at a concentration of 20 mg/ml.

In some embodiments, the surfactant is at a concentration of between about 0.06% w/v (i.e., 0.6 mg/ml) and about 0.12% w/v (i.e., 1.2 mg/ml). In some embodiments, the surfactant is at a concentration of at least about 0.06% w/v (i.e., 0.6 mg/ml). In another embodiment, the surfactant is at a concentration of at least about 0.12% w/v (i.e., 1.2 mg/ml). In some embodiments, the surfactant is at a concentration of at least 0.06% w/v. In another embodiment, the surfactant is at a concentration of at least 0.12% w/v. In some embodiments, the surfactant is at a concentration of 0.06% w/v. In another embodiment, the surfactant is at a concentration of 0.12% w/v.

In some embodiments, the anti-CD79b immunoconjugate is at a concentration of about 10 mg/ml and the surfactant is at a concentration of about 0.06% w/v (i.e., 0.6 mg/ml). In some embodiments, the anti-CD79b immunoconjugate is at a concentration of about 20 mg/ml and the surfactant is at a concentration of at least about 0.12% w/v. In some embodiments, the anti-CD79b immunoconjugate is at a concentration of about 20 mg/ml and the surfactant is at a concentration of about 0.12% w/v (i.e., 1.2 mg/ml).

In some embodiments, the anti-CD79b immunoconjugate is at a concentration of 10 mg/ml and the surfactant is at a concentration of 0.06% w/v (i.e., 0.6 mg/ml). In some embodiments, the anti-CD79b immunoconjugate is at a concentration of 20 mg/ml and the surfactant is at a concentration of at least 0.12% w/v. In some embodiments, the anti-CD79b immunoconjugate is at a concentration of 20 mg/ml and the surfactant is at a concentration of 0.12% w/v.

In some embodiments according to (or as applied to) any of the embodiments above, the pharmaceutical composition is a liquid pharmaceutical composition. In some embodiments, the liquid pharmaceutical composition is stable for at least about any one of 4, 6, 8, 10, 12, 14, 16, 18, 20, 22, 24 hours upon storage at 30° C., or for at least about any one of 24, 48, or 72 hours upon storage at 2° C.-8° C.

In certain embodiments of the present disclosure, the surfactant herein is non-ionic. In an exemplary embodiment, the surfactant is chosen from the group consisting of polysorbate 20 (PS20), polysorbate 80 (PS80), poloxamer 188 (P188), N-octyl-β-D glucopyranoside (OG), and a combination thereof. In a specific embodiment, the surfactant is PS20. In still another specific embodiment, the surfactant is PS80.

In some embodiments of the present disclosure, the composition further includes a buffering agent. In certain embodiments, buffering agent is a histidine buffer. In some embodiments, the buffering agent is a succinate buffer. In a specific embodiment, the succinate buffer is a sodium succinate buffer. In some embodiments, the sodium succinate buffer is at a concentration of about 10 mM to about 200 mM. In some embodiments, the sodium succinate buffer is at a concentration of 10 mM to 200 mM. In one embodiment, the sodium succinate buffer is at a concentration of about 10 mM. In another embodiment, the sodium succinate buffer is at a concentration of 10 mM.

In some embodiments, the composition of the present disclosure has a pH from about 5.0 to about 6.0. In specific embodiments, the buffer has a pH of about 5.0, about 5.1, about 5.2, about 5.3, about 5.4, about 5.5, about 5.6, about 5.7, about 5.8, about 5.9, or about 6.0. In one embodiment, the composition of the present disclosure has a pH of about 5.3. In some embodiments, the composition of the present disclosure has a pH from 5.0 to 6.0. In specific embodiments, the buffer has a pH of 5.0, 5.1, 5.2, 5.3, 5.4, 5.5, 5.6, 5.7, 5.8, 5.9, or 6.0. In one embodiment, the composition of the present disclosure has a pH of 5.3.

In certain embodiments of the present disclosure, the composition further includes a sugar. In some embodiments, the sugar is at a concentration of about 100 mM to about 260 mM. In some embodiments, the sugar is at a concentration of 100 mM to 260 mM. In some embodiments, the sugar is selected from the group consisting of: sucrose, mannitol, sorbitol, glycerol, dextran 40, and trehalose.

In a specific embodiment, the sugar is sucrose. In one embodiment of the present disclosure, sucrose is at a concentration of about 120 mM. In another embodiment, sucrose is at a concentration of 120 mM.

In some embodiments, the composition of the present disclosure is lyophilized (such as a lyophilized cake). In some embodiments, the lyophilized composition is contained in a vial, e.g., a 20-mil glass vial.

In one aspect, the present disclosure provides a pharmaceutical composition produced by lyophilization of a liquid formulation including 20 mg/ml of an anti-CD79b immunoconjugate in 10 mM sodium succinate buffer, 0.12% w/v of polysorbate 20, and 120 mM sucrose, wherein the liquid formulation has a pH of 5.3, and wherein the anti-CD79b immunoconjugate has the formula:

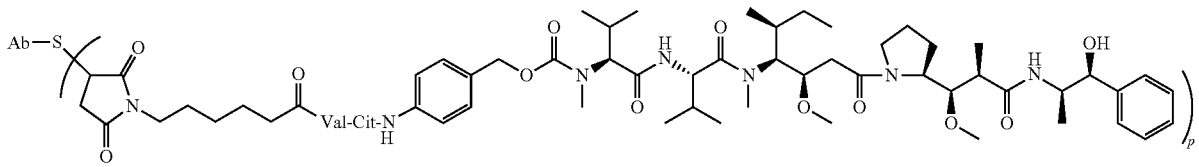

wherein:
Ab is an anti-CD79b antibody, wherein the anti-CD79b antibody comprises a heavy chain and a light chain, wherein the light chain comprises (a) an HVR-L1 sequence of KASQSVDYEGDSFLN (SEQ ID NO: 1); (b) an HVR-L2 sequence of AASNLES (SEQ ID NO: 2); and (c) an HVR-L3 sequence of QQSNEDPLT (SEQ ID NO: 3); wherein the heavy chain comprises (a) an HVR-H1 sequence of GYTFSSYWIE (SEQ ID NO: 4); (b) an HVR-H2 sequence of GEILPGGGDTNYNEIFKG (SEQ ID NO: 5); and (c) an HVR-H3 sequence of TRRVPIRLDY (SEQ ID NO: 6); Val is valine; Cit is citrulline; and p is a value from about 1 to about 8 (e.g., between about 2 and about 5, such as about 3.5).

In some embodiments of the present disclosure, the anti-CD79b antibody comprises a heavy chain variable domain (VH) comprising the amino acid sequence of SEQ ID NO: 7 and a light chain variable domain (VL) comprising the amino acid sequence of SEQ ID NO: 8. In some embodiments, the heavy chain comprises the amino acid sequence of SEQ ID NO: 9 and the light chain comprises the amino acid sequence of SEQ ID NO: 10.

Also provided is a pharmaceutical composition produced by lyophilization of a liquid formulation comprising 20 mg/ml of an anti-CD79b immunoconjugate in 10 mM sodium succinate buffer, 0.12% w/v of polysorbate 20, and 120 mM sucrose, wherein the liquid formulation has a pH of 5.3, and wherein the anti-CD79b immunoconjugate comprises the formula:

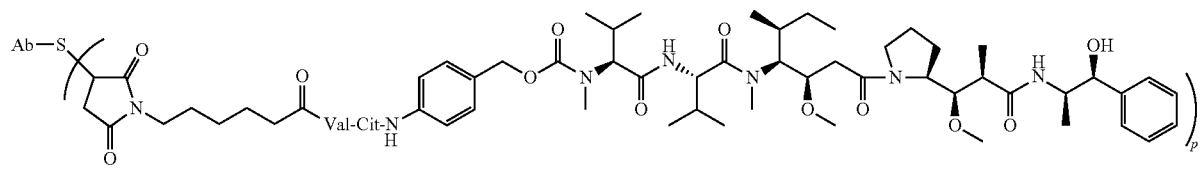

wherein Ab is an anti-CD79b antibody, wherein the anti-CD79b antibody comprises a heavy chain and a light chain, wherein the heavy chain comprises the amino acid sequence of SEQ ID NO: 9, the light chain comprises the amino acid sequence of SEQ ID NO: 10; Val is valine; Cit is citrulline; and p is a value from about 2 to about 5 (such as about 3.5). In some embodiments, the pharmaceutical composition is a lyophilized cake.

In certain embodiments, the pharmaceutical composition of the present disclosure has a stability of about 60 months at 5° C.±3° C. when protected from light. In certain embodiment, the pharmaceutical composition of the present disclosure has a stability of about 48 months at 5° C.±3° C. when protected from light.

In some embodiments, the stability of the pharmaceutical composition of the present disclosure is measured by size-exclusion chromatography high performance (SE-HPLC). In one embodiment, the composition has a main peak (area %) of at least 95.0 as measured by SE-HPLC.

In some embodiments, the stability of the pharmaceutical composition of the present disclosure is measured by imaged capillary isoelectric focusing (icIEF). In one embodiment, the composition has a main peak (area %) of at least 58.0, an acid region (area %) of at most 32.0, and a basic region (area %) of at most 12.0 as measured by icIEF.

In certain embodiments, the pharmaceutical composition of the present disclosure is reconstituted with sterile water for injection (SWFI). In some embodiments, the pharmaceutical composition is reconstituted in about 7.2 ml SWFI. In some embodiments, the reconstituted composition is stable for at least 4, 6, 8, 10, 12, 14, 16, 18, 20, 22, 24 hours upon storage at about 30° C. In some embodiments, the reconstituted composition is stable for at least 24, 48, or 72 hours upon storage at about 2° C. to about 8° C. In some embodiments, the reconstituted composition is further diluted into an isotonic buffer in an intravenous (IV) bag. In some embodiments, the final volume of the diluted composition in the IV bag is between about 50 ml and about 100 ml. In some embodiments, the concentration of the immunoconjugate in the IV bag is between about 0.72 mg and about 2.7 mg.

Also provided herein is a pharmaceutical composition produced by lyophilization of a liquid formulation comprising 20 mg/ml of an anti-CD79b immunoconjugate in 10 mM sodium succinate buffer, 0.12% w/v of polysorbate 20, and 120 mM sucrose, wherein the liquid formulation has a pH of 5.3, and wherein the anti-CD79b immunoconjugate comprises the formula:

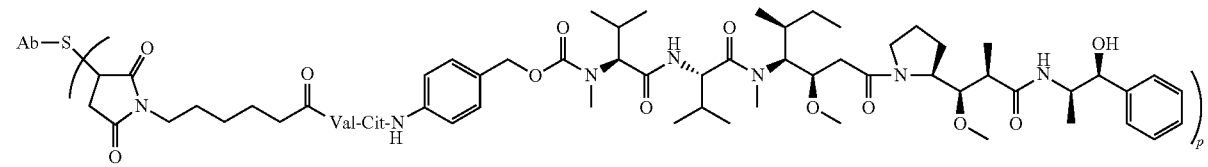

wherein Ab is an anti-CD79b antibody, wherein the anti-CD79b antibody comprises a heavy chain and a light chain, wherein the heavy chain comprises the amino acid sequence of SEQ ID NO: 9, the light chain comprises the amino acid sequence of SEQ ID NO: 10; Val is valine; Cit is citrulline; and p is a value from about 2 to about 5 (such as about 3.5).

Provided is a liquid composition (such as for intravenous administration) comprising a) between about 0.72 and about 2.7 mg/ml polatuzumab vedotin; b) between about 0.36 and about 1.35 mM sodium succinate; c) between about 0.51 and about 16.24 mM sucrose; d) between about 0.0432 and about 0.162 mg/ml polysorbate 20, wherein the pH of the liquid composition is between about 5 and about 5.7. Also provided is a liquid composition (such as for intravenous administration) comprising a) about 0.72 mg/ml polatuzumab vedotin; b) about 0.36 mM sodium succinate; c) about 0.51 mM sucrose; d) about 0.0432 mg/ml polysorbate 20, wherein the pH of the liquid composition is between 5.1 and about 5.4. Also provided is a liquid composition (such as for intravenous administration) comprising a) about 2.7 mg/ml polatuzumab vedotin; b) about 1.35 mM sodium succinate; c) about 16.24 mM sucrose; d) about 0.162 mg/ml polysorbate 20, wherein the pH of the liquid composition is between about 5.1 and about 5.4. In some embodiment, the volume of the liquid composition is between about 50 ml and about 100 ml. In some embodiments, the volume of the liquid composition is 50 ml. In some embodiments, the volume of the liquid composition is 100 ml. In some embodiments, the liquid composition is contained in an intravenous (IV) bag. In some embodiments, the surfaces of the IV bag that contact the liquid composition are composed of polyvinylchloride (PVC), polyolefin (PO), polyethylene (PE), or polypropylene (PE).

In one aspect, the present disclosure provides a pharmaceutical composition comprising an anti-CD79b immunoconjugate, a surfactant, a succinate buffer, and a sugar, wherein the pharmaceutical composition, when reconstituted in water, forms a liquid formulation comprising the anti-CD79b immunoconjugate at a concentration of about 10 mg/ml to about 20 mg/ml, the surfactant at a concentration of at least 0.06% w/v (i.e., 0.6 mg/ml), the succinate buffer at a concentration of about 10 mM to about 200 mM, and the sugar at a concentration of about 100 mM to about 260 mM, wherein the liquid formulation has a pH of 5.3, and wherein the anti-CD79b immunoconjugate comprises the formula:

composition is reconstituted in SWFI and subsequently diluted into an isotonic buffer in an IV bag. In one embodiment, the surfactant concentration upon dilution in the IV bag is at least 0.003% w/v. In one embodiment, the surfactant concentration upon dilution in the IV bag is at least 0.004% w/v. In some embodiments, the surfactant is polysorbate 20. In some embodiments, the sugar is sucrose. In a specific embodiment, the sucrose is at a concentration of 120 mM. In some embodiments, the succinate buffer is a sodium succinate buffer. In a specific embodiment, the sodium succinate buffer is at a concentration of 10 mM. In some embodiments, pharmaceutical composition, following reconstitution, is stable for at least 4, 6, 8, 10, 12, 14, 16, 18, 20, 22, 24 hours upon storage at about 30° C. In some embodiments, the pharmaceutical composition, following reconstitution, is stable for at least 24, 48, or 72 hours upon storage at about 2° C. to about 8° C.

In some embodiments, the pharmaceutical composition, when reconstituted in water, has a stability of up to about 1 day, up to about 2 days, or up to about 3 days at 30° C. In some embodiments, the pharmaceutical composition, when reconstituted in water, has a stability of up to about 1 day, up to about 2 days, up to about 3 days, up to about 4 days, up to about 5 days, up to 6 days, or up to about 7 days at 5° C.±3° C. In certain embodiments, the stability of the com-

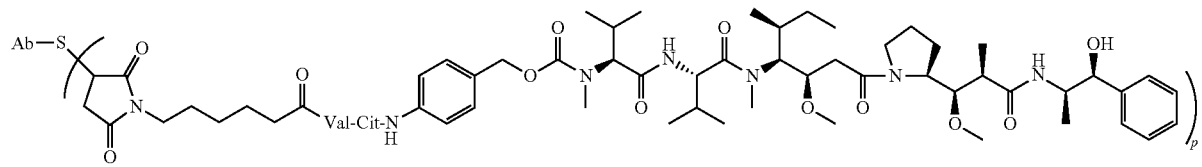

wherein Ab is an anti-CD79b antibody, wherein the anti-CD79b antibody comprises a heavy chain and a light chain, wherein the light chain comprises (a) an HVR-L1 sequence of KASQSVDYEGDSFLN (SEQ ID NO: 1); (b) an HVR-L2 sequence of AASNLES (SEQ ID NO: 2); and (c) an HVR-L3 sequence of QQSNEDPLT (SEQ ID NO: 3); wherein the heavy chain comprises (a) an HVR-H1 sequence of GYTFSSYWIE (SEQ ID NO: 4); (b) an HVR-H2 sequence of GEILPGGGDTNYNEIFKG (SEQ ID NO: 5); and (c) an HVR-H3 sequence of TRRVPIRLDY (SEQ ID NO: 6); Val is valine; Cit is citrulline; and p is a value from about 1 to about 8 (e.g., between about 2 and about 5, such as about 3.5). In some embodiments, the anti-CD79b antibody comprises a heavy chain variable domain (VH) comprising the amino acid sequence of SEQ ID NO: 7 and a light chain variable domain (VL) comprising the amino acid sequence of SEQ ID NO: 8. In some embodiments, the heavy chain of the anti-CD79b comprises the amino acid sequence of SEQ ID NO: 9, and the light chain of the anti-CD79b antibody comprises the amino acid sequence of SEQ ID NO: 10.

In some embodiments, the pharmaceutical composition is reconstituted in SWFI and subsequently diluted into a buffer in an IV bag. In certain embodiments, the pharmaceutical position is measured by size-exclusion high performance liquid chromatography (SE-HPLC). In a specific embodiment, the composition has a main peak (area %) of at least 95.0 as measured by SE-HPLC.

In certain embodiments, the stability of the composition is measured by imaged capillary isoelectric focusing (icIEF). In a specific embodiment, the composition has a main peak (area %) of at least 58.0, an acid region (area %) of at most 32.0, and a basic region (area %) of at most 12.0 as measured by icIEF.

In some embodiments, a pharmaceutical composition disclosed herein is contained in a glass vial (e.g., a 20 ml glass vial). In some embodiments, the pharmaceutical composition is a lyophilized pharmaceutical composition. In some embodiments, the pharmaceutical composition is a liquid pharmaceutical composition.

In one aspect, the present disclosure provides a pharmaceutical composition produced by a process comprising the steps of: (a) lyophilization of a liquid composition comprising 20 mg/ml of an anti-CD79b immunoconjugate in 10 mM sodium succinate buffer, 0.12% w/v of polysorbate 20, and 120 mM sucrose, wherein the liquid composition has a pH of 5.3, and wherein the anti-CD79b immunoconjugate comprises the formula:

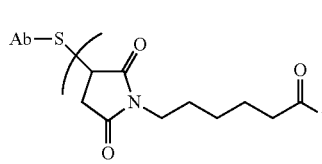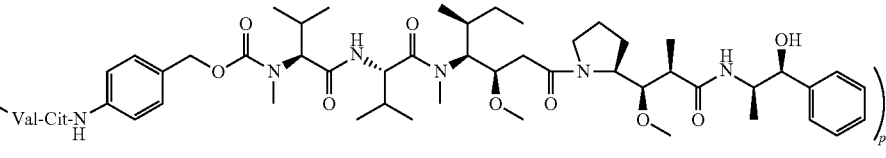

wherein: Ab is an anti-CD79b antibody, wherein the anti-CD79b antibody comprises a heavy chain and a light chain, wherein the heavy chain comprises the amino acid sequence of SEQ ID NO: 9, the light chain comprises the amino acid sequence of SEQ ID NO: 10; Val is valine; Cit is citrulline; and p is a value from about 2 to about 5, to produce a lyophilized composition; (b) reconstituting the lyophilized composition with about 7.2 ml sterile water for injection (SWFI) to produce a reconstituted composition; and (c) diluting the reconstituted composition into an isotonic buffer in an intravenous (IV) bag to produce the pharmaceutical composition, wherein the final volume of the pharmaceutical composition in the IV bag is about 100 ml, and wherein the final concentration of the immunoconjugate in the pharmaceutical composition is about 0.72 mg/ml or about 2.7 mg/ml.

In one aspect, the present disclosure provides a liquid composition comprising an anti-CD79b immunoconjugate, a surfactant, a succinate buffer, and a sugar, wherein the anti-CD79b immunoconjugate is at a concentration of about 10 mg/ml to about 20 mg/ml, the surfactant is at a concentration of at least 0.06% w/v (i.e., 0.6 mg/ml), the succinate buffer is at a concentration of about 10 mM to about 200 mM, and the sugar is at a concentration of about 100 mM to about 260 mM, wherein the liquid composition has a pH of 5.3, and wherein the anti-CD79b immunoconjugate comprises the formula:

In some embodiments, the surfactant is polysorbate 20. In some embodiments, the sugar is sucrose. In a specific embodiment, the sucrose is at a concentration of 120 mm. In some embodiments, the succinate buffer is a sodium succinate buffer. In a specific embodiment, the sodium succinate buffer is at a concentration of 10 mM.

In some embodiments, the liquid composition of the present disclosure is diluted into in an isotonic buffer. In an exemplary embodiment, the liquid composition of the present disclosure dissolved in an isotonic buffer is in an IV bag. In some embodiments, the isotonic buffer into which the liquid composition is diluted is an 0.9% sodium chloride solution, an 0.45% sodium chloride solution, or a 5% dextrose solution.

In some embodiments, a liquid composition provided herein that has been diluted in 0.9% sodium chloride solution is stable (according to any one or more criteria described elsewhere herein) following dilution for up to at least about 24 hours at 2° C.-8° C. In some embodiments, a liquid composition provided herein that has been diluted in 0.9% sodium chloride solution is stable (according to any one or more criteria described elsewhere herein) following dilution for up to about 4 hours at 9° C. to 25° C. In some embodiments, a liquid composition provided herein that has been diluted in 0.45% sodium chloride solution is stable (according to any one or more criteria described elsewhere herein) following dilution for up to at least about 24 hours

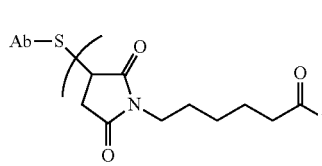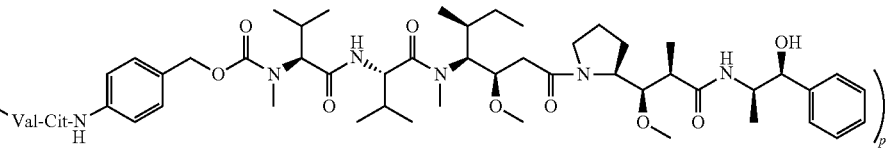

wherein:
Ab is an anti-CD79b antibody, wherein the anti-CD79b antibody comprises a heavy chain and a light chain, wherein the light chain comprises (a) an HVR-L1 sequence of KASQSVDYEGDSFLN (SEQ ID NO: 1); (b) an HVR-L2 sequence of AASNLES (SEQ ID NO: 2); and (c) an HVR-L3 sequence of QQSNEDPLT (SEQ ID NO: 3); wherein the heavy chain comprises (a) an HVR-H1 sequence of GYTFSSYWIE (SEQ ID NO: 4); (b) an HVR-H2 sequence of GEILPGGGDTNYNEIFKG (SEQ ID NO: 5); and (c) an HVR-H3 sequence of TRRVPIRLDY (SEQ ID NO: 6); Val is valine; Cit is citrulline; and p is a value from about 1 to about 8 (e.g., between about 2 and about 5, such as about 3.5). In some embodiments, the anti-CD79b antibody comprises a heavy chain variable domain (VH) comprising the amino acid sequence of SEQ ID NO: 7 and a light chain variable domain (VL) comprising the amino acid sequence of SEQ ID NO: 8. In some embodiments, the heavy chain of the anti-CD79b comprises the amino acid sequence of SEQ ID NO: 9, and the light chain of the anti-CD79b antibody comprises the amino acid sequence of SEQ ID NO: 10.

at 2° C.-8° C. In some embodiments, a liquid composition provided herein that has been diluted in 0.45% sodium chloride solution is stable (according to any one or more criteria described elsewhere herein) following dilution for up to about 4 hours at 9° C. to 25° C. In some embodiments, a liquid composition provided herein that has been diluted in 5% dextrose solution is stable (according to any one or more criteria described elsewhere herein) following dilution for up to at least about 48 hours at 2° C.-8° C. In some embodiments, a liquid composition provided herein that has been diluted in 5% dextrose solution is stable (according to any one or more criteria described elsewhere herein) following dilution for up to about 8 hours at 9° C. to 25° C.

In some embodiments, the liquid composition that is diluted in an isotonic buffer is in an IV bag. In some embodiments, the surfaces of the IV bag that contact the composition that is-diluted in an isotonic buffer are composed of polyvinylchloride (PVC), polyolefin (PO), polyethylene (PE), or polypropylene (PE).

In some embodiments, the liquid composition of the present disclosure diluted in an isotonic buffer in an IV bag has a stability of up to about 6 to about 8 hours at 30° C. In some embodiments, the liquid composition of the present disclosure dissolved in an isotonic buffer in an IV bag has a stability of up to about 24 hours at 25° C. In some embodiments, the liquid composition of the present disclosure dissolved in an isotonic buffer in an IV bag has a stability of up to about 72 hours at 5° C.±3° C. In certain embodiments, the isotonic buffer is normal saline. In some embodiments, the liquid composition is stable for at least 4, 6, 8, 10, 12, 14, 16, 18, 20, 22, 24 hours upon storage at about 30° C. In some embodiments, the liquid composition is stable for at least 24, 48, or 72 hours upon storage at about 2° C. to about 8° C.

Also provided is lyophilized pharmaceutical composition comprising about 150 mg of an anti-CD79b immunoconjugate, about 9.0 mg polysorbate 20, about 8.88 mg succinic acid, about 4.08 mg sodium hydroxide, and about 309 mg sucrose, wherein the anti-CD79b immunoconjugate comprises the formula:

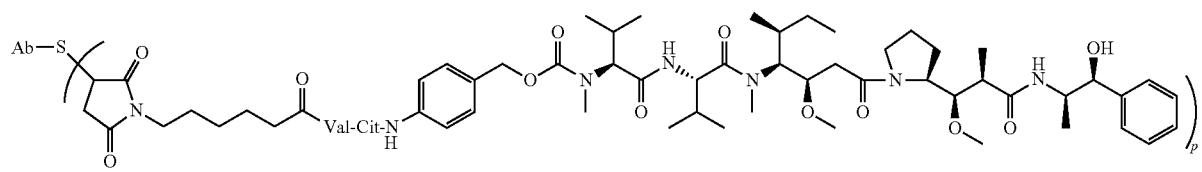

wherein Ab is an anti-CD79b antibody, wherein the anti-CD79b antibody comprises a heavy chain and a light chain, wherein the heavy chain of the anti-CD79b comprises the amino acid sequence of SEQ ID NO: 9, and wherein the light chain of the anti-CD79b antibody comprises the amino acid sequence of SEQ ID NO: 10; Val is valine; Cit is citrulline; and p is a value from about 2 to about 5 (such as about 3.5). In some embodiments, the lyophilized composition (such as a cake) is contained in a vial, e.g., a 20 ml glass vial.

Further provided is a lyophilized pharmaceutical composition comprising about 150 mg of polatuzumab vedotin, about 9.0 mg polysorbate 20, about 8.88 mg succinic acid, about 4.08 mg sodium hydroxide, and about 309 mg sucrose. In some embodiments, the lyophilized composition (such as a cake) is contained in a vial, e.g., a 20 ml glass vial.

Also provided is a lyophilized pharmaceutical composition comprising about 140 mg of an anti-CD79b immunoconjugate, about 8.4 mg polysorbate 20, about 8.27 mg succinic acid, about 3.80 mg sodium hydroxide, and about 288 mg sucrose, wherein the anti-CD79b immunoconjugate comprises the formula:

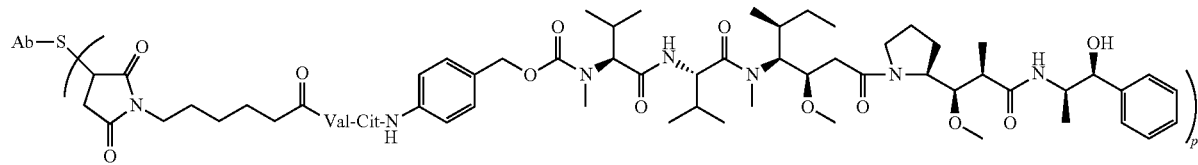

wherein b is an anti-CD79b antibody, wherein the anti-CD79b antibody comprises a heavy chain and a light chain, wherein the heavy chain of the anti-CD79b comprises the amino acid sequence of SEQ ID NO: 9, and wherein the light chain of the anti-CD79b antibody comprises the amino acid sequence of SEQ ID NO: 10; Val is valine; Cit is citrulline; and p is a value from about 2 to about 5 (such as about 3.5). In some embodiments, the lyophilized composition (such as a cake) is contained in a vial, e.g., a 20 ml glass vial.

Further provide is a lyophilized pharmaceutical composition comprising about 140 mg of polatuzumab vedotin, about 8.4 mg polysorbate 20, about 8.27 mg succinic acid, about 3.80 mg sodium hydroxide, and about 288 mg sucrose. In some embodiments, the lyophilized composition (such as a cake) is contained in a vial, e.g., a 20 ml glass vial.

Also provided is a lyophilized pharmaceutical composition comprising about 30 mg of an anti-CD79b immunoconjugate, about 1.8 mg polysorbate 20, about 1.77 mg succinic acid, about 0.816 mg sodium hydroxide, and about 61.8 mg sucrose, wherein the anti-CD79b immunoconjugate comprises the formula:

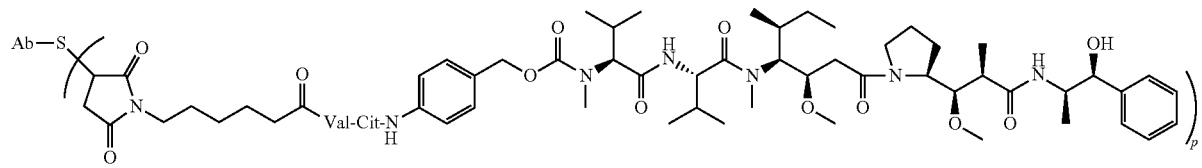

wherein Ab is an anti-CD79b antibody, wherein the anti-CD79b antibody comprises a heavy chain and a light chain, wherein the heavy chain of the anti-CD79b comprises the amino acid sequence of SEQ ID NO: 9, and wherein the light chain of the anti-CD79b antibody comprises the amino acid sequence of SEQ ID NO: 10; Val is valine; Cit is citrulline; and p is a value from about 2 to about 5 (such as about 3.5). In some embodiments, the lyophilized composition is a lyophilized cake. In some embodiments, the lyophilized composition (such as a cake) is contained in a vial, e.g., a 20 ml glass vial.

Further provided is a lyophilized pharmaceutical composition comprising about 30 mg of polatuzumab vedotin, about 1.8 mg polysorbate 20, about 1.77 mg succinic acid, about 0.816 mg sodium hydroxide, and about 61.8 mg sucrose. In some embodiments, the lyophilized composition (such as a cake) is contained in a vial, e.g., a 20 ml glass vial.

In some embodiments, a lyophilized pharmaceutical composition provided herein is a lyophilized cake. In some embodiments, a lyophilized pharmaceutical composition according to any of the embodiments herein is stable for at least 6, 12, 18, 24, 30, 36, 42, 48, 54, or 60 months upon storage at about 2° C. to about 8° C.

Provided is a liquid pharmaceutical composition comprising a) between about 5-60 mg/ml polatuzumab vedotin; b) between about 10-200 mM sodium succinate; c) between about 100-260 mM sucrose; and d) between about 0.06-0.12% w/v polysorbate 20, wherein the pH of the liquid compositions is between 5 and 6. In some embodiments, the liquid pharmaceutical composition comprises a) between about 10-55 mg/ml polatuzumab vedotin; b) between about 10-100 mM sodium succinate; c) between about 150-260 mM sucrose; and d) between about 0.08-0.12% w/v polysorbate 20, wherein the pH of the liquid compositions is between 5.1 and 5.6. In some embodiments, the liquid pharmaceutical composition comprises a) between about 15-40 mg/ml polatuzumab vedotin; b) between about 10-50 mM sodium succinate; c) between about 200-260 mM sucrose; and d) between about 0.1-0.12% w/v polysorbate 20, wherein the pH of the liquid compositions is between 5.2 and 5.4. In some embodiments, the liquid composition is obtained by reconstituting a lyophilized composition (such as a cake). In some embodiments, the liquid composition is contained in a vial, e.g., a 20 ml glass vial.

Also provided is a liquid pharmaceutical composition comprising a) 20 mg/ml polatuzumab vedotin; b) 10 mM sodium succinate; c) 120 mM sucrose; and d) 0.12% w/v polysorbate 20, wherein the pH of the liquid compositions is about 5.3. In some embodiments, the liquid composition is obtained by reconstituting a lyophilized composition (such as a cake). In some embodiments, the liquid composition is contained in a vial, e.g., a 20 ml glass vial.

In some embodiments, a liquid composition according to any of the embodiments herein is stable for at least 4, 6, 8, 10, 12, 14, 16, 18, 20, 22, 24 hours upon storage at about 30° C. In some embodiments, a liquid composition according to any of the embodiments herein is stable for at least 24, 48, or 72 hours upon storage at about 2° C. to about 8° C. In some embodiments, the liquid composition is obtained by reconstituting a lyophilized composition (such as a cake). In some embodiments, the liquid composition is contained in a vial, e.g., a 20 ml glass vial.

In some embodiments, a reconstituted pharmaceutical composition provided herein is stable after 72 hours of storage at 2° C.-8° C. In some embodiments, a reconstituted pharmaceutical composition provided herein is stable after 24 hours of storage at 30° C. with exposure to ambient light. In some embodiments, the reconstituted pharmaceutical composition comprises a 20 mg/mL polatuzumab vedotin in 10 mM succinate, 120 mM sucrose, and 1.2 mg/mL polysorbate 20, wherein the pH is 5.3. In some embodiment the affinity of polatuzumab vedotin for its target (i.e., CD79b) or in the biological activity of polatuzumab vedotin In one aspect, the present disclosure provides a method of treating a proliferative disorder in a patient in need thereof including administering to a patient the pharmaceutical composition or a liquid composition described herein. Also provided is the use of a pharmaceutical composition or liquid composition described herein for the manufacture of a medicament for treating a proliferative disorder in a patient in need thereof. In some embodiments, provided is a pharmaceutical composition or liquid composition described herein for use in the treatment of a proliferative disorder in a patient in need thereof. Also provided is a pharmaceutical composition or a liquid composition described herein for use in a method of treating a proliferative disorder in a patient in need thereof.

In some embodiments, the proliferative disorder is cancer. In an exemplary embodiment, the cancer is a B cell proliferative disorder. In specific embodiments, the B cell proliferative disorder is selected from the group consisting of: lymphoma, myeloma, non-Hodgkin's lymphoma (NHL), diffuse large B-cell lymphoma (DLBCL), relapsed/refractory DLBCL aggressive NHL, indolent lymphoma, follicular lymphoma (FL), relapsed aggressive NHL, relapsed indolent NHL, relapsed NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma.

In one embodiment of the present disclosure, the B cell proliferative disorder is non-Hodgkin's lymphoma (NHL). In one embodiment, the B cell proliferative disorder is diffuse large B-cell lymphoma (DLBCL). In one embodiment, the B cell proliferative disorder is relapsed/refractory DLBCL. In some embodiments, the B cell proliferative disorder is relapsed/refractory DLBCL. In another embodiment, the B cell proliferative disorder is relapsed NHL or refractory NHL. In still another embodiment, the B cell proliferative disorder is follicular lymphoma (FL).

DESCRIPTION OF THE FIGURES

FIG. 15A-FIG. 15C depict the lyophilized cake appearance with varying protein to sucrose ratios. FIG. 15A represents 10 mg/ml of anti-CD79b-vc-MMAE and 260 mM sucrose. FIG. 15B represents 10 mg/ml of anti-CD79b-vc-MMAE and 180 mM sucrose. FIG. 15C represents 10 mg/ml of anti-CD79b-vc-MMAE and 120 mM sucrose.

FIG. 16A represents 10 mg/ml of anti-CD79b-vc-MMAE and 260 mM sucrose. FIG. 16B represents 20 mg/ml of anti-CD79b-vc-MMAE and 120 mM sucrose.

DETAILED DESCRIPTION

Figure 1:
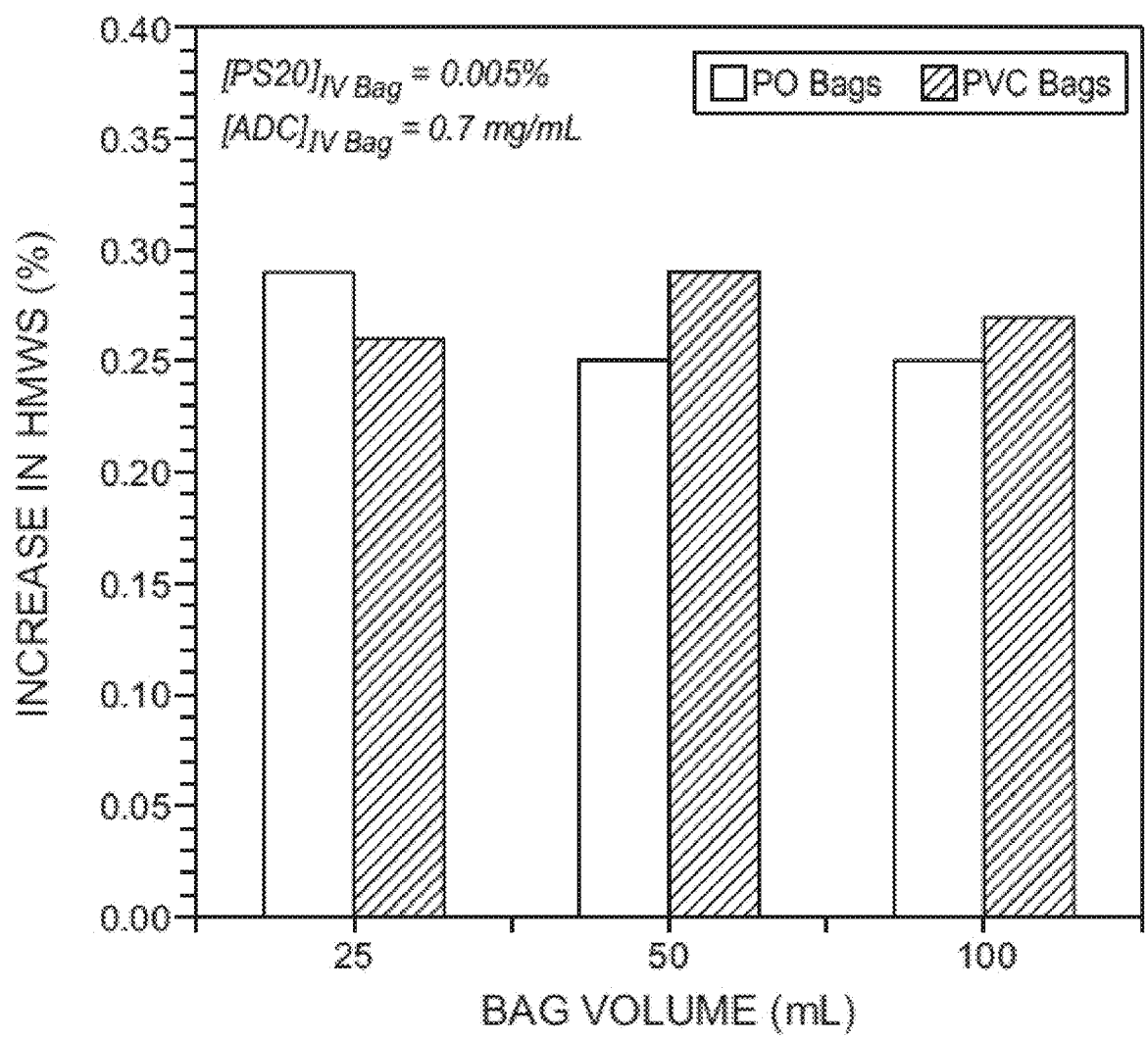
FIG. 1 depicts an increase in high molecular weight species (HMWS) after 22 hours of static storage at 30° C. with a fixed concentration of PS20 ([PS20]) in three different intravenous (IV) bag sizes.

The present disclosure provides stable pharmaceutical compositions comprising an anti-CD79b immunoconjugate and a surfactant. The disclosure also provides methods for using such compositions for the treatment of cancer.

I. Definitions

It is to be understood that this disclosure is not limited to particular compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the disclosure described herein include "comprising," "consisting," and "consisting essentially of" aspects and embodiments.

The term "anti-CD79b immunoconjugate" refers to an anti-CD79b antibody-drug conjugate (ADC). As used herein, the anti-CD79b immunoconjugate contains an antibody or fragment thereof capable of binding CD79b, a linker, and a drug molecule. The term "linker" is used refer to 6-maleimidocaproyl-valine-citrulline-p-aminobenzyloxycarbonyl (MC-val-cit-PAB).

The term "antibody" is used in the broadest sense and specifically covers, for example, single anti-CD79b monoclonal antibodies (including, without limitation, agonist, antagonist, neutralizing antibodies, full length or intact monoclonal antibodies), anti-CD79b antibody compositions with polyepitopic specificity, polyclonal antibodies, multivalent antibodies, multispecific antibodies (e.g., bispecific antibodies so long as they exhibit the desired biological activity) formed from at least two intact antibodies, single chain anti-CD79b antibodies, and fragments of anti-CD79b antibodies (see below), including Fab, Fab', F(ab')2 and Fv fragments, diabodies, single domain antibodies (sdAbs), as long as they exhibit the desired biological or immunological activity. The term "immunoglobulin" (Ig) is used interchangeable with antibody herein. An antibody can be chimeric, human, humanized and/or affinity matured.

The term "anti-CD79b antibody" or "an antibody that binds to CD79b" refers to an antibody that is capable of binding CD79b with sufficient affinity such that the antibody is useful as a diagnostic and/or therapeutic agent in targeting CD79b. Preferably, the extent of binding of an anti-CD79b antibody to an unrelated, non-CD79b protein is less than about 10% of the binding of the antibody to CD79b as measured, e.g., by a radioimmunoassay (RIA). In certain embodiments, an antibody that binds to CD79b has a dissociation constant (Kd) of ≤1 µM, ≤100 nM, ≤10 nM, ≤1 nM, or ≤0.1 nM. In certain embodiments, anti-CD79b antibody binds to an epitope of CD79b that is conserved among CD79b from different species.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for µ and ε isotypes. Each L chain has at the N-terminus, a variable domain (VL) followed by a constant domain (CL) at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated α, δ, ε, γ, and µ, respectively. The γ and a classes are further divided into subclasses on the basis of relatively minor differences in CH sequence and function, e.g., humans express the following subclasses: IgG1, IgG2, IgG3, IgG4, IgA1, and IgA2.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain segments of the variable domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

An "intact" antibody is one which comprises an antigen-binding site as well as a CL and at least heavy chain constant domains, CH1, CH2 and CH3. The constant domains may be native sequence constant domains (e.g. human native sequence constant domains) or amino acid sequence variant thereof. Preferably, the intact antibody has one or more effector functions.

A "naked antibody" for the purposes herein is an antibody that is not conjugated to a drug moiety or radiolabel.

"Antibody fragments" comprise a portion of an intact antibody, preferably the antigen binding or variable region of the intact antibody. Examples of antibody fragments include Fab, Fab', F(ab')2, and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments. In one embodiment, an antibody fragment comprises an antigen binding site of the intact antibody and thus retains the ability to bind antigen.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH1). Each Fab fragment is monovalent with respect to antigen binding, i.e., it has a single antigen-binding site. Pepsin treatment of an antibody yields a single large F(ab')2 fragment which roughly corresponds to two disulfide linked Fab fragments having divalent antigen-binding activity and is still capable of cross-linking antigen. Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to antibody fragments with two antigen-binding sites, which fragments comprise a heavy-chain variable domain (VH) connected to a light-chain variable domain (VL) in the same polypeptide chain (VH-VL). The small antibody fragments are prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Diabodies may be bivalent or bispecific. Bispecific diabodies are heterodimers of two "crossover" sFv fragments in which the VH and VL domains of the two antibodies are present on different polypeptide chains. Diabodies are described more fully in, for example, EP 404,097; WO 93/11161; Hudson et al., Nat. Med. 9:129-134 (2003); and Hollinger et al., Proc. Natl. Acad. Sci. USA, 90:6444-6448 (1993). Triabodies and tetrabodies are also described in Hudson et al., Nat. Med. 9:129-134 (2003).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present disclosure may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222: 581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, Ape etc.), and human constant region sequences.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma and Immunol., 1:105-115 (1998); Harris, Biochem. Soc. Transactions, 23:1035-1038 (1995); Hurle and Gross, Curr. Op. Biotech., 5:428-433 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol., 227:381 (1991); Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., Proc. Natl. Acad. Sci. USA, 103:3557-3562 (2006) regarding human antibodies generated via a human B-cell hybridoma technology.

The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

| Loop | Kabat | AbM | Chothia | Contact |
|---|---|---|---|---|
| L1 | L24-L34 | L24-L34 | L24-L34 | L30-L36 |
| L2 | L50-L56 | L50-L56 | L50-L56 | L46-L55 |
| L3 | L89-L97 | L89-L97 | L89-L97 | L89-L96 |
| H1 | H31-H35B (Kabat Numbering) | H26-H35B | H26-H32..34 | H30-H35B |
| H1 | H31-H35 (Chothia Numbering) | H26-H35 | H26-H32 | H30-H35 |
| H2 | H50-H65 | H50-H58 | H52-H56 | H47-H58 |
| H3 | H95-H102 | H95-H102 | H95-H102 | H93-H101 |

Hypervariable regions may comprise "extended hypervariable regions" as follows: 24-36 or 24-34 (Li), 46-56 or 50-56 (L2) and 89-97 (L3) in the VL and 26-35B (H1), 50-65, 47-65 or 49-65 (H2) and 93-102, 94-102 or 95-102 (H3) in the VH. The variable domain residues are numbered according to Kabat et al., supra for each of these definitions.

"Framework" or "FR" residues are those variable domain residues other than the hypervariable region residues herein defined.

The term "variable domain residue numbering as in Kabat" or "amino acid position numbering as in Kabat", and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see U.S. Provisional Application No. 60/640,323, Figures for EU numbering).

An "affinity matured" antibody is one with one or more alterations in one or more HVRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. Bio/Technology 10:779-783 (1992) describes affinity maturation by VH and VL domain shuffling. Random mutagenesis of HVR and/or framework residues is described by: Barbas et al. Proc Nat. Acad. Sci, USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al, J. Mol. Biol. 226:889-896 (1992).

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. Specific illustrative embodiments are described in the following.

"Or better" when used herein to refer to binding affinity refers to a stronger binding between a molecule and its binding partner. "Or better" when used herein refers to a stronger binding, represented by a smaller numerical Kd value. For example, an antibody which has an affinity for an antigen of "0.6 nM or better", the antibody's affinity for the antigen is <0.6 nM, i.e. 0.59 nM, 0.58 nM, 0.57 nM etc. or any value less than 0.6 nM.

In one embodiment, the "Kd" or "Kd value" according to this disclosure is measured by a radiolabeled antigen binding assay (RIA) performed with the Fab version of an antibody of interest and its antigen as described by the following assay that measures solution binding affinity of Fabs for antigen by equilibrating Fab with a minimal concentration of ($125I$)-labeled antigen in the presence of a titration series of unlabeled antigen, then capturing bound antigen with an anti-Fab antibody-coated plate (Chen, et al., (1999) J. Mol Biol 293:865-881). To establish conditions for the assay, microtiter plates (Dynex) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [125I]-antigen are mixed with serial dilutions of a Fab of interest (e.g., consistent with assessment of an anti-VEGF antibody, Fab-12, in Presta et al., (1997) Cancer Res. 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 µl/well of scintillant (MicroScint-20; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment the "Kd" or "Kd value" is measured by using surface plasmon resonance assays using a BIAcore™-2000 or a BIAcore™-3000 (BIAcore, Inc., Piscataway, N.J.) at 25 C with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 ug/ml (~0.2 uM) before injection at a flow rate of 5 ul/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio koff/kon. See, e.g., Chen, Y., et al., (1999) J. Mol Biol 293:865-881. If the on-rate exceeds $10^6$ $M^{-1}S^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stir red cuvette.

An "on-rate" or "rate of association" or "association rate" or "$k_{off}$" according to this disclosure can also be determined with the same surface plasmon resonance technique described above using a BIAcore™-2000 or a BIAcore™-3000 (BIAcore, Inc., Piscataway, N.J.) as described above.

The phrase "substantially similar," or "substantially the same", as used herein, denotes a sufficiently high degree of similarity between two numeric values (generally one associated with an antibody of the disclosure and the other associated with a reference/comparator antibody) such that one of skill in the art would consider the difference between the two values to be of little or no biological and/or statistical significance within the context of the biological characteristic measured by said values (e.g., Kd values). The difference between said two values is preferably less than about 50%, preferably less than about 40%, preferably less than about 30%, preferably less than about 20%, preferably less than about 10% as a function of the value for the reference/comparator antibody.

The phrase "substantially reduced," or "substantially different", as used herein, denotes a sufficiently high degree of difference between two numeric values (generally one associated with an antibody of the disclosure and the other associated with a reference/comparator antibody) such that one of skill in the art would consider the difference between the two values to be of statistical significance within the context of the biological characteristic measured by said values (e.g., Kd values, HAMA response). The difference between said two values is preferably greater than about 10%, preferably greater than about 20%, preferably greater than about 30%, preferably greater than about 40%, preferably greater than about 50% as a function of the value for the reference/comparator antibody.

An "acceptor human framework" for the purposes herein is a framework comprising the amino acid sequence of a VL or VH framework derived from a human immunoglobulin framework, or from a human consensus framework. An acceptor human framework "derived from" a human immunoglobulin framework or human consensus framework may comprise the same amino acid sequence thereof, or may contain pre-existing amino acid sequence changes. Where pre-existing amino acid changes are present, preferably no more than 5 and preferably 4 or less, or 3 or less, pre-existing amino acid changes are present. Where pre-existing amino acid changes are present in a VH, preferably those changes are only at three, two or one of positions 71H, 73H and 78H; for instance, the amino acid residues at those positions may be 71A, 73T and/or 78A. In one embodiment, the VL acceptor human framework is identical in sequence to the VL human immunoglobulin framework sequence or human consensus framework sequence.

A "human consensus framework" is a framework which represents the most commonly occurring amino acid residue in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al. In one embodiment, for the VL, the subgroup is subgroup kappa I as in Kabat et al. In one embodiment, for the VH, the subgroup is subgroup III as in Kabat et al.

A "VH subgroup III consensus framework" comprises the consensus sequence obtained from the amino acid sequences in variable heavy subgroup III of Kabat et al. In one embodiment, the VH subgroup III consensus framework amino acid sequence comprises at least a portion or all of each of the following sequences: EVQLVESGG-GLVQPGGSLRLSCAAS (SEQ ID NO: 11)-H1-WVRQAPGKGLEWV (SEQ ID NO: 12)-H2-RFTIS-RDNSKNTLYLQMNSLRAEDTAVYYC (SEQ ID NO: 145)-H3-WGQGTLVTVSS (SEQ ID NO: 13).

A "VL subgroup I consensus framework" comprises the consensus sequence obtained from the amino acid sequences in variable light kappa subgroup I of Kabat et al. In one embodiment, the VL subgroup I consensus framework amino acid sequence comprises at least a portion or all of each of the following sequences: DIQMTQSPSSL-SASVGDRVTITC (SEQ ID NO: 14)-L1-

WYQQKPGKAPKLLIY (SEQ ID NO: 15)-L2-GVPSRFSGSGSGTDFTLTISSLQPEDFATYYC (SEQ ID NO: 141)-L3-FGQGTKVEIKR (SEQ ID NO: 16).

An "unmodified human framework" is a human framework which has the same amino acid sequence as the acceptor human framework, e.g. lacking human to non-human amino acid substitution(s) in the acceptor human framework.

An anti-CD79b immunoconjugate or antibody "which binds" CD79b is one that binds the CD79b antigen with sufficient affinity such that the antibody is useful as a therapeutic agent in targeting a cell or tissue expressing the antigen, and does not significantly cross-react with other proteins. In such embodiments, the extent of binding of the antibody to a "non-target" protein will be less than about 10% of the binding of the antibody to its particular target protein as determined by fluorescence activated cell sorting (FACS) analysis or radioimmunoprecipitation (RIA). With regard to the binding of an antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where an antibody binds to an epitope on a CD79b polypeptide without substantially binding to any other polypeptide or polypeptide epitope.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

A "functional Fc region" possesses an "effector function" of a native sequence Fc region. Exemplary "effector functions" include C1q binding; CDC; Fc receptor binding; ADCC; phagocytosis; down regulation of cell surface receptors (e.g. B cell receptor; BCR), etc. Such effector functions generally require the Fc region to be combined with a binding domain (e.g., an antibody variable domain) and can be assessed using various assays as disclosed, for example, in definitions herein.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. (USA) 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, Annu. Rev. Immunol. 15:203-234 (1997)). FcRs are reviewed in Ravetch and Kinet, Annu. Rev. Immunol. 9:457-492 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

Binding to human FcRn in vivo and serum half-life of human FcRn high affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with improved or diminished binding to FcRs. See also, e.g., Shields et al. J. Biol. Chem. 9(2):6591-6604 (2001).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., J. Immunol. Methods 202:163 (1996), may be performed. Polypeptide variants with altered Fc region amino acid sequences (polypeptides with a variant Fc region) and increased or decreased C1q binding capability are described, e.g., in U.S. Pat. No. 6,194,551 B1 and WO 1999/51642. See also, e.g., Idusogie et al. J. Immunol. 164: 4178-4184 (2000).

The term "Fc region-comprising antibody" refers to an antibody that comprises an Fc region. The C-terminal lysine (residue 447 according to the EU numbering system) of the Fc region may be removed, for example, during purification of the antibody or by recombinant engineering of the nucleic acid encoding the antibody. Accordingly, a composition comprising an antibody having an Fc region according to this disclosure can comprise an antibody with K447, with all K447 removed, or a mixture of antibodies with and without the K447 residue.

A "B-cell surface marker" or "B-cell surface antigen" herein is an antigen expressed on the surface of a B cell that can be targeted with an antagonist that binds thereto, including but not limited to, antibodies to a B-cell surface antigen or a soluble form a B-cell surface antigen capable of antagonizing binding of a ligand to the naturally occurring B-cell antigen. Exemplary B-cell surface markers include the CD10, CD19, CD20, CD21, CD22, CD23, CD24, CD37, CD40, CD53, CD72, CD73, CD74, CDw75, CDw76, CD77, CDw78, CD79a, CD79b, CD80, CD81, CD82, CD83, CDw84, CD85 and CD86 leukocyte surface markers (for descriptions, see The Leukocyte Antigen Facts Book, 2nd Edition. 1997, ed. Barclay et al. Academic Press, Harcourt Brace & Co., New York). Other B-cell surface markers include RP105, FcRH2, B-cell CR2, CCR6, P2X5, HLA-DOB, CXCR5, FCER2, BR3, BAFF, BLyS, Btig, NAG14, SLGC16270, FcRH1, IRTA2, ATWD578, FcRH3, IRTA1, FcRH6, BCMA, and 239287. The B-cell surface marker of particular interest is preferentially expressed on B cells compared to other non-B-cell tissues of a mammal and may be expressed on both precursor B cells and mature B cells.

The terms "cancer" and "cancerous" refer to or describe the physiological condition in mammals that is typically characterized by unregulated cell growth. Examples of cancer include, but are not limited to, hematopoietic cancers or blood-related cancers, such as lymphoma, leukemia, myeloma or lymphoid malignancies, but also cancers of the spleen and cancers of the lymph nodes and also carcinoma, blastoma and sarcoma. More particular examples of cancer include B-cell associated cancers, including for example, high, intermediate and low grade lymphomas (including B cell lymphomas such as, for example, mucosa-associated-lymphoid tissue B cell lymphoma and non-Hodgkin's lymphoma (NHL), mantle cell lymphoma, Burkitt's lymphoma, small lymphocytic lymphoma, marginal zone lymphoma, diffuse large B cell lymphoma (DLBCL), follicular lymphoma (FL), and Hodgkin's lymphoma and T cell lymphomas) and leukemias (including secondary leukemia, chronic lymphocytic leukemia (CLL), such as B cell leukemia (CD5+ B lymphocytes), myeloid leukemia, such as acute myeloid leukemia, chronic myeloid leukemia, lymphoid leukemia, such as acute lymphoblastic leukemia (ALL) and myelodysplasia), and other hematological and/or B cell- or T-cell-associated cancers. Also included are cancers of additional hematopoietic cells, including polymorphonuclear leukocytes, such as basophils, eosinophils, neutrophils and monocytes, dendritic cells, platelets, erythrocytes and natural killer cells. Also included are cancerous B cell proliferative disorders selected from the following: lymphoma, non-Hodgkin's lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), DLBCL, relapsed/refractory DLBCL, FL, and mantle cell lymphoma. The origins of B-cell cancers include as follows: marginal zone B-cell lymphoma originates in memory B-cells in marginal zone, follicular lymphoma and diffuse large B-cell lymphoma originates in centrocytes in the light zone of germinal centers, chronic lymphocytic leukemia and small lymphocytic leukemia originates in B1 cells (CD5+), mantle cell lymphoma originates in naive B-cells in the mantle zone and Burkitt's lymphoma originates in centroblasts in the dark zone of germinal centers. Tissues which include hematopoietic cells referred herein to as "hematopoietic cell tissues" include thymus and bone marrow and peripheral lymphoid tissues, such as spleen, lymph nodes, lymphoid tissues associated with mucosa, such as the gut-associated lymphoid tissues, tonsils, Peyer's patches and appendix and lymphoid tissues associated with other mucosa, for example, the bronchial linings. Further particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

A "B-cell malignancy" or "B cell proliferative disorder" herein includes non-Hodgkin's lymphoma (NHL), including low grade/follicular NHL, small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, mantle cell lymphoma, AIDS-related lymphoma, and Waldenstrom's Macroglobulinemia, non-Hodgkin's lymphoma (NHL), DLBCL, relapsed/refractory DLBCL, FL, lymphocyte predominant Hodgkin's disease (LPHD), small lymphocytic lymphoma (SLL), chronic lymphocytic leukemia (CLL), indolent NHL including relapsed indolent NHL and rituximab-refractory indolent NHL; leukemia, including acute lymphoblastic leukemia (ALL), chronic lymphocytic leukemia (CLL), Hairy cell leukemia, chronic myeloblastic leukemia; mantle cell lymphoma; and other hematologic malignancies. Such malignancies may be treated with antibodies directed against B-cell surface markers, such as CD79b. Such diseases are contemplated herein to be treated by the administration of an antibody directed against a B cell surface marker, such as CD79b, and includes the administration of an unconjugated ("naked") antibody or an antibody conjugated to a cytotoxic agent as disclosed herein. Such diseases are also contemplated herein to be treated by combination therapy including an anti-CD79b antibody or anti-CD79b antibody drug conjugate of the disclosure in combination with another antibody or antibody drug conjugate, another cytotoxic agent, radiation or other treatment administered simultaneously or in series. In exemplary treatment method of the disclosure, an anti-CD79b antibody of the disclosure is administered in combination with an anti-CD20 antibody, immunoglobulin, or CD20 binding fragment thereof, either together or sequentially. The anti-CD20 antibody may be a naked antibody or an antibody drug conjugate. In an embodiment of the combination therapy, the anti-CD79b antibody is an antibody of the present disclosure and the anti-CD20 antibody is Rituxan® (rituximab).

Figure 11:
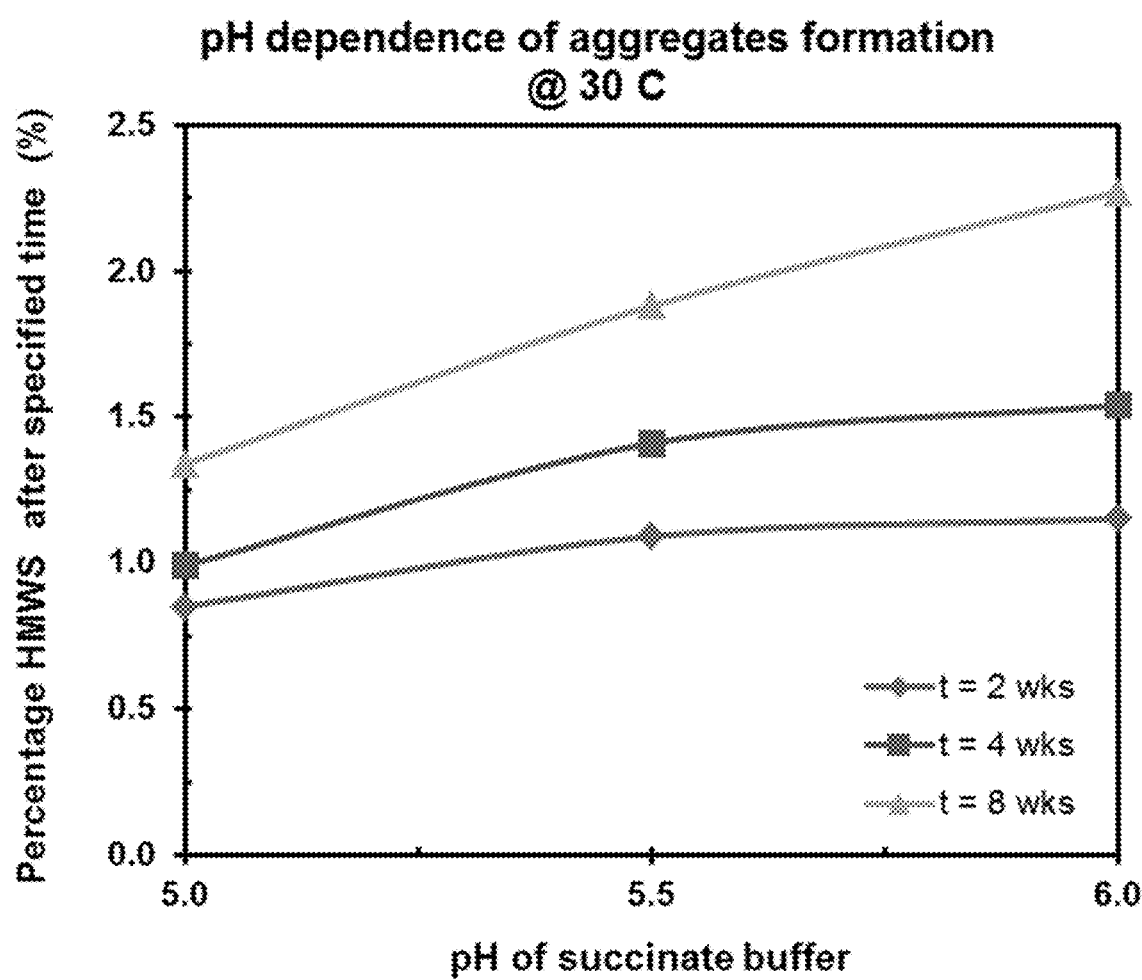
FIG. 11 depicts the effect of pH on HMWS formation at 30° C. at three different time points: 2 weeks, 4 weeks and 8 weeks.

The term "non-Hodgkin's lymphoma" or "NHL", as used herein, refers to a cancer of the lymphatic system other than Hodgkin's lymphomas. Hodgkin's lymphomas can generally be distinguished from non-Hodgkin's lymphomas by the presence of Reed-Sternberg cells in Hodgkin's lymphomas and the absence of said cells in non-Hodgkin's lymphomas. Examples of non-Hodgkin's lymphomas encompassed by the term as used herein include any that would be identified as such by one skilled in the art (e.g., an oncologist or pathologist) in accordance with classification schemes known in the art, such as the Revised European-American Lymphoma (REAL) scheme as described in Color Atlas of Clinical Hematology (3rd edition), A. Victor Hoffbrand and John E. Pettit (eds.) (Harcourt Publishers Ltd., 2000). See, in particular, the lists in FIG. 11.57, 11.58 and 11.59. More specific examples include, but are not limited to, relapsed or refractory NHL, front line low grade NHL, Stage III/IV NHL, chemotherapy resistant NHL, precursor B lymphoblastic leukemia and/or lymphoma, small lymphocytic lymphoma, B cell chronic lymphocytic leukemia and/or prolymphocytic leukemia and/or small lymphocytic lymphoma, B-cell prolymphocytic lymphoma, immunocytoma and/or lymphoplasmacytic lymphoma, lymphoplasmacytic lymphoma, marginal zone B cell lymphoma, splenic marginal zone lymphoma, extranodal marginal zone—MALT lymphoma, nodal marginal zone lymphoma, hairy cell leukemia, plasmacytoma and/or plasma cell myeloma, low grade/follicular lymphoma, intermediate grade/follicular NHL, mantle cell lymphoma, follicle center lymphoma (follicular lymphoma), intermediate grade diffuse NHL, diffuse large B-cell lymphoma, relapsed/refractory diffuse large B-cell lymphoma, aggressive NHL (including aggressive front-line NHL and aggressive relapsed NHL), NHL relapsing after or refractory to autologous stem cell transplantation, primary mediastinal large B-cell lymphoma, primary effusion lymphoma, high grade immunoblastic NHL, high grade lymphoblastic NHL, high grade small non-cleaved cell NHL, bulky disease NHL, Burkitt's lymphoma, precursor (peripheral) large granular lymphocytic leukemia, mycosis fungoides and/or Sezary syndrome, skin (cutaneous) lymphomas, anaplastic large cell lymphoma, angiocentric lymphoma.

A "disorder" is any condition that would benefit from treatment with a substance/molecule or method of the disclosure. This includes chronic and acute disorders or diseases including those pathological conditions which predispose the mammal to the disorder in question. Non-limiting examples of disorders to be treated herein include cancerous conditions such as malignant and benign tumors; non-leukemias and lymphoid malignancies; neuronal, glial, astrocytal, hypothalamic and other glandular, macrophagal, epithelial, stromal and blastocoelic disorders; and inflammatory, immunologic and other angiogenesis-related disorders. Disorders further include cancerous conditions such as B cell proliferative disorders and/or B cell tumors, e.g., lymphoma, non-Hodgkin's lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma.

The terms "cell proliferative disorder" and "proliferative disorder" refer to disorders that are associated with some degree of abnormal cell proliferation. In one embodiment, the proliferative disorder is cancer. In some embodiments, the cancer is a B cell proliferative disorder.

"Tumor," as used herein, refers to all neoplastic cell growth and proliferation, whether malignant or benign, and all pre-cancerous and cancerous cells and tissues.

"Treating" or "treatment" or "alleviation" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for a CD79b polypeptide-expressing cancer if, after receiving a therapeutic amount of an anti-CD79b antibody according to the methods of the present disclosure, the patient shows observable and/or measurable reduction in or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life issues. To the extent the anti-CD79b antibody may prevent growth and/or kill existing cancer cells, it may be cytostatic and/or cytotoxic. Reduction of these signs or symptoms may also be felt by the patient.

The above parameters for assessing successful treatment and improvement in the disease are readily measurable by routine procedures familiar to a physician. For cancer therapy, efficacy can be measured, for example, by assessing the time to disease progression (TTP) and/or determining the response rate (RR). Metastasis can be determined by staging tests and by bone scan and tests for calcium level and other enzymes to determine spread to the bone. CT scans can also be done to look for spread to the pelvis and lymph nodes in the area. Chest X-rays and measurement of liver enzyme levels by known methods are used to look for metastasis to the lungs and liver, respectively. Other routine methods for monitoring the disease include transrectal ultrasonography (TRUS) and transrectal needle biopsy (TRNB).

For bladder cancer, which is a more localized cancer, methods to determine progress of disease include urinary cytologic evaluation by cystoscopy, monitoring for presence of blood in the urine, visualization of the urothelial tract by sonography or an intravenous pyelogram, computed tomography (CT) and magnetic resonance imaging (MRI). The presence of distant metastases can be assessed by CT of the abdomen, chest x-rays, or radionuclide imaging of the skeleton.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

An "individual", "subject," or "patient" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, a mammal is a human.

Administration "in combination with" one or more further therapeutic agents includes simultaneous (concurrent) and consecutive administration in any order.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

The term "pharmaceutical composition" or "pharmaceutical formulation" refers to a preparation of an anti-CD79b immunoconjugate which is in such form as to permit the biological activity of the active ingredient to be effective, and which contains no additional components which are unacceptably toxic to a subject to which the formulation would be administered. Such formulations are sterile. "Pharmaceutically acceptable" excipients (vehicles, additives) are those which can reasonably be administered to a subject mammal to provide an effective dose of the active ingredient employed.

A "sterile" formulation is aseptic or free or essentially free from all living microorganisms and their spores.

An "effective amount" of an anti-CD79b immunoconjugate as disclosed herein is an amount sufficient to carry out a specifically stated purpose. An "effective amount" may be determined empirically and in a routine manner, in relation to the stated purpose.

The term "therapeutically effective amount" refers to an amount of an anti-CD79b immunoconjugate effective to "treat" a disease or disorder in a subject or mammal. In the case of cancer, the therapeutically effective amount of the immunoconjugate may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See the definition herein of "treating". To the extent the immunoconjugate may prevent growth and/or kill existing cancer cells, it may be cytostatic and/or cytotoxic. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

A "growth inhibitory amount" of an anti-CD79b immunoconjugate is an amount capable of inhibiting the growth of a cell, especially tumor, e.g., cancer cell, either in vitro or in vivo. A "growth inhibitory amount" of an anti-CD79b immunoconjugate for purposes of inhibiting neoplastic cell growth may be determined empirically and in a routine manner.

A "cytotoxic amount" of an anti-CD79b immunoconjugate is an amount capable of causing the destruction of a cell, especially tumor, e.g., cancer cell, either in vitro or in vivo. A "cytotoxic amount" of an anti-CD79b antibody for purposes of inhibiting neoplastic cell growth may be determined empirically and in a routine manner.

A "CD79b-expressing cell" is a cell which expresses an endogenous or transfected CD79b polypeptide either on the cell surface or in a secreted form. A "CD79b-expressing cancer" is a cancer comprising cells that have a CD79b polypeptide present on the cell surface or that produce and secrete a CD79b polypeptide. A "CD79b-expressing cancer" optionally produces sufficient levels of CD79b polypeptide on the surface of cells thereof, such that an anti-CD79b antibody can bind thereto and have a therapeutic effect with respect to the cancer. In another embodiment, a "CD79b-expressing cancer" optionally produces and secretes sufficient levels of CD79b polypeptide, such that an anti-CD79b antibody antagonist can bind thereto and have a therapeutic effect with respect to the cancer. With regard to the latter, the antagonist may be an antisense oligonucleotide which reduces, inhibits or prevents production and secretion of the secreted CD79b polypeptide by tumor cells. A cancer which "overexpresses" a CD79b polypeptide is one which has higher levels of CD79b polypeptide at the cell surface thereof, or produces and secretes, compared to a noncancerous cell of the same tissue type. Such overexpression may be caused by gene amplification or by increased transcription or translation. CD79b polypeptide overexpression may be determined in a detection or prognostic assay by evaluating increased levels of the CD79b protein present on the surface of a cell, or secreted by the cell (e.g., via an immunohistochemistry assay using anti-CD79b antibodies prepared against an isolated CD79b polypeptide which may be prepared using recombinant DNA technology from an isolated nucleic acid encoding the CD79b polypeptide; FACS analysis, etc.). Alternatively, or additionally, one may measure levels of CD79b polypeptide-encoding nucleic acid or mRNA in the cell, e.g., via fluorescent in situ hybridization using a nucleic acid based probe corresponding to a CD79b-encoding nucleic acid or the complement thereof; (FISH; see WO98/45479 published October, 1998), Southern blotting, Northern blotting, or polymerase chain reaction (PCR) techniques, such as real time quantitative PCR (RT-PCR). One may also study CD79b polypeptide overexpression by measuring shed antigen in a biological fluid such as serum, e.g., using antibody-based assays (see also, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al., J. Immunol. Methods 132: 73-80 (1990)). Aside from the above assays, various in vivo assays are available to the skilled practitioner. For example, one may expose cells within the body of the patient to an antibody which is optionally labeled with a detectable label, e.g., a radioactive isotope, and binding of the antibody to cells in the patient can be evaluated, e.g., by external scanning for radioactivity or by analyzing a biopsy taken from a patient previously exposed to the antibody.

The term "cytotoxic agent" as used herein refers to a drug molecule that inhibits or prevents the function of cells and/or causes destruction of cells. The term is intended to include toxins such as small molecule toxins or enzymatically active toxins of bacterial, fungal, plant or animal origin, including fragments and/or variants thereof capable of having a detrimental effect on the growth or proliferation of a cell. In one embodiment, the cytotoxic agent is mono-methyl auristatin E (MMAE).

A "lyophilized" composition as used herein refers to a liquid composition that has been subjected to freeze-drying via the process of lyophilization, resulting in a "cake". In certain embodiments, the lyophilized cake is stable under storage conditions (5° C.±3° C. and protected from light) with no significant changes in the cake structure, color, appearance, or moisture content. In a specific embodiment, the lyophilized cake is smooth without indentations. In certain embodiments of the present disclosure, the lyophilized composition is stable for about 60 months. In certain embodiments of the present disclosure, the lyophilized composition is stable for about 48 months.

A "stable" formulation is one in which the immunoconjugate therein essentially retains its physical stability and/or chemical stability and/or biological activity upon storage. Preferably, the formulation essentially retains its physical and chemical stability, as well as its biological activity upon storage. The storage period is generally selected based on the intended shelf-life of the formulation. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993), for example. Stability can be measured at a selected temperature for a selected time period. Stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography, image capillary isoelectric focusing (icIEF) or capillary zone electrophoresis; amino-terminal or carboxy-terminal sequence analysis; mass spectrometric analysis; SDS-PAGE analysis to compare reduced and intact antibody; peptide map (for example tryptic or LYS-C) analysis; evaluating biological activity or antigen binding function of the antibody; etc. Instability may involve any one or more of: aggregation, deamidation (e.g., Asn deamidation), oxidation (e.g., Met oxidation), isomerization (e.g., Asp isomeriation), clipping/hydrolysis/fragmentation (e.g., hinge region fragmentation), succinimide formation, unpaired cysteine(s), N-terminal extension, C-terminal processing, glycosylation differences, etc.

An immunoconjugate "retains its physical stability" in a pharmaceutical formulation if it shows no signs or very little of aggregation, precipitation and/or denaturation upon visual examination of color and/or clarity, or as measured by UV light scattering or by size exclusion chromatography.

An immunoconjugate "retains its chemical stability" in a pharmaceutical formulation, if the chemical stability at a given time is such that the immunoconjugate is considered to still retain its biological activity as defined below. Chemical stability can be assessed by detecting and quantifying chemically altered forms of the protein moiety of the immunoconjugate (e.g., the antibody). Chemical alteration may involve size modification (e.g. clipping) which can be evaluated using size exclusion chromatography, SDS-PAGE and/or matrix-assisted laser desorption ionization/time-of-flight mass spectrometry (MALDI/TOF MS), for example. Other types of chemical alteration include charge alteration (e.g. occurring as a result of deamidation) which can be evaluated by ion-exchange chromatography or icIEF, for example. Additionally or alternatively, chemical stability of an immunoconjugate can be assessed by detecting and quantifying chemically altered forms of the drug moiety of the immunoconjugate. Additionally or alternatively, chemical stability of an immunoconjugate can be assessed by measuring drug: antibody ratio (DAR), e.g., via hydrophobic interaction chromatography (HIC) to determine DAR distribution in a composition comprising the immunoconjugate.

An antibody of an immunoconjugate "retains its biological activity" in a pharmaceutical formulation, if the biological activity of the protein moiety of the immunoconjugate (e.g., the antibody, such as an anti-CD79b antibody) at a given time is at least about 60% (within the errors of the assay) of the biological activity exhibited at the time the pharmaceutical formulation comprising the immunoconjugate was prepared as determined in an assay (e.g., an antigen binding assay).

A "deamidated" monoclonal antibody herein is one in which one or more asparagine residue thereof has been derivitized, e.g. to an aspartic acid or an iso-aspartic acid.

An "oxidized" monoclonal antibody herein is one in which one or more tryptophan residue and/or one or more methionine thereof has been oxidized.

A "glycated" monoclonal antibody herein is one in which one or more lysine residue thereof has been glycated.

An antibody which is "susceptible to deamidation" is one comprising one or more residue, which has been found to be prone to deamidate.

An antibody which is "susceptible to oxidation" is one comprising one or more residue, which has been found to be prone to oxidize.

An antibody which is "susceptible to aggregation" is one which has been found to aggregate with other antibody molecule(s), especially upon freezing and/or agitation.

An antibody which is "susceptible to fragmentation" is one which has been found to be cleaved into two or more fragments, for example at a hinge region thereof.

By "reducing deamidation, oxidation, aggregation, or fragmentation" is intended preventing or decreasing the amount of deamidation, oxidation, aggregation, or fragmentation relative to the monoclonal antibody formulated in a different formulation.

The antibody which is formulated is preferably essentially pure and desirably essentially homogeneous (e.g., free from contaminating proteins etc.). "Essentially pure" antibody means a composition comprising at least about 90% by weight of the antibody, based on total weight of proteins in the composition, preferably at least about 95% by weight. "Essentially homogeneous" antibody means a composition comprising at least about 99% by weight of antibody, based on total weight of proteins in the composition.

By "isotonic" is meant that the formulation of interest has essentially the same osmotic pressure as human blood. Isotonic formulations generally have an osmotic pressure from about 250 to 350 mOsm. Isotonicity can be measured using a vapor pressure or ice-freezing type osmometer, for example.

As used herein, "buffering agent" refers to a buffered solution that resists changes in pH by the action of its acid-base conjugate components. Non-limiting examples of buffering agents herein include histidine, sodium phosphate, and sodium succinate. The buffering agent of this disclosure preferably has a pH in the range from about 4.5 to about 7.0, preferably from about 5.0 to about 6.0. In one embodiment the buffering agent has a pH 5.0, 5.1, 5.2, 5.3, 5.4, 5.5, 5.6, 5.7, 5.8, 5.9, or 6.0. In an exemplary embodiment, the buffering agent has a pH of 5.3. For example, sodium succinate is an example of a buffering agent that will control the pH in this range.

As used herein, a "surfactant" refers to a surface-active agent, preferably a nonionic surfactant. Examples of surfactants herein include polysorbate (for example, polysorbate 20 and, polysorbate 80); poloxamer (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.); polyethyl glycol, polypropyl glycol, and copolymers of ethylene and propylene glycol (e.g. Pluronics, PF68 etc); etc. In one embodiment, the surfactant herein is polysorbate 20. In another embodiment, the surfactant herein is polysorbate 80.

As used herein, a "sugar" refers to soluble carbohydrates. Non-limiting examples of sugars include glucose, fructose, sucrose, trehalose, arginin, glycerin, prolin, dextran, and sugar alcohols, such as glycerol, mannitol, and sorbitol.

II. Pharmaceutical Compositions

In one aspect, the disclosure provides a pharmaceutical composition including an anti-CD79b immunoconjugate and a surfactant, wherein the surfactant is at a concentration of at least 0.06% w/v (i.e., 0.6 mg/ml), and wherein the anti-CD79b immunoconjugate comprises the formula:

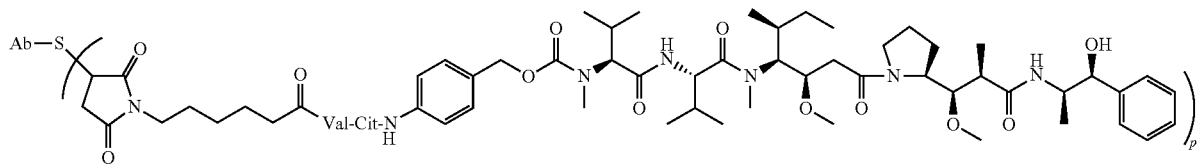

wherein:
Ab is an anti-CD79b antibody, wherein the anti-CD79b antibody comprises a heavy chain and a light chain, wherein the light chain comprises (a) an HVR-L1 sequence of KASQSVDYEGDSFLN (SEQ ID NO: 1); (b) an HVR-L2 sequence of AASNLES (SEQ ID NO: 2); and (c) an HVR-L3 sequence of QQSNEDPLT (SEQ ID NO: 3); wherein the heavy chain comprises (a) an HVR-H1 sequence of GYTFSSYWIE (SEQ ID NO: 4); (b) an HVR-H2 sequence of GEILPGGGDTNYNEIFKG (SEQ ID NO: 5); and (c) an HVR-H3 sequence of TRRVPIRLDY (SEQ ID NO: 6); Val is valine; Cit is citrulline; and p is a value from about 1 to about 8 (e.g., between about 2 and about 5, such as about 3.5).

In some embodiments, the composition of the present disclosure is lyophilized. In some embodiments, a composition disclosed herein is a reconstituted composition, i.e., a composition that has been reconstituted from a lyophilized cake. In some embodiments, provided is a 20-ml glass vial (such as a sealed vial) that contains a pharmaceutical composition (e.g., a lyophilized composition or a reconstituted composition) described herein.

A. Immunoconjugates

The disclosure pertains to immunoconjugates (interchangeably referred to as "antibody-drug conjugates," or "ADCs") comprising an antibody conjugated to a small molecule toxin, such as monomethylauristatin (MMAE) (synthetic analog of dolastatin). The present disclosure provides anti-CD79b immunoconjugates of the formula Ab-(L-D)p, wherein Ab is an anti-CD79b antibody, wherein the anti-CD79b antibody comprises a heavy chain and a light chain, wherein the light chain comprises (a) an HVR-L1 sequence of KASQSVDYEGDSFLN (SEQ ID NO: 1); (b) an HVR-L2 sequence of AASNLES (SEQ ID NO: 2); and (c) an HVR-L3 sequence of QQSNEDPLT (SEQ ID NO: 3); wherein the heavy chain comprises (a) an HVR-H1 sequence of GYTFSSYWIE (SEQ ID NO: 4); (b) an HVR-H2 sequence of GEILPGGGDTNYNEIFKG (SEQ ID NO: 5); and (c) an HVR-H3 sequence of TRRVPIRLDY (SEQ ID NO: 6); L is a linker comprising 6-maleimidocaproyl-valine-citrulline-p-aminobenzyloxycarbonyl (MC-val-cit-PAB); D is MMAE; and p is a value from about 1 to about 8 (such as between about 2 and about 5, e.g., about 3.5); and wherein the anti-CD79b immunoconjugate has the structure:

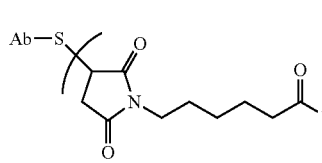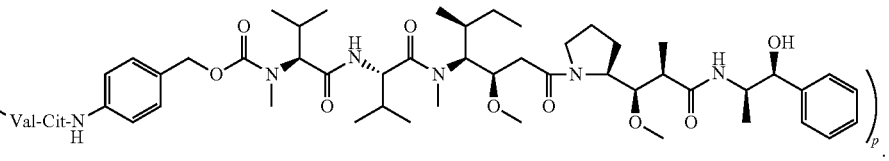

The anti-CD79b immunoconjugate of the present disclosure may be referred to as anti-CD79b-MC-val-cit-MMAE, anti-CD79b-MC-vc-MMAE, or anti-CD79b-vc-MMAE. Polatuzumab vedotin is an example of the anti-CD79b immunoconjugate of the present disclosure. Polatuzumab vedotin has the CAS Registration Number 1313206-42-6, the IUPHAR/BPS Number 8404, and the KEGG Number D10761. The terms "polatuzumab vedotin," "DCDS4501A," and "RG7596" encompass all corresponding immunoconjugates that fulfill the requirements necessary for obtaining a marketing authorization as an identical or biosimilar product in a country or territory selected from the group of countries consisting of the USA, Europe and Japan.

In some embodiments, the anti-CD79b immunoconjugate is at a concentration in the pharmaceutical composition of about 5 mg/ml to about 60 mg/ml, about 10 mg/ml to about 50 mg/ml, about 10 mg/ml to about 40 mg/ml, about 10 mg/ml to about 30 mg/ml, or about 10 mg/ml to about 20 mg/ml. In a specific embodiment, the anti-CD79b immunoconjugate is at a concentration in the pharmaceutical composition of about 5 mg/ml, about 6 mg/ml, about 7 mg/ml, about 8 mg/ml, about 9 mg/ml, about 10 mg/ml, about 11 mg/ml, about 12 mg/ml, about 13 mg/ml, about 14 mg/ml, about 15 mg/ml, about 16 mg/ml, about 17 mg/ml, about 18 mg/ml, about 19 mg/ml, about 20 mg/ml, about 25 mg/ml, about 30 mg/ml, about 35 mg/ml, about 40 mg/ml, about 45 mg/ml, about 50 mg/ml, about 55 mg/ml, or about 60 mg/ml.

In some embodiments of any of the embodiments provided herein, "about" a value or parameter encompasses an error range of any one of ±10%, ±9%, ±8%, ±7%, ±6%, ±5%, ±4%, ±3%, ±2%, or ±1% of the stated value or parameter, including any range in between these values.

In some embodiments, the anti-CD79b immunoconjugate is at a concentration in the pharmaceutical composition of about 10 mg/ml to about 20 mg/ml. In an exemplary embodiment, the anti-CD79b immunoconjugate is at a concentration in the pharmaceutical composition of about 10 mg/ml. In another exemplary embodiment, the anti-CD79b immunoconjugate is at a concentration in the pharmaceutical composition of about 20 mg/ml.

In some embodiments, the anti-CD79b immunoconjugate is at a concentration in the pharmaceutical composition of 5 mg/ml to 60 mg/ml, 10 mg/ml to 50 mg/ml, 10 mg/ml to 40 mg/ml, 10 mg/ml to 30 mg/ml, or 10 mg/ml to 20 mg/ml. In a specific embodiment, the anti-CD79b immunoconjugate is at a concentration in the pharmaceutical composition of 5 mg/ml, 6 mg/ml, 7 mg/ml, 8 mg/ml, 9 mg/ml, mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 25 mg/ml, 30 mg/ml, 35 mg/ml, 40 mg/ml, 45 mg/ml, 50 mg/ml, 55 mg/ml, or 60 mg/ml.

In some embodiments, the anti-CD79b immunoconjugate is at a concentration in the pharmaceutical composition of 10 mg/ml to 20 mg/ml. In an exemplary embodiment, the anti-CD79b immunoconjugate is at a concentration in the pharmaceutical composition of 10 mg/ml. In another exemplary embodiment, the anti-CD79b immunoconjugate is at a concentration in the pharmaceutical composition of 20 mg/ml.

As contemplated herein, the anti-CD79b immunoconjugate is of Formula I, as shown below, wherein an anti-CD79b antibody or fragment thereof (Ab) is conjugated (i.e., covalently attached) to an MMAE drug moiety (D) through a linker (L).

$$Ab\text{-}(L\text{-}D)_p \qquad\qquad I$$

In Formula I, p is the average number of drug moieties per antibody, which can range, e.g., from about 1 to about 20 drug moieties per antibody, and in certain embodiments, from 1 to about 8 drug moieties per antibody. The disclosure includes a composition comprising a mixture of antibody-drug compounds of Formula I where the average drug loading per antibody is about 2 to about 5, or about 3 to about 4, e.g., 3.5.

1. Anti-CD79b Antibody

The present disclosure provides immunoconjugates comprising an anti-CD79b antibody or functional fragments thereof.

In one aspect, the disclosure provides an anti-CD79b antibody which binds, preferably specifically, to CD79b. Optionally, the antibody is a monoclonal antibody, antibody fragment, including Fab, Fab', F(ab')2, and Fv fragment, diabody, single domain antibody, chimeric antibody, humanized antibody, single-chain antibody or antibody that competitively inhibits the binding of an anti-CD79b polypeptide antibody to its respective antigenic epitope. Antibodies of the present disclosure may optionally be produced in CHO cells or bacterial cells and preferably induce death of a cell to which they bind.

The present disclosure provides an anti-CD79b immunoconjugate including a humanized anti-CD79b antibody wherein the monovalent affinity of the antibody to CD79b (e.g. affinity of the antibody as a Fab fragment to CD79b) is substantially the same as the monovalent affinity of a murine antibody (e.g. affinity of the murine antibody as a Fab fragment to CD79b) or a chimeric antibody (e.g. affinity of the chimeric antibody as a Fab fragment to CD79b).

In one embodiment, the disclosure provides an anti-CD79b immunoconjugate including a humanized anti-CD79b antibody wherein the affinity of the antibody in its bivalent form to CD79b (e.g., affinity of the antibody as an IgG to CD79b) is 0.3 nM or better. In another embodiment, the disclosure provides a humanized anti-CD79b antibody wherein the affinity of the antibody in its bivalent form to CD79b (e.g., affinity of the antibody as an IgG to CD79b) is 0.5 nM. In a further embodiment, the disclosure provides a humanized anti-CD79b antibody wherein the affinity of the antibody in its bivalent form to CD79b (e.g., affinity of the antibody as an IgG to CD79b) is 0.5 nM+/−0.1. In another embodiment, the disclosure provides a humanized anti-CD79b antibody wherein the affinity of the antibody in its bivalent form to CD79b (e.g., affinity of the antibody as an IgG to CD79b) is between 0.3 nM and 0.7 nM. In another embodiment, the disclosure provides a humanized anti-CD79b antibody wherein the affinity of the antibody in its bivalent form to CD79b (e.g., affinity of the antibody as an IgG to CD79b) is between 0.4 nM and 0.6 nM. In another embodiment, the disclosure provides a humanized anti-CD79b antibody wherein the affinity of the antibody in its bivalent form to CD79b (e.g., affinity of the antibody as an IgG to CD79b) is between 0.5 nM and 0.55 nM.

As is well-established in the art, binding affinity of a ligand to its receptor can be determined using any of a variety of assays, and expressed in terms of a variety of quantitative values. Accordingly, in one embodiment, the binding affinity is expressed as Kd values and reflects intrinsic binding affinity (e.g., with minimized avidity effects). Generally and preferably, binding affinity is measured in vitro, whether in a cell-free or cell-associated setting. As described in greater detail herein, fold difference in binding affinity can be quantified in terms of the ratio of the monovalent binding affinity value of a humanized antibody (e.g., in Fab form) and the monovalent binding affinity value of a reference/comparator antibody (e.g., in Fab form) (e.g., a murine antibody having donor hypervariable region sequences), wherein the binding affinity values are determined under similar assay conditions. Thus, in one embodiment, the fold difference in binding affinity is determined as the ratio of the Kd values of the humanized antibody in Fab form and said reference/comparator Fab antibody. For example, in one embodiment, if an antibody of the disclosure (A) has an affinity that is "3-fold lower" than the affinity of a reference antibody (M), then if the Kd value for A is 3×, the Kd value of M would be 1×, and the ratio of Kd of A to Kd of M would be 3:1. Conversely, in one embodiment, if an antibody of the disclosure (C) has an affinity that is "3-fold greater" than the affinity of a reference antibody (R), then if the Kd value for C is 1×, the Kd value of R would be 3×, and the ratio of Kd of C to Kd of R would be 1:3. Any of a number of assays known in the art, including those described herein, can be used to obtain binding affinity measurements, including, for example, Biacore, radioimmunoassay (RIA) and ELISA.

The provided anti-CD79b antibody comprises a heavy chain and a light chain, wherein the light chain comprises (a) an HVR-L1 sequence of KASQSVDYEGDSFLN (SEQ ID NO: 1); (b) an HVR-L2 sequence of AASNLES (SEQ ID NO: 2); and (c) an HVR-L3 sequence of QQSNEDPLT (SEQ ID NO: 3); wherein the heavy chain comprises (a) an HVR-H1 sequence of GYTFSSYWIE (SEQ ID NO: 4); (b) an HVR-H2 sequence of GEILPGGGDTNYNEIFKG (SEQ ID NO: 5); and (c) an HVR-H3 sequence of TRRVPIRLDY (SEQ ID NO: 6).

In some embodiments of the present disclosure, the anti-CD79b antibody comprises a heavy chain variable domain (VH) comprising the amino acid sequence of:

(SEQ ID NO: 7)
EVQLVESGGGLVQPGGSLRLSCAASGYTFSSYWIEWVRQAPGKGLEWIGE

ILPGGGDTNYNEIFKGRATFSADTSKNTAYLQMNSLRAEDTAVYYCTRRV

PIRLDYWGQGTLVTVSS and a light chain variable domain (VL) comprising the amino acid sequence of:

(SEQ ID NO: 8)
DIQLTQSPSSLSASVGDRVTITCKASQSVDYEGDSFLNWYQQKPGKAPK

LLIYAASNLESGVPSRFSGSGSGTDFTLTISSLQPEDFATYYCQQSNED

PLTFGQGTKVEIKR.

In some embodiments, the heavy chain comprises the amino acid sequence of:

(SEQ ID NO: 9)
EVQLVESGGGLVQPGGSLRLSCAASGYTFSSYWIEWVRQAPGKGLEWIG

EILPGGGDTNYNEIFKGRATFSADTSKNTAYLQMNSLRAEDTAVYYCTR

RVPIRLDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQP

REPQVYTLPPSREEMTKNQVSLTCLVKGFYPSDIAVEWESNGQPENNYK

TTPPVLDSDGSFFLYSKLTVDKSRWQQGNVFSCSVMHEALHNHYTQKSL

SLSPG and the light chain comprises the amino acid sequence of (SEQ ID NO: 10)
DIQLTQSPSSLSASVGDRVTITCKASQSVDYEGDSFLNWYQQKPGKAPK

LLIYAASNLESGVPSRFSGSGSGTDFTLTISSLQPEDFATYYCQQSNED

PLTFGQGTKVEIKRTVAAPSVFIFPPSDEQLKSGTASVVCLLNNFYPRE

AKVQWKVDNALQSGNSQESVTEQDSKDSTYSLSSTLTLSKADYEKHKVY

ACEVTHQGLSSPVTKSFNRGEC.

2. Linker

The present disclosure provides a linker that includes several components, including 6-maleimidocaproyl ("MC"), valine-citrulline ("val-cit" or "vc"), and p-aminobenzyloxy-carbonyl (a "PAB"). Such linker components are known in the art and are briefly described below.

As used herein, a linker is of Formula II:

$$-A_a-W_w-Y_y- \quad\quad II$$

wherein A is a stretcher unit, and a is an integer from 0 to 1; W is an amino acid unit, and w is an integer from 0 to 12; Y is a spacer unit, and y is 0, 1, or 2. A "stretcher unit" links an antibody to another linker component. The stretcher unit provided herein, MC, is shown below (wherein the wavy line indicates sites of covalent attachment to an antibody):

An amino acid unit allows for cleavage of the linker by a protease, thereby facilitating release of the drug from the immunoconjugate upon exposure to intracellular proteases, such as lysosomal enzymes. See, e.g., Doronina et al. (2003) Nat. Biotechnol. 21:778-784. An amino acid unit may comprise amino acid residues that occur naturally, as well as minor amino acids and non-naturally occurring amino acid analogs, such as citrulline. Amino acid units can be designed and optimized in their selectivity for enzymatic cleavage by a particular enzyme, for example, a tumor-associated protease, cathepsin B, C and D, or a plasmin protease. The amino acid unit provided herein is a valine-citrulline (vc or val-cit) dipeptide.

As used herein, a "spacer" unit is self-immolative and links the antibody to a drug moiety by way of a stretcher unit and an amino acid unit. A "self-immolative" spacer unit allows for release of the drug moiety without a separate hydrolysis step as a result of an amide bond, and a carbamate, methylcarbamate, or carbonate made between the benzyl alcohol and a cytotoxic agent. See, e.g., Hamann et al. (2005) *Expert Opin. Ther. Patents* (2005) 15:1087-1103. The spacer unit provided herein is p-aminobenzyloxycarbonyl (PAB).

Linker components, including stretcher, spacer, and amino acid units, may be synthesized by methods known in the art, such as those described in US 2005-0238649A1

The linker of the present disclosure is MC-val-cit-PAB as shown below.

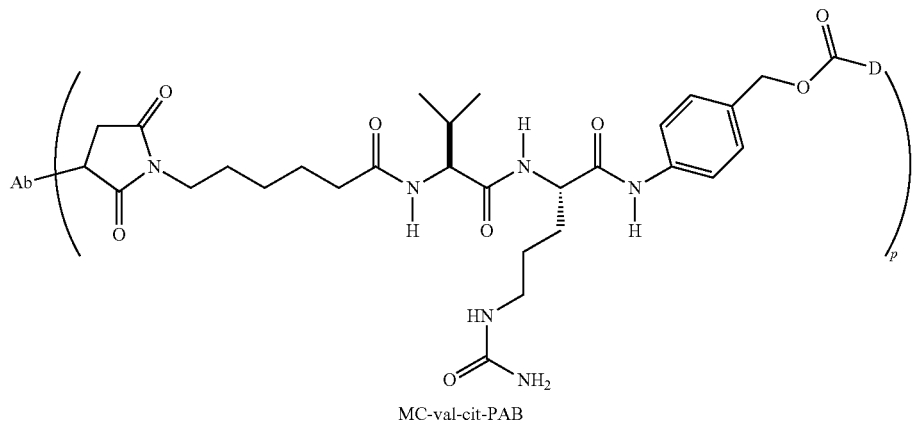

MC-val-cit-PAB

3. Monomethylauristatin (MMAE)

The immunoconjugate of the present disclosure includes an anti-CD79b antibody or fragment thereof conjugated to an auristatin, a synthetic analog of dolastatin (U.S. Pat. Nos. 5,635,483; 5,780,588). Dolastatins and auristatins have been shown to interfere with microtubule dynamics, GTP hydrolysis, and nuclear and cellular division (Woyke et al (2001) *Antimicrob. Agents and Chemother.* 45(12):3580-3584) and have anticancer (U.S. Pat. No. 5,663,149) and antifungal activity (Pettit et al (1998) *Antimicrob. Agents Chemother.* 42:2961-2965). The auristatin drug moiety may be attached to the antibody through the N (amino) terminus or the C (carboxyl) terminus of the peptidic drug moiety (WO 02/088172). The auristatin of the present disclosure is the synthetic, non-charged, N-terminus linked monomethylauristatin (MMAE) pentapeptide as shown below.

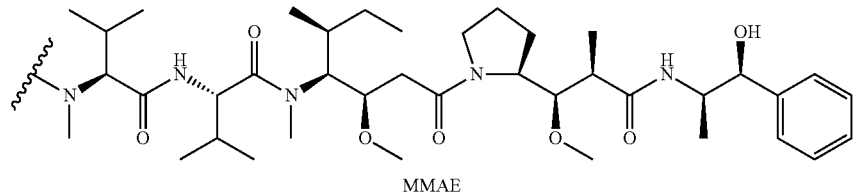 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

MMAE

The anti-CD79b immunoconjugate of Formula I comprising an anti-CD79b antibody or fragment thereof, a linker with and various linker components and MMAE is shown below with the following abbreviations (wherein "Ab" is an anti-CD79b antibody or fragment thereof; p is 1 to about 8 (e.g., between about 2 and about 5, such as about 3.5), "Val-Cit" or "vc" is a valine-citrulline dipeptide; and "S" is a sulfur atom.

indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

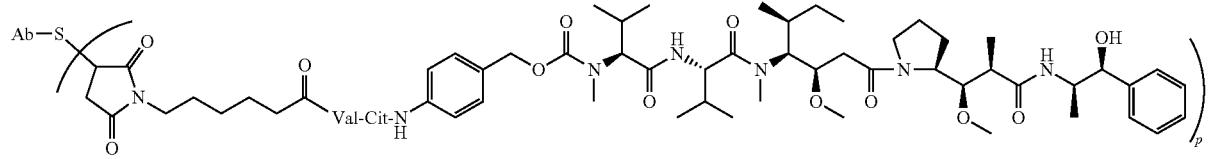

It will be noted that in certain of the structural descriptions of sulfur linked immunoconjugate herein the antibody is represented as "Ab-S" merely to indicate the sulfur link feature and not to indicate that a particular sulfur atom bears multiple linker-drug moieties. The left parenthesis of the following structure may also be placed to the left of the sulfur atom, between Ab and S, which would be an equivalent description of the immunoconjugate of the disclosure described herein.

4. Drug Loading

Drug loading is represented by p, the average number of drug moieties per antibody in a molecule of Formula I. Drug loading may range from 1 to 20 drug moieties (D) per antibody. ADCs of Formula I include collections of antibodies conjugated with a range of drug moieties, from 1 to 20. The average number of drug moieties per antibody in preparations of ADC from conjugation reactions may be characterized by conventional means such as mass spectroscopy, ELISA assay, and HPLC. The quantitative distribution of ADC in terms of p may also be determined. In some instances, separation, purification, and characterization of homogeneous ADC where p is a certain value from ADC with other drug loadings may be achieved by means such as reverse phase HPLC or electrophoresis. Pharmaceutical formulations of Formula I antibody-drug conjugates may thus be a heterogeneous mixture of such conjugates with antibodies linked to 1, 2, 3, 4, or more drug moieties.

For some antibody-drug conjugates, p may be limited by the number of attachment sites on the antibody. For example, where the attachment is a cysteine thiol, as in the embodiments provided herein, an antibody may have only one or several cysteine thiol groups, or may have only one or several sufficiently reactive thiol groups through which a linker may be attached. In certain embodiments, higher drug loading, e.g. p>5, may cause aggregation, insolubility, toxicity, or loss of cellular permeability of certain antibody-drug conjugates. In certain embodiments, the drug loading for an ADC of the disclosure ranges from 1 to about 8; from about 2 to about 6; from about 3 to about 5, or about 3.5. Indeed, it has been shown that for certain ADCs, the optimal ratio of drug moieties per antibody may be less than 8, and may be about 2 to about 5. See US 2005-0238649 A1.

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety;

The loading (drug/antibody ratio) of an ADC may be controlled in different ways, e.g., by: (i) limiting the molar excess of drug-linker intermediate or linker reagent relative to antibody, (ii) limiting the conjugation reaction time or temperature, and (iii) partial or limiting reductive conditions for cysteine thiol modification.

It is to be understood that where more than one nucleophilic group reacts with a drug-linker intermediate or linker reagent followed by drug moiety reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography (see, e.g., McDonagh et al (2006) Prot. Engr. Design & Selection 19(7):299-307; Hamblett et al (2004) Clin. Cancer Res. 10:7063-7070; Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous ADC with a single loading value may be isolated from the conjugation mixture by electrophoresis or chromatography.

5. Exemplary Methods of Preparing Immunoconjugates

An ADC of Formula I may be prepared by several routes employing organic chemistry reactions, conditions, and reagents known to those skilled in the art, including: (1) reaction of a nucleophilic group of an antibody with a bivalent linker reagent to form Ab-L via a covalent bond, followed by reaction with a drug moiety D; and (2) reaction of a nucleophilic group of a drug moiety with a bivalent linker reagent, to form D-L, via a covalent bond, followed by reaction with a nucleophilic group of an antibody. Exemplary methods for preparing an ADC of Formula I via the latter route are described in US 2005-0238649 A1, which is expressly incorporated herein by reference.

Nucleophilic groups on antibodies include, but are not limited to: (i)N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol) or tricarbonylethylphosphine (TCEP), such that the antibody is fully or partially reduced. Each cysteine bridge will thus form, theoretically, two reactive thiol nucleophiles. Additional nucleophilic groups can be introduced into antibodies through modification of lysine residues, e.g., by reacting lysine residues with 2-iminothiolane (Traut's reagent), resulting in conversion of an amine into a thiol. Reactive thiol groups may be introduced into an antibody by introducing one, two, three, four, or more cysteine residues (e.g., by preparing variant antibodies comprising one or more non-native cysteine amino acid residues).

Antibody-drug conjugates of the disclosure may also be produced by reaction between an electrophilic group on an antibody, such as an aldehyde or ketone carbonyl group, with a nucleophilic group on a linker reagent or drug. Useful nucleophilic groups on a linker reagent include, but are not limited to, hydrazide, oxime, amino, hydrazine, thiosemicarbazone, hydrazine carboxylate, and arylhydrazide. In one embodiment, an antibody is modified to introduce electrophilic moieties that are capable of reacting with nucleophilic substituents on the linker reagent or drug. In another embodiment, the sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the antibody that can react with appropriate groups on the drug (Hermanson, Bioconjugate Techniques). In another embodiment, antibodies containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such an aldehyde can be reacted with a drug moiety or linker nucleophile.

Nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

The compounds of the disclosure expressly contemplate, but are not limited to, ADC prepared with the following cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A; see pages 467-498, 2003-2004 Applications Handbook and Catalog.

Immunoconjugates comprising an antibody and a cytotoxic agent may also be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

B. Surfactant

The present disclosure provides a composition including an anti-CD79b immunoconjugate and a surfactant. In certain embodiments, the surfactant is polysorbate (for example, polysorbate 20 and, polysorbate 80); poloxamer (e.g. poloxamer 188); N-octyl-β-D glucopyranoside (OG); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; the MONAQUAT™ series (Mona Industries, Inc., Paterson, N.J.); polyethyl glycol, polypropyl glycol, a copolymer of ethylene and propylene glycol, such as Pluronics, or PF68; or any combination thereof.

In some embodiments, the surfactant herein is non-ionic. In certain exemplary embodiments, the surfactant is chosen from the group consisting of polysorbate 20 (PS20), polysorbate 80 (PS80), poloxamer 188 (P188), N-octyl-β-D glucopyranoside (OG), and a combination thereof. In a specific embodiment, the surfactant is PS20. In another embodiment, the surfactant herein is PS80.

In certain embodiments, the surfactant (e.g., PS20) in the pharmaceutical composition is at a concentration of at least about 0.01% w/v (i.e., 0.1 mg/ml) and about 0.20% w/v (i.e., 2.0 mg/ml). In certain embodiments, the surfactant (e.g., PS20) in the pharmaceutical composition is at a concentration of at least about 0.01% w/v (i.e., 0.1 mg/ml), at least about 0.02% w/v (i.e., 0.2 mg/ml), at least about 0.03% w/v (i.e., 0.3 mg/ml), at least about 0.04% w/v (i.e., 0.4 mg/ml), at least about 0.05% w/v (i.e., 0.5 mg/ml), at least about 0.06% w/v (i.e., 0.6 mg/ml), at least about 0.07% w/v (i.e., 0.7 mg/ml), at least about 0.08% w/v (i.e., 0.8 mg/ml), at least about 0.09% w/v (i.e., 0.9 mg/ml), at least about 0.10% w/v (i.e., 1 mg/ml), at least about 0.11% w/v (i.e., 1.1 mg/ml), at least about 0.12% w/v (i.e., 1.2 mg/ml), at least about 0.13% w/v (i.e., 1.3 mg/ml), at least about 0.14% w/v (i.e., 1.4 mg/ml), at least about 0.15% w/v (i.e., 1.5 mg/ml), at least about 0.16% w/v (i.e., 1.6 mg/ml), at least about 0.17% w/v (i.e., 1.7 mg/ml), at least about 0.18% w/v (i.e., 1.8 mg/ml), at least about 0.19% w/v (i.e., 1.9 mg/ml), or at least about 0.20% w/v (i.e., 2.0 mg/ml), including any range in between these values. In a specific embodiment, the surfactant (e.g., PS20) in the pharmaceutical composition is at a concentration of at least about 0.06% w/v (i.e., 0.6 mg/ml). In another specific embodiment, the surfactant (e.g., PS20) in the pharmaceutical composition is at a concentration of at least about 0.12% w/v (i.e., 1.2 mg/ml). In some embodiments, the pharmaceutical composition is a liquid pharmaceutical composition. In some embodiments, the liquid pharmaceutical composition is stable for at least about any one of 4, 6, 8, 10, 12, 14, 16, 18, 20, 22, 24 hours upon storage at 30° C., or for at least about any one of 24, 48, or 72 hours upon storage at 2° C.-8° C.

In certain embodiments, the surfactant (e.g., PS20) in the pharmaceutical composition is at a concentration of at least about 0.01% w/v (i.e., 0.1 mg/ml) and about 0.20% w/v (i.e., 2.0 mg/ml). In certain embodiments, the surfactant (e.g., PS20) in the lyophilized pharmaceutical composition is at a concentration of at least 0.01% w/v, at least 0.02% w/v, at least 0.03% w/v, at least 0.04% w/v, at least 0.05% w/v, at least 0.06% w/v, at least 0.07% w/v, at least 0.08% w/v, at least 0.09% w/v, at least 0.10% w/v, at least 0.11% w/v, at least 0.12% w/v, at least 0.13% w/v, at least 0.14% w/v, at least 0.15% w/v, at least 0.16% w/v, at least 0.17% w/v, at least 0.18% w/v, at least 0.19% w/v, or at least 0.20% w/v, including any range in between these values. In a specific embodiment, the surfactant (e.g., PS20) in the lyophilized pharmaceutical composition is at a concentration of at least 0.06% w/v. In another specific embodiment, the surfactant (e.g., PS20) in the lyophilized pharmaceutical composition is at a concentration of at least 0.12% w/v. In some embodiments, the lyophilized pharmaceutical composition is a lyophilized cake. In some embodiments, the lyophilized pharmaceutical composition is contained in a glass vial.

In certain embodiments, the surfactant (e.g., PS20) in the liquid pharmaceutical composition is at a concentration of at least about 0.1 to about 2.0 mg/ml. In certain embodiments, the surfactant (e.g., PS20) in the liquid pharmaceutical composition is at a concentration of at least any one of about 0.1, 0.2, 0.3, 0.4, 0.5, 0.6, 0.7, 0.8, 0.9, 1.0, 1.2, 1.3, 1.4, 1.5, 1.6, 1.7, 1.8, 1.9 or 2.0 mg/ml, including any range in between these values. In a specific embodiment, the surfactant (e.g., PS20) in the liquid pharmaceutical composition is at a concentration of at least about 0.6% mg/ml. In another specific embodiment, the surfactant (e.g., PS20) in the liquid pharmaceutical composition is at a concentration of at least 1.2 mg/ml. In some embodiments, the liquid pharmaceutical composition is reconstituted (e.g., reconstituted using SWFI) from a lyophilized pharmaceutical composition (such as a lyophilized cake). In some embodiments, the liquid pharmaceutical composition is contained in a glass vial. In some embodiments, the liquid pharmaceutical composition is stable for at least about any one of 4, 6, 8, 10, 12, 14, 16, 18, 20, 22, 24 hours upon storage at 30° C., or for at least about any one of 24, 48, or 72 hours upon storage at 2° C.-8° C.

In an exemplary embodiment, the surfactant (e.g., PS20) in the lyophilized pharmaceutical composition is at a concentration of 0.06% w/v. In another exemplary embodiment, the surfactant (e.g., PS20) in the lyophilized pharmaceutical composition is at a concentration of 0.12% w/v. In some embodiments, the lyophilized pharmaceutical composition is a lyophilized cake. In some embodiments, the lyophilized pharmaceutical composition is contained in a glass vial.

In an exemplary embodiment, the surfactant (e.g., PS20) in the liquid pharmaceutical composition is at a concentration of 0.6 mg/ml. In another exemplary embodiment, the surfactant (e.g., PS20) in the liquid pharmaceutical composition is at a concentration of 1.2 mg/ml. In some embodiments, the liquid pharmaceutical composition is reconstituted (e.g., reconstituted using SWFI) from a lyophilized composition (such as a lyophilized cake). In some embodiments, the liquid pharmaceutical composition is contained in a glass vial. In some embodiments, the liquid pharmaceutical composition is stable for at least about any one of 4, 6, 8, 10, 12, 14, 16, 18, 20, 22, 24 hours upon storage at 30° C., or for at least about any one of 24, 48, or 72 hours upon storage at 2° C.-8° C. In some embodiments, the liquid pharmaceutical composition is stable for at least about any one of 4, 6, 8, 10, 12, 14, 16, 18, 20, 22, 24 hours upon storage at 30° C., or for at least about any one of 24, 48, or 72 hours upon storage at 2° C.-8° C.

In some embodiments, the anti-CD79b immunoconjugate in the pharmaceutical composition is at a concentration of 10 mg/ml and the surfactant in the pharmaceutical composition is at a concentration of at least 0.06% w/v (i.e., 0.6 mg/ml). In some embodiments, the anti-CD79b immunoconjugate in the pharmaceutical composition is at a concentration of 10 mg/ml and the surfactant (e.g., PS20) in the pharmaceutical composition is at a concentration of at least 0.12% w/v (i.e., 1.2 mg/ml). In some embodiments, the pharmaceutical composition is a reconstituted composition (e.g., reconstituted using SWFI from a lyophilized composition). In some embodiments, the pharmaceutical composition is contained in a glass vial. In some embodiments, the liquid pharmaceutical composition is stable for at least about any one of 4, 6, 8, 10, 12, 14, 16, 18, 20, 22, 24 hours upon storage at 30° C., or for at least about any one of 24, 48, or 72 hours upon storage at 2° C.-8° C.

In some embodiments, the anti-CD79b immunoconjugate in the pharmaceutical composition is at a concentration of 10 mg/ml and the surfactant (e.g., PS20) in the pharmaceutical composition is at a concentration of 0.06% w/v (i.e., 0.6 mg/ml). In some embodiments, the anti-CD79b immunoconjugate in the pharmaceutical composition is at a concentration of 10 mg/ml and the surfactant (e.g., PS20) in the pharmaceutical composition is at a concentration of 0.12% w/v (i.e., 1.2 mg/ml). In some embodiments, the pharmaceutical composition is a reconstituted composition (e.g., reconstituted using SWFI from a lyophilized composition). In some embodiments, the pharmaceutical composition is contained in a glass vial.

In some embodiments, the anti-CD79b immunoconjugate in the pharmaceutical composition is at a concentration of 20 mg/ml and the surfactant (e.g., PS20) in the pharmaceutical composition is at a concentration of at least 0.06% w/v (i.e., 0.6 mg/ml). In some embodiments, the anti-CD79b immunoconjugate in the pharmaceutical composition is at a concentration of 20 mg/ml and the surfactant (e.g., PS20) in the pharmaceutical composition is at a concentration of at least 0.12% w/v (i.e., 1.2 mg/ml). In some embodiments, the pharmaceutical composition is a reconstituted composition (e.g., reconstituted using SWFI from a lyophilized composition). In some embodiments, the pharmaceutical composition is contained in a glass vial.

In some embodiments, the anti-CD79b immunoconjugate in the pharmaceutical composition is at a concentration of 20 mg/ml and the surfactant (e.g., PS20) in the pharmaceutical composition is at a concentration of 0.06% w/v (i.e., 0.6 mg/ml). In some embodiments, the anti-CD79b immunoconjugate in the pharmaceutical composition is at a concentration of 20 mg/ml and the surfactant in the pharmaceutical composition is at a concentration of 0.12% w/v (i.e., 1.2 mg/ml). In some embodiments, the liquid pharmaceutical composition is stable for at least about any one of 4, 6, 8, 10, 12, 14, 16, 18, 20, 22, 24 hours upon storage at 30° C., or for at least about any one of 24, 48, or 72 hours upon storage at 2° C.-8° C.

In some embodiments, the pharmaceutical composition is a liquid composition suitable for intravenous administration. In some embodiments, the liquid composition suitable for administration comprises about 0.0432 and about 0.162 mg/ml surfactant (e.g., polysorbate 20). In some embodiments, the liquid composition comprises between about 0.72 mg/ml and about 2.7 mg/ml polatuzumab vedotin. In some embodiments, the liquid composition suitable for intravenous administration comprises about 0.72 mg/ml polatuzumab vedotin and about 0.0432 mg/ml polysorbate 20. In some embodiments, the liquid composition suitable for intravenous administration comprises about 2.7 mg/ml polatuzumab vedotin and about 0.162 mg/ml polysorbate 20.

C. Buffering Agent

According to the present disclosure, pharmaceutical compositions that include a buffering agent are provided. Without wishing to be bound by theory, the use of buffer maintains the pH of the pharmaceutical composition during manufacturing, storage and use of the composition. Non-limiting examples of buffering agents include histine, succinate, sodium succinate, sodium bicarbonate, calcium chloride, magnesium sulfate, monosodium phosphate, disodium phosphate, monopotassium phosphate, dipotassium phosphate, [tris(hydroxymethyl)methylamino]propanesulfonic acid (TAPS), 2-(Bis(2-hydroxyethyl)amino)acetic acid (Bicine), 2-Amino-2-(hydroxymethyl)propane-1,3-diol (Tris), N-(2-Hydroxy-1,1-bis(hydroxymethyl)ethyl)glycine (Tricine), 3-[[1,3-dihydroxy-2-(hydroxymethyl)propan-2-yl]amino]-2-hydroxypropane-1-sulfonic acid (TAPSO), 2-[4-(2-hydroxyethyl)piperazin-1-yl]ethanesulfonic acid (HEPES), 2-[[1,3-dihydroxy-2-(hydroxymethyl)propan-2-yl]amino]ethanesulfonic acid (TES), 1,4-Piperazinediethanesulfonic acid (PIPES), dimethylarsinic acid, 2-morpholin-4-ylethanesulfonic acid (MES), or phosphate buffered saline (PBS). Other suitable buffering agents may be acetic acid in a salt, citric acid in a salt, boric acid in a salt and phosphoric acid in a salt.

In exemplary embodiments of the present disclosure, the buffering agent is a histidine buffer or a succinate buffer. In a specific embodiment, the succinate buffer is a sodium succinate buffer.

In some embodiments, the buffering agent is at a concentration of about 10 mM to about 200 mM. In a specific embodiment, the buffering agent is at a concentration of about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 105 mM, about 110 mM, about 115 mM, about 120 mM, about 125 mM, about 130 mM, about 135 mM, about 140 mM, about 145 mM, about 150 mM, about 155 mM, about 160 mM, about 165 mM, about 170 mM, about 175 mM, about 180 mM, about 185 mM. about 190 mM, about 195 mM, or about 200 mM.

In another specific embodiment, the buffering agent is at a concentration of 10 mM, 11 mM, 12 mM, 13 mM, 14 mM, 15 mM, 16 mM, 17 mM, 18 mM, 19 mM, 20 mM, 21 mM, 22 mM, 23 mM, 24 mM, 25 mM, 26 mM, 27 mM, 28 mM, 29 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 105 mM, 110 mM, 115 mM, 120 mM, 125 mM, 130 mM, 135 mM, 140 mM, 145 mM, 150 mM, 155 mM, 160 mM, 165 mM, 170 mM, 175 mM, 180 mM, 185 mM. about 190 mM, 195 mM, or 200 mM.

In an exemplary embodiment of the present disclosure, the sodium succinate buffer is at a concentration of about 10 mM to about 200 mM. In one embodiment, the sodium succinate buffer is at a concentration of about 10 mM. In another embodiment, the sodium succinate buffer is at a concentration of 10 mM In some embodiments, the composition of the present disclosure has a pH from about 5.0 to about 6.0. In specific embodiments, the buffer has a pH of about 5.0, about 5.1, about 5.2, about 5.3, about 5.4, about 5.5, about 5.6, about 5.7, about 5.8, about 5.9, or about 6.0. In other specific embodiments, the buffer has a pH of 5.0, 5.1, 5.2, 5.3, 5.4, 5.5, 5.6, 5.7, 5.8, 5.9, or 6.0.

In one exemplary embodiment, the composition of the present disclosure has a pH of about 5.3. In another exemplary embodiment, the composition of the present disclosure has a pH of 5.3.

D. Sugar

According to the present disclosure, pharmaceutical compositions that include a sugar are provided. Without wishing to be bound by theory, a sugar functions to promote cryoprotection of the pharmaceutical composition, thereby preventing aggregation and maintaining chemical and physical stability of the pharmaceutical composition. In certain embodiments, the sugar is glucose, fructose, sucrose, trehalose, arginin, glycerin, prolin, dextran, dextran 40, glycerol, mannitol, or sorbitol.

In some embodiments, the sugar is selected from the group consisting of: sucrose, mannitol, sorbitol, glycerol, dextran 40, and trehalose. In an exemplary embodiment, the sugar is sucrose.

In some embodiments, the sugar is at a concentration of about 50 mM to about 300 mM. In a specific embodiment, the buffering agent is at a concentration of about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM, about 200 mM, about 210 mM, about 220 mM, about 230 mM, about 240 mM, about 250 mM, about 260 mM, about 270 mM, about 280 mM, about 290 mM, or about 300 mM. In some embodiments, the sugar is at a concentration of about 100 mM to about 260 mM.

In some embodiments, the sugar is at a concentration of 50 mM to 300 mM. In a specific embodiment, the buffering agent is at a concentration of 50 mM, 60 mM, 70 mM, 80 mM, 90 mM, mM, 110 mM, 120 mM, 130 mM, 140 mM, 150 mM, 160 mM, 170 mM, 180 mM, 190 mM, 200 mM, 210 mM, 220 mM, 230 mM, 240 mM, 250 mM, 260 mM, 270 mM, 280 mM, 290 mM, or 300 mM. In some embodiments, the sugar is at a concentration of 100 mM to 260 mM.

In an exemplary embodiment of the present disclosure, sucrose is at a concentration of about 120 mM. In another exemplary embodiment, sucrose is at a concentration of 120 mM.

In another aspect, the present disclosure provides a pharmaceutical composition produced by lyophilization of a liquid composition comprising 20 mg/ml of an anti-CD79b immunoconjugate in 10 mM sodium succinate buffer, 0.12% w/v of polysorbate 20, and 120 mM sucrose, wherein the liquid composition has a pH of 5.3, and wherein the anti-CD79b immunoconjugate has the formula:

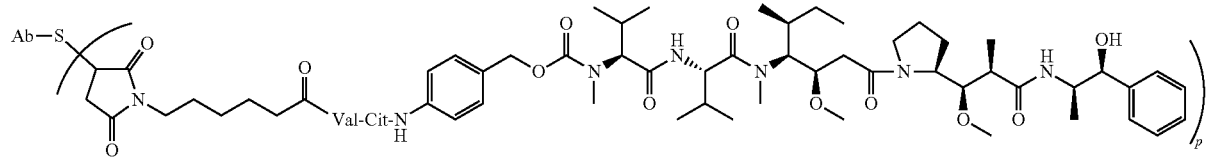

wherein:
Ab is an anti-CD79b antibody, wherein the anti-CD79b antibody comprises a heavy chain and a light chain, wherein the light chain comprises (a) an HVR-L1 sequence of KASQSVDYEGDSFLN (SEQ ID NO: 1); (b) an HVR-L2 sequence of AASNLES (SEQ ID NO: 2); and (c) an HVR-L3 sequence of QQSNEDPLT (SEQ ID NO: 3); wherein the heavy chain comprises (a) an HVR-H1 sequence of GYTFSSYWIE (SEQ ID NO: 4); (b) an HVR-H2 sequence of GEILPGGGDTNYNEIFKG (SEQ ID NO: 5); and (c) an HVR-H3 sequence of TRRVPIRLDY (SEQ ID NO: 6); Val is valine; Cit is citrulline; and p is a value from about 1 to about 8 (e.g., between about 2 and about 5, such as about 3.5).

In some embodiments of the present disclosure, the anti-CD79b antibody comprises a heavy chain variable domain (VH) comprising the amino acid sequence of SEQ ID NO: 7 and a light chain variable domain (VL) comprising the amino acid sequence of SEQ ID NO: 8. In some embodiments, the heavy chain comprises the amino acid sequence of SEQ ID NO: 9 and the light chain comprises the amino acid sequence of SEQ ID NO: 10.

E. Stability

In some embodiments, the physical stability, chemical stability, or biological activity of the pharmaceutical composition in a liquid state or a lyophilized form is evaluated or measured. Any methods known in the art and described in the Examples herein may be used to evaluate the stability and biological activity of the pharmaceutical composition of the present disclosure. For example, stability of the antibody in the pharmaceutical composition can be measured by, but not limited to, size exclusion chromatography (SEC or SE-HPLC), imaged capillary isoelectric focusing (icIEF), peptide mapping, small-volume light obscuration (HIAC) assay, and capillary electrophoresis (CE) techniques such as CE-sodium dodecyl sulfate (CE-SDS) and CE-glycan analysis. In some embodiments, stable pharmaceutical composition (or formulation) is one in which the immunoconjugate therein essentially retains its physical stability and/or chemical stability and/or biological activity upon storage; e.g., storage for a specified period or duration of time (such as hours, days, months, years, etc.) under specified conditions (such as temperature, relative humidity, residual moisture, presence or absence of light, following a period of agitation, etc.). In some embodiments, the immunoconjugate present in the pharmaceutical composition is biologically stable (e.g., retains its biological activity) if the biological activity of the immunoconjugate (and/or the antibody moiety of the immunoconjugate, such as an anti-CD79b antibody) at a given time is within the range accepted by a national or regional regulatory agency for pharmaceutical products (e.g., the Federal Drug Administration (FDA) of the United States, the Therapeutic Goods Administration (TGA) of Australia, the European Medicines Agency (EMA) of the European Union, etc.). For example, the biological activity of an immunoconjugate (such as an immunoconjugate comprising an anti-CD79b antibody) or a pharmaceutical composition comprising such an immunoconjugate can be measured by its ability to bind antigen (such as the ability of an anti-CD79b antibody to bind CD79b, e.g., human CD79b). A number of assays know in the art can be used to measure antibody binding affinity measurements, including without limitation, e.g., surface plasmon resonance (SPR), radioimmunoassay (RIA), and ELISA. Additionally or alternatively, the biological activit of an immunoconjugate (such as an immunoconjugate comprising an anti-CD79b antibody) is measured by its ability to inhibit cell growth and/or cell proliferation, e.g., in vitro or in vivo, or the ability to induce cell death, including programmed cell death (apoptosis) e.g., in vitro or in vivo. Further details regarding assays to measure the biological activity of an anti-CD79b antibody or an immunoconjugate comprising an anti-CD79b antibody are provided in U.S. Pat. No. 8,088,387, the contents of which are incorporated herein by reference in their entirety.

In some embodiments, the pharmaceutical composition of the present disclosure is stable at −20° C. for at least about 6 months, at least about 8 months, at least about 10 months, at least about 12 months, at least about 14 months, at least about 16 months, at least about 18 months, at least about 20 months, at least about 21 months, at least about 22 months, at least about 23 months, at least about 24 months, at least about 3 years, at least about 4 years, or at least about 5 years when protected from light.

In some embodiments, the pharmaceutical composition of the present disclosure is stable at 2° C. to 8° C. (e.g., 5° C.±3° C.) for at least about 6 months, at least about 8 months, at least about 10 months, at least about 12 months, at least about 14 months, at least about 16 months, at least about 18 months, at least about 20 months, at least about 21 months, at least about 22 months, at least about 23 months, at least about 24 months, at least about 3 years, at least about 4 years, or at least about 5 years when protected from light.

In some embodiments, the pharmaceutical composition of the present disclosure is stable at 25° C. to 40° C. for at least about 30 minutes, at least about 60 minutes, at least about 2 hours, at least about 4 hours, at least about 6 hours, at least about 8 hours, at least about 10 hours, at least about 12 hours, at least about 14 hours, at least about 16 hours, at least about 18 hours, at least about 20 hours, at least about 22 hours, at least about 1 day, at least about 2 days, or at least about 3 days.

In one exemplary embodiment, the composition has a stability of at least about 48 months at 5° C.±3° C. when protected from light. In another exemplary embodiment, the composition has a stability of about 48 months at 5° C.±3° C. when protected from light.

In certain embodiments, the lyophilized form (e.g. lyophilized cake) of the pharmaceutical composition of the present disclosure may be inspected for stability. In some embodiments, under storage conditions (5° C.±3° C. and protected from light), the lyophilized cake does not demonstrate any significant changes in the structure, color, appearance, or moisture content. In one specific embodiment, the lyophilized cake has a moisture content less than 5% under storage conditions. In another specific embodiment, the lyophilized cake is smooth without indentations under storage conditions. In certain embodiments of the present disclosure, the lyophilized cake is stable for at least about 48 months under storage conditions.

the pharmaceutical composition, when reconstituted in water, forms a liquid pharmaceutical composition comprising the anti-CD79b immunoconjugate at a concentration of about 10 mg/ml to about 20 mg/ml, the surfactant at a concentration of at least 0.06% w/v (i.e., 0.6 mg/ml), the succinate buffer at a concentration of about 10 mM to about 200 mM, and the sugar at a concentration of about 100 mM to about 260 mM, wherein the liquid pharmaceutical composition has a pH of 5.3, and wherein the anti-CD79b immunoconjugate comprises the formula:

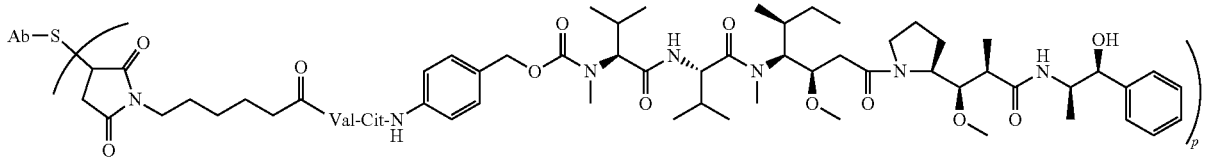

wherein:
Ab is an anti-CD79b antibody, wherein the anti-CD79b antibody comprises a heavy chain and a light chain, wherein the light chain comprises (a) an HVR-L1 sequence of KASQSVDYEGDSFLN (SEQ ID NO: 1); (b) an HVR-L2 sequence of AASNLES (SEQ ID NO: 2); and (c) an HVR-L3 sequence of QQSNEDPLT (SEQ ID NO: 3); wherein the heavy chain comprises (a) an HVR-H1 sequence of GYTFSSYWIE (SEQ ID NO: 4); (b) an HVR-H2 sequence of GEILPGGGDTNYNEIFKG (SEQ ID NO: 5); and (c) an HVR-H3 sequence of TRRVPIRLDY (SEQ ID NO: 6); Val is valine; Cit is citrulline; and p is a value from about 1 to about 8 (such as between about 2 and about 5, e.g., about 3.5).

In some embodiments, the stability of the pharmaceutical composition of the present disclosure is measured by size-exclusion chromatography high performance (SE-HPLC). In an exemplary embodiment, the composition has a main peak (area %) of at least 95.0 as measured by SE-HPLC.

In some embodiments, a lyophilized pharmaceutical composition (such as a cake) provided herein is stable for at least about 44 months (such as about any one of 30, 35, 40, 45, 50, or 55 months) when stored at a temperature between about 2° C. and about 8° C. over a residual moisture content range of about 0.3% (w/w) to about 3.2% (w/w), including any range in between these values. In some embodiments, a lyophilized pharmaceutical composition (such as a cake) provided herein is stable for at least about 7 months (such as about any one of 2, 3, 4, 5, 6, 7, 8, 8, or 10 months) when stored at about 25° C. over a residual moisture content range of about 0.3% (w/w) to about 3.2% (w/w), including any range in between these values.

In some embodiments, a lyophilized pharmaceutical composition (such as a cake) provided herein is robust over (a) protein concentration between about 17 and about 23 mg/ml, (b) a succinate concentration between about 7 and about 23 mM, (c) sucrose concentration between about 90 and about 150 mM, (d) a polysorbate 20 concentration between about 0.9 and about 1.5 mg/ml, and (e) a pH between about 4.95 and about 5.65. In some embodiments, a lyophilized pharmaceutical composition (such as a cake) comprising any one or more of (a) to (e) above is stable at a temperature between about 2° C. and about 8° C. for up to at least about any one of 5, 6, 7, 8, 9, 10, 11, 12, 13, 14, 15, 16, 17, 18, 19, 20, 21, 22, 23, 24, 25, 26, 27 28, 29, or 30 months.

G. Compositions for Intravenous Administration.

The present disclosure provides pharmaceutical compositions and liquid compositions suitable for intravenous (IV) administrations. The compositions to be used for in vivo IV administration should be sterile. This is readily accomplished by filtration through sterile filtration membranes, prior to, or following, preparation of the pharmaceutical composition. In certain embodiments, the pharmaceutical composition of the present disclosure is reconstituted with sterile water for injection (SWFI). In some embodiments, the reconstituted composition is further diluted into an isotonic buffer in an intravenous (IV) bag.

In one aspect, the present disclosure provides a pharmaceutical composition including an anti-CD79b immunoconjugate, a surfactant, a succinate buffer, and a sugar, wherein In some embodiments, the pharmaceutical composition is reconstituted (1:1 mass: volume) in SWFI. In some embodiments, the pharmaceutical composition, when reconstituted in water, forms a liquid pharmaceutical composition including 20 mg/ml of an anti-CD79b immunoconjugate in 10 mM sodium succinate buffer, 0.12% w/v of polysorbate 20, and 120 mM sucrose, wherein the liquid pharmaceutical composition has a pH of 5.3.

In some embodiments, the pharmaceutical composition is reconstituted in SWFI and subsequently diluted into an isotonic buffer in an IV bag, wherein the surfactant concentration upon dilution in the IV bag is at least 0.003% w/v. In one embodiment, the surfactant concentration upon dilution in the IV bag is at least 0.004% w/v. In an exemplary embodiment, the surfactant is polysorbate 20. In some embodiments, the sugar is sucrose. In a specific embodiment, the sucrose is at a concentration of 120 mM. In some embodiments, the succinate buffer is a sodium succinate buffer. In a specific exemplary embodiment, the sodium succinate buffer is at a concentration of 10 mM.

In some embodiments, the stability of the pharmaceutical composition present disclosure, when reconstituted in water, is measured by aggregation, pH, turbidity, the number of visible and/or sub-visible particles, or the amount of free (e.g. unconjugated) drug. In certain embodiments, UV spectrophotometry, SE-HPLC, hydrophobic interaction chromatography (HIC), icIEF, or HIAC, or a combination thereof, may be used to evaluate stability. In some embodiments, the pharmaceutical composition, when reconstituted in water, has a stability of up to about 1 day, up to about 2 days, or up to about 3 days at 30° C. In some embodiments, the pharmaceutical composition, when reconstituted in water, has a stability of up to about 1 day, up to about 2 days, up to about 3 days, up to about 4 days, up to about 5 days, up to 6 days, or up to about 7 days at 5° C.+3° C.

In certain embodiments, the stability of the composition reconstituted in water is measured by size-exclusion high performance liquid chromatography (SE-HPLC). In an exemplary embodiment, the composition has a main peak (area %) of at least 95.0 as measured by SE-HPLC.

In certain specific embodiments, the composition has a HMWS (%) of less than 4.0 as measured by SE-HPLC. In certain specific embodiments, the composition has a LMWS (%) of less than 1.0 as measured by SE-HPLC. In some embodiments, the composition has a main peak (area %) of at least 95.0 and a HMWS of less than 4.0 as measured by SE-HPLC. In some embodiments, the composition has a main peak (area %) of at least 95.0, a HMWS (%) of less than 4.0, and a LMWS (%) of less than 1.0 as measured by SE-HPLC.

In certain embodiments, the stability of the composition reconstituted in water is measured by imaged capillary isoelectric focusing (icIEF). In one embodiment, the composition has a main peak (area %) of at least 73.0, an acid region (area %) of at most 25.5, and a basic region (area %) of at most 10.0 as measured by icIEF. In an exemplary embodiment, the composition has a main peak (area %) of at least 58.0, an acid region (area %) of at most 32.0, and a basic region (area %) of at most 12.0 as measured by icIEF.

In some embodiments, a reconstituted pharmaceutical composition that comprises 20 mg/mL polatuzumab vedotin in 10 mM succinate, 120 mM sucrose, 1.2 mg/mL polysorbate 20, at pH 5.3 is physicochemically stable after 72 hours of storage at a temperature between about 2° C. and about 8° C. In some embodiments, storage of the reconstituted pharmaceutical composition for 72 hours at a temperature between about 2° C. and about 8° C. does not decrease the biological activity of the polatuzumab vedotin. In some embodiments, a reconstituted pharmaceutical composition that comprises 20 mg/mL polatuzumab vedotin in 10 mM succinate, 120 mM sucrose, 1.2 mg/mL polysorbate 20, at pH 5.3 is physicochemically stable after storage for 24 hours at 30° C. with exposure to ambient light. In some embodiments, storage of the reconstituted pharmaceutical composition for 24 hours at 30° C. with exposure to ambient light not decrease the biological activity of the polatuzumab vedotin.

In one aspect, the present disclosure provides a liquid composition comprising an anti-CD79b immunoconjugate, a surfactant, a succinate buffer, and a sugar, wherein the anti-CD79b immunoconjugate is at a concentration of about 10 mg/ml to about 20 mg/ml, the surfactant is at a concentration of at least 0.06% w/v (i.e., 0.6 mg/ml), the succinate buffer is at a concentration of about 10 mM to about 200 mM, and the sugar is at a concentration of about 100 mM to about 260 mM, wherein the liquid composition has a pH of 5.3, and wherein the anti-CD79b immunoconjugate comprises the formula:

wherein:
Ab is an anti-CD79b antibody, wherein the anti-CD79b antibody comprises a heavy chain and a light chain, wherein the light chain comprises (a) an HVR-L1 sequence of KASQSVDYEGDSFLN (SEQ ID NO: 1); (b) an HVR-L2 sequence of AASNLES (SEQ ID NO: 2); and (c) an HVR-L3 sequence of QQSNEDPLT (SEQ ID NO: 3); wherein the heavy chain comprises (a) an HVR-H1 sequence of GYTFSSYWIE (SEQ ID NO: 4); (b) an HVR-H2 sequence of GEILPGGGDTNYNEIFKG (SEQ ID NO: 5); and (c) an HVR-H3 sequence of TRRVPIRLDY (SEQ ID NO: 6); Val is valine; Cit is citrulline; and p is a value from about 1 to about 8 (e.g., between about 2 and about 5, such as about 3.5).

In some embodiments, the surfactant is polysorbate 20. In some embodiments, the sugar is sucrose. In an exemplary embodiment, the sucrose is at a concentration of 120 mM. In some embodiments, the succinate buffer is a sodium succinate buffer. In a specific exemplary embodiment, the sodium succinate buffer is at a concentration of 10 mM.

In certain embodiments, the liquid composition of the present disclosure is dissolved in a buffer. The buffer may be, without limitation, normal saline (0.9% w/v sodium chloride), half saline (0.45% w/v sodium chloride), 5% w/v dextrose, Lactated Ringer's solution, or a combination thereof.

In some embodiments, the liquid composition of the present disclosure is dissolved in an isotonic buffer. In certain embodiments, the isotonic buffer may be freshly prepared or contained in a pre-filled IV bag. In certain embodiments, the isotonic buffer is normal saline (0.9% sodium chloride). In an exemplary embodiment, the liquid composition of the present disclosure dissolved in an isotonic buffer is in an IV bag.

In some embodiments, the liquid composition of the present disclosure dissolved in an isotonic buffer in an IV bag has a pH of about 4.8 to about 5.8. In a specific embodiment, the pH is about 4.8, about 4.9, about 5.0, about 5.1, about 5.2, about 5.3, about 5.4, about 5.5, about 5.6, about 5.7, or about 5.8. In some embodiments, the liquid composition of the present disclosure dissolved in an isotonic buffer in an IV bag has a pH of about 5.3.

In some embodiments, the stability of the liquid composition in an IV bag of the present disclosure is measured by aggregation, pH, turbidity, the number of visible and/or sub-visible particles, or the amount of free (e.g. unconjugated) drug. In certain embodiments, UV spectrophotometry, SE-HPLC, hydrophobic interaction chromatography (HIC), icIEF, or HIAC, or a combination thereof, may be used to evaluate stability of the liquid composition in an IV bag.

In certain embodiments, the liquid composition in an IV bag of the present disclosure is stable under static conditions. In certain embodiments, the liquid composition in an IV bag of the present disclosure is stable under agitation conditions. In some embodiments, the liquid composition of

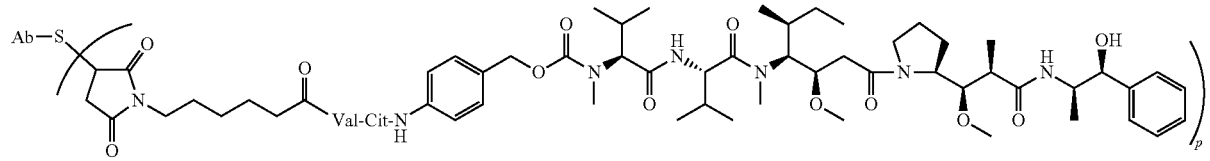

the present disclosure dissolved in an isotonic buffer in an IV bag has a stability of up to about 1 hour, up to about 2 hours, up to about 3 hours, up to about 4 hours, up to about 5 hours, up to about 6 hours, up to about 7 hours, or up to about 8 hours at 30° C. In some embodiments, the liquid composition of the present disclosure dissolved in an isotonic buffer in an IV bag has a stability of up to about 8 hours, up to about 9 hours, up to about 10 hours, up to about 12 hours, up to about 14 hours, up to about 16 hours, up to about 18 hours, up to about 20 hours, up to about 22 hours, or up to about 24 hours at 25° C. In some embodiments, the liquid composition of the present disclosure dissolved in an isotonic buffer in an IV bag has a stability of up to about 24 hours, up to about 30 hours, up to about 36 hours, up to about 42 hours, up to about 48 hours, up to about 54 hours, up to about 60 hours, up to about 66 hours, or up to about 72 hours at 5° C.±3° C. In certain embodiments, the isotonic buffer is normal saline.

In some embodiments, a reconstituted solution or a diluted solution for infusion described herein (e.g., a diluted solution for infusion comprising an immunoconjugate (e.g., polatuzumab vedotin)) is sterile.

III. Methods of Treatment

It is contemplated that the pharmaceutical composition or liquid composition of the present disclosure may be used to treat various proliferative disorders, e.g. characterized by the overexpression of a tumor antigen. An exemplary proliferative disorder is cancer. Examples of cancer include, but are not limited to, hematopoietic cancers or blood-related cancers, such as lymphoma, leukemia, myeloma or lymphoid malignancies, but also cancers of the spleen and cancers of the lymph nodes and also carcinoma, blastoma and sarcoma. More particular examples of cancer include B-cell proliferative disorders, including for example, high, intermediate and low grade lymphomas (including B cell lymphomas such as, for example, mucosa-associated-lymphoid tissue B cell lymphoma and non-Hodgkin's lymphoma (NHL), mantle cell lymphoma, Burkitt's lymphoma, small lymphocytic lymphoma, marginal zone lymphoma, diffuse large B cell lymphoma, follicular lymphoma, and Hodgkin's lymphoma and T cell lymphomas) and leukemias (including secondary leukemia, chronic lymphocytic leukemia (CLL), such as B cell leukemia (CD5+ B lymphocytes), myeloid leukemia, such as acute myeloid leukemia, chronic myeloid leukemia, lymphoid leukemia, such as acute lymphoblastic leukemia (ALL) and myelodysplasia), and other hematological and/or B cell- or T-cell-associated cancers. Also included are cancers of additional hematopoietic cells, including polymorphonuclear leukocytes, such as basophils, eosinophils, neutrophils and monocytes, dendritic cells, platelets, erythrocytes and natural killer cells. In certain embodiments, the proliferative disorder of the present disclosure is a relapsed cancer or a refractory cancer.

In certain embodiments, the pharmaceutical composition or liquid composition of the present disclosure may be used to treat a relapsed leukemia or a relapsed lymphoma. In other specific embodiments, the pharmaceutical composition or liquid composition of the present disclosure may be used to treat a refractory leukemia or a refractory lymphoma.

In one aspect, the present disclosure provides a method of treating a proliferative disorder in a patient in need thereof including administering to the patient a pharmaceutical composition or a liquid composition described herein.

In some embodiments, the cancer to be treated is a B cell proliferative disorder. In specific embodiments, the B cell proliferative disorder is selected from the group consisting of: lymphoma, myeloma, non-Hodgkin's lymphoma (NHL), diffuse large B-cell lymphoma (DLBCL), aggressive NHL, indolent lymphoma, follicular lymphoma (FL), relapsed aggressive NHL, relapsed indolent NHL, relapsed NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma.

In one exemplary embodiment of the present disclosure, the B cell proliferative disorder is non-Hodgkin's lymphoma (NHL). In one exemplary embodiment, the B cell proliferative disorder is diffuse large B-cell lymphoma (DLBCL). In one specific embodiment, the B cell proliferative disorder is relapsed diffuse large B-cell lymphoma (DLBCL). In another specific embodiment, the B cell proliferative disorder is refractory diffuse large B-cell lymphoma (DLBCL).

In one exemplary embodiment, the B cell proliferative disorder is relapsed NHL or refractory NHL. In still another exemplary embodiment, the B cell proliferative disorder is follicular lymphoma.

The cancer may comprise CD79b-expressing cells, such that the anti-CD79b immunoconjugates of the present disclosure are able to bind to the cancer cells. To determine CD79b expression in the cancer, various diagnostic/prognostic assays are available. In one embodiment, CD79b overexpression may be analyzed by IHC. Paraffin-embedded tissue sections from a tumor biopsy may be subjected to the IHC assay and accorded a CD79b protein staining intensity criteria with respect to the degree of staining and in what proportion of tumor cells examined.

For the prevention or treatment of a disorder, the appropriate dosage of an ADC will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 μg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 μg/kg to 100 mg/kg or more, depending on the factors mentioned above. An exemplary dosage of ADC to be administered to a patient is in the range of about 0.1 to about 10 mg/kg of patient weight. For repeated administrations over several days or longer, depending on the condition, the treatment is sustained until a desired suppression of disease symptoms occurs.

For treating or preventing a proliferative disorder, the pharmaceutical composition or liquid composition the present disclosure is administered via intravenous infusion. The dosage administered via infusion is in the range of about 1 μg/m² to about 10,000 μg/m² per dose, generally one dose per week for a total of one, two, three or four doses. Alternatively, the dosage range is of about 1 μg/m² to about 1000 μg/m², about 1 μg/m² to about 800 μg/m², about 1 μg/m² to about 600 μg/m², about 1 μg/m² to about 400 μg/m², about 10 μg/m² to about 500 μg/m², about 10 μg/m² to about 300 μg/m², about 10 μg/m² to about 200 μg/m², and about 1 μg/m² to about 200 μg/m². The dose may be administered once per day, once per week, multiple times per week, but less than once per day, multiple times per month but less than once per day, multiple times per month but less than once per week, once per month or intermittently to relieve or alleviate symptoms of the disease. Administration may continue at any of the disclosed intervals until remission of the tumor or symptoms of the lymphoma, leukemia being treated. Administration may continue after remission or relief of symptoms is achieved where such remission or relief is prolonged by such continued administration.

To determine CD79b expression in the cancer, various detection assays are available. In one embodiment, CD79b polypeptide overexpression may be analyzed by immunohistochemistry (IHC). Paraffin embedded tissue sections from a tumor biopsy may be subjected to the IHC assay and accorded a CD79b protein staining intensity criteria as follows:

Score 0+—no staining is observed or membrane staining is observed in less than 10% of tumor cells.

Score 1+—a faint/barely perceptible membrane staining is detected in more than 10% of the tumor cells. The cells are only stained in part of their membrane.

Score 2+—a weak to moderate complete membrane staining is observed in more than 10% of the tumor cells.

Score 3+—a moderate to strong complete membrane staining is observed in more than 10% of the tumor cells.

Those tumors with 0 or 1+ scores for CD79b polypeptide expression may be characterized as not overexpressing CD79b, whereas those tumors with 2+ or 3+ scores may be characterized as overexpressing CD79b.

Alternatively, or additionally, FISH assays such as the INFORM® (sold by Ventana, Ariz.) or PATHVISION® (Vysis, Ill.) may be carried out on formalin-fixed, paraffin-embedded tumor tissue to determine the extent (if any) of CD79b overexpression in the tumor.

CD79b overexpression or amplification may be evaluated using an in vivo detection assay, e.g., by administering a molecule (such as an antibody) which binds the molecule to be detected and is tagged with a detectable label (e.g., a radioactive isotope or a fluorescent label) and externally scanning the patient for localization of the label.

Combination Therapies

Currently, depending on the stage of the cancer, cancer treatment involves one or a combination of the following therapies: surgery to remove the cancerous tissue, radiation therapy, and chemotherapy. Anti-CD79b immunoconjugate therapy may be especially desirable in elderly patients who do not tolerate the toxicity and side effects of chemotherapy well and in metastatic disease where radiation therapy has limited usefulness. The tumor targeting anti-CD79b immunoconjugates of the present disclosure are useful to alleviate CD79b-expressing cancers upon initial diagnosis of the disease or during relapse. For therapeutic applications, the anti-CD79b immunoconjugate can be used alone, or in combination therapy with, e.g., hormones, anti-angiogenic agents, or radiolabeled compounds, or with surgery, cryotherapy, and/or radiotherapy. Administration of a pharmaceutical composition or liquid composition of the present disclosure may be performed in conjunction with other forms of conventional therapy, either consecutively with, pre- or post-conventional therapy. Chemotherapeutic drugs such as TAXOTERE® (docetaxel), TAXOL® (paclitaxel), estramustine and mitoxantrone are used in treating cancer, in particular, in good risk patients. In the present method of the disclosure for treating or alleviating cancer, the cancer patient can be administered anti-CD79b antibody in conjunction with treatment with the one or more of the preceding chemotherapeutic agents. In particular, combination therapy with paclitaxel and modified derivatives (see, e.g., EP0600517) is contemplated. The pharmaceutical composition or liquid composition of the present disclosure may be administered with a therapeutically effective dose of the chemotherapeutic agent. In another embodiment, the pharmaceutical composition or liquid composition of the present disclosure is administered in conjunction with chemotherapy to enhance the activity and efficacy of the chemotherapeutic agent, e.g., paclitaxel. The Physicians' Desk Reference (PDR) discloses dosages of these agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician.

In another embodiment, the pharmaceutical composition or liquid composition of the present disclosure may be administered in combination with one or more chemotherapeutic agents or growth inhibitory agents, including co-administration of cocktails of different chemotherapeutic agents, or other cytotoxic agent(s) or other therapeutic agent(s) which also inhibits tumor growth. Chemotherapeutic agents include estramustine phosphate, prednimustine, cisplatin, 5-fluorouracil, melphalan, cyclophosphamide, hydroxyurea and hydroxyureataxanes (such as paclitaxel and doxetaxel) and/or anthracycline antibiotics. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992). The pharmaceutical composition or liquid composition of the present disclosure may be combined with an anti-hormonal compound; e.g., an anti-estrogen compound such as tamoxifen; an anti-progesterone such as onapristone (see, EP 616 812); or an anti-androgen such as flutamide, in dosages known for such molecules. Where the cancer to be treated is androgen independent cancer, the patient may previously have been subjected to anti-androgen therapy and, after the cancer becomes androgen independent, the pharmaceutical composition or liquid composition of the present disclosure may be administered to the patient.

Sometimes, it may be beneficial to also co-administer a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy (e.g. external beam irradiation or therapy with a radioactive labeled agent, such as an antibody), before, simultaneously with, or post administration of a pharmaceutical composition or a liquid composition of the present disclosure. Suitable dosages for any of the above co-administered agents are those presently used and may be lowered due to the combined action (synergy) of the agent and anti-CD79b antibody.

In some embodiments, a pharmaceutical composition or liquid composition of the present disclosure may be administered in combination with an effective amount of another therapeutic agent to a patient. In one embodiment, the therapeutic agent is selected from the group consisting of an antibody, a chemotherapeutic agent, a cytotoxic agent, an anti-angiogenic agent, an immunosuppressive agent, a prodrug, a cytokine, a cytokine antagonist, cytotoxic radiotherapy, a corticosteroid, a cancer vaccine, and a growth-inhibitory agent. In another embodiment, the therapeutic agent is selected from one or more of tamoxifen, letrozole, exemestane, anastrozole, irinotecan, cetuximab, fulvestrant, vinorelbine, erlotinib, bevacizumab, vincristine, imatinib mesylate, sorafenib, lapatinib, trastuzumab, cisplatin, gemcitabine, methotrexate, vinblastine, carboplatin, paclitaxel, 5-fluorouracil, doxorubicin, bortezomib, melphalan, prednisone, prednisolone, and docetaxel.

In a some embodiments, the therapeutic agent is an anti-CD20 antibody.

In certain embodiments, the pharmaceutical composition or liquid composition of the present disclosure may be may be administered in combination with an effective amount of an anti-CD20 antibody to treat a B cell proliferative disorder. In one embodiment, the B cell proliferative disorder is diffuse large B-cell lymphoma (DLBCL). In another embodiment, the proliferative disorder is follicular lymphoma (FL). In certain embodiments, the anti-CD20 antibody is rituximab.

In some embodiments, the therapeutic agent is a chemotherapeutic agent. In one embodiment, the chemotherapeutic agent comprises one or more of cyclophosphamide, hydroxydaunorubicin, vincristine, and prednisone. In another embodiment, the chemotherapeutic agent comprises cyclophosphamide, doxorubicin, and prednisone.

In some embodiments, a pharmaceutical composition or liquid composition of the present disclosure may be administered in combination with an effective amount of an anti-CD20 antibody and a chemotherapeutic agent. In one embodiment, the chemotherapeutic agent comprises cyclophosphamide, doxorubicin, and prednisone.

In some embodiments, a pharmaceutical composition or liquid composition of the present disclosure may be administered in combination with an effective amount of an anti-CD20 antibody and a chemotherapeutic agent to treat a B cell proliferative disorder. In one embodiment, the B cell proliferative disorder is non-Hodgkin's lymphoma (NHL). In another embodiment, the B cell proliferative disorder is diffuse large B-cell lymphoma (DLBCL). In a specific embodiment, the DLBCL is relapsed/refractory DLBCL. In another embodiment, the NHL is relapsed NHL or refractory NHL. In another specific embodiment, the proliferative disorder is follicular lymphoma (FL). In another embodiment, the FL is relapsed/refractory FL. In certain embodiments, the anti-CD20 antibody is rituximab.

In some embodiments, a pharmaceutical composition or liquid composition of the present disclosure of the present disclosure may be combined with an anti-CD20 antibody (either a naked antibody or an ADC). In one embodiment the anti-CD20 antibody is rituximab (Rituxan®) or its biosimilar. In some embodiments the anti-CD20 antibody is ocrelizumab (2H7) (Genentech, Inc., South San Francisco, Calif.) or its biosimilar. In another embodiment, a pharmaceutical composition or liquid composition of the present disclosure of the present disclosure may be combined with an anti-VEGF antibody (e.g., Avastin®).

In some embodiments, a pharmaceutical composition or liquid composition of the present disclosure of the present disclosure may be combined with an alkylating agent. In some embodiments, a pharmaceutical composition or liquid composition of the present disclosure may be combined with an alkylating agent and an anti-CD20 antibody (either a naked antibody or an ADC). In some embodiments, the anti-CD20 antibody is rituximab (Rituxan®) or its biosimilar. In some embodiments, the alkylating agent is 4-[5-[Bis(2-chloroethyl)amino]-1-methylbenzimidazol-2-yl]butanoic acid and salts thereof. In some embodiments, the alkylating agent is bendamustine.

The combination therapy may be administered as a simultaneous or sequential regimen. When administered sequentially, the combination may be administered in two or more administrations. The combined administration includes co-administration, using separate formulations or a single pharmaceutical formulation, and consecutive administration in either order, wherein preferably there is a time period while both (or all) active agents simultaneously exert their biological activities.

Suitable dosages for any of the above co-administered agents are those presently used and may be lowered due to the combined action (synergy) of the newly identified agent and other chemotherapeutic agents or treatments.

The combination therapy may provide "synergy" and prove "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

IV. Articles of Manufacture and Kits

Another embodiment of the present disclosure is an article of manufacture containing materials useful for the treatment, prevention and/or diagnosis of a proliferative disorder. In one embodiment, the article of manufacture includes a container and a label or package insert on or associated with the container. Suitable containers include, for example, bottles, vials, syringes, etc. The containers may be formed from a variety of materials such as glass or plastic. The container holds a composition which is effective for treating, preventing and/or diagnosing the cancer condition and may have a sterile access port (for example the container may be an intravenous solution bag or a vial having a stopper pierceable by a hypodermic injection needle). At least one active agent in the composition is an anti-CD79b immunoconjugate of the present disclosure. The label or package insert indicates that the composition is used for treating cancer. The label or package insert will further comprise instructions for administering the composition to the cancer patient. Additionally, the article of manufacture may further comprise a second container comprising a pharmaceutically-acceptable buffer, such as sterile water for injection (SWFI), bacteriostatic water for injection (BWFI), phosphate-buffered saline, Ringer's solution and dextrose solution. It may further include other materials desirable from a commercial and user standpoint, including other buffers, diluents, filters, needles, and syringes.

In some embodiments, the article of manufacture is a container, such as a bottle, vial, syringe, that includes the pharmaceutical composition of the present disclosure. In some embodiments, the article of manufacture is a container, such as a bottle, vial, syringe, that includes the lyophilized pharmaceutical composition (such as a cake) of the present disclosure. In some embodiments, the article of manufacture is a container, such as a bottle, vial, syringe, that includes the reconstituted lyophilized pharmaceutical composition of the present disclosure. In a specific embodiment, the article of manufacture is a container that includes the lyophilized pharmaceutical composition is reconstituted with sterile water for injection (SWFI).

In some embodiments, the article of manufacture is a plastic container that includes the pharmaceutical composition of the present disclosure. In some embodiments, the article of manufacture is a glass container that includes the pharmaceutical composition of the present disclosure.

In some embodiments, the article of manufacture is a glass vial that includes the pharmaceutical composition of the present disclosure. In a specific embodiment, the article of manufacture is a glass vial that includes the lyophilized pharmaceutical composition (such as a cake) of the present disclosure. In a specific embodiment, the article of manufacture is a glass vial that includes the reconstituted lyophilized pharmaceutical composition (such as a cake) of the present disclosure. In a specific embodiment, the article of manufacture is a glass vial that includes the lyophilized pharmaceutical composition (such as a cake) is reconstituted with sterile water for injection (SWFI).

In certain embodiments, the article of manufacture is an IV bag containing the pharmaceutical composition or liquid composition of the present disclosure. The IV bag may composed of materials including, without limitation, polyolefin (PO), polyvinyl chloride (PVC), ethylene vinyl acetate, polypropylene (PP), polyethylene (PE), copolyester ether, or a combination thereof. In some embodiments, IV bag is a polyolefin (PO) bag, a polypropylene bag (PP), a polyethylene bag (PE) or a polyvinyl chloride (PVC) bag.

In some embodiments, the article of manufacture containing the pharmaceutical composition or liquid composition of the present disclosure can accommodate a volume of at least about 5 milliliters (mLs), at least about 10 mLs, at least about 15 mLs, at least about 20 mLs, at least about 25 mLs, at least about 30 mLs, at least about 35 mLs, at least about 40 mLs, at least about 45 mLs, at least about 50 mLs, at least about 55 mLs, at least about 60 mLs, at least about 65 mLs, at least about 70 mLs, at least about 75 mLs, at least about 80 mLs, at least about 85 mLs, at least about 90 mLs, at least about 95 mLs, at least about 100 mLs, at least about 105 mLs, at least about 110 mLs, at least about 115 mLs, at least about 120 mLs, at least about 125 mLs, at least about 130 mLs, at least about 135 mLs, at least about 140 mLs, at least about 145 mLs, at least about 150 mLs, at least about 155 mLs, at least about 160 mLs, at least about 165 mLs, at least about 170 mLs, at least about 175 mLs, at least about 180 mLs, at least about 185 mLs, at least about 190 mLs, at least about 195 mLs, or at least about 200 mLs. In some embodiments, the article of manufacture is a PO bag that can accommodate a volume of at least about 25 mLs, at least about 50 mLs, or at least about 100 mLs. In some embodiments, the article of manufacture is a PVC bag that can accommodate a volume of at least about 25 mLs, at least about 50 mLs, or at least about 100 mLs.

In certain embodiments, the article of manufacture is an IV bag including the pharmaceutical composition or liquid composition of the present disclosure and a buffer. In a specific embodiment, the buffer may be normal saline, half saline, 5% w/v dextrose, Lactated Ringer's solution, or a combination thereof. In one embodiment, the article of manufacture is an IV bag including the pharmaceutical composition or liquid composition of the present disclosure dissolved in half saline.

In some embodiments, the article of manufacture is an IV bag including the pharmaceutical composition or liquid composition of the present disclosure and an isotonic buffer. In one embodiment, the article of manufacture is an IV bag including the pharmaceutical composition or liquid composition of the present disclosure dissolved in normal saline.

In one exemplary embodiment, the article of manufacture is a PVC bag including the pharmaceutical composition or liquid composition of the present disclosure and normal saline that can accommodate a volume of at least about 100 mLs. In another exemplary embodiment, the article of manufacture is a PVC bag including the pharmaceutical composition or liquid composition of the present disclosure and normal saline that can accommodate a volume of about 100 mLs.

In another exemplary embodiment, the article of manufacture is a PO bag including the pharmaceutical composition or liquid composition of the present disclosure and normal saline that can accommodate a volume of at least about 100 mLs. In still another exemplary embodiment, the article of manufacture is a PO bag including the pharmaceutical composition or liquid composition of the present disclosure and half saline that can accommodate a volume of at least about 100 mLs.

In any of the embodiments herein, the stable pharmaceutical or liquid pharmaceutical composition can be stored in a container, such as a bottle, vial, syringe, or an intravenous (IV) bag.

Kits are also provided that are useful for various purposes, such as for CD79b-expressing cell killing assays. As with the article of manufacture, the kit comprises a container and a label or package insert on or associated with the container. The container holds a composition comprising at least one anti-CD79b immunoconjugate of the disclosure. Additional containers may be included that contain, e.g., diluents, surfactants, buffers, control antibodies. The label or package insert may provide a description of the composition as well as instructions for the intended use.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

EXAMPLES

Example 1: Anti-CD79b Immunoconjugate Surfactant Studies

The formulation used initially for early phase clinical testing in patients for the anti-CD79b-vc-MMAE was a liquid formulation, comprising a histidine acetate buffer with 0.02% polysorbate 20, which was delivered to patients via an intravenous syringe pump. In order to establish the commercial formulation for the drug product, various nonionic surfactants at different concentrations were tested to determine whether they could protect and stabilize the anti-CD79b-vc-MMAE against aggregation when diluted in an IV bag, which would be the route of delivery to patients in the commercial setting. Specifically, stability of the anti-CD79b-vc-MMAE was evaluated under both (a) static conditions in an IV bag, and (b) air-water interfacial stress conditions caused by short-term agitation in an IV bag.

Anti-CD79b-Vc-MMAE

Anti-CD79b-vc-MMAE was diluted in 20 mM histidine acetate, pH 5.5. The 20 mM histidine acetate pH 5.5 buffer was prepared by adding 3.11 g of histidine and 1.03 mL of glacial acetic acid in 800 mL of fresh ultrapure water. The measured pH was 5.5±0.1. The resulting solution was adjusted to 1 L using fresh-ultrapure water and filtered through a 0.22 μM PES filter and stored at 2-8° C. The concentrations of the anti-CD79b-vc-MMAE were tested at both (i) 10 mg/mL, and (ii) 20 mg/mL by diluting in filtered buffer to 10 mg/mL or 20 mg/mL, as required. The diluted material was stored at 2-8° C. and protected from light.

Surfactant

The surfactants tested were: (i) polysorbate 20 (PS20), Grade USP, NF, manufactured by Croda; (ii) polysorbate 80 (PS80), Grade USP, NF, manufactured by Croda; (iii) poloxamer (P188), Grade USP, NF containing 98 ppm butylated hydroxytouluene, manufactured by Spectrum Chemicals; and (iv)N-octyl-β-D Glucopyranoside (OG) C14H2806, FW: 292.4, manufactured by Affymetrix, Anagrade. Preparation of 10%, 1.0%, and 0.5% PS20 stock solution was prepared as follows: depending on the target concentration of PS20 in the bag, a 10%, 1%, or 0.5% PS20 stock solution in ultrapure water was used. The 10% PS20 stock solution was prepared by adding 10 g of PS20 in a 100 mL volumetric flask. The flask was filled with 60 mL of ultrapure water and then stirred with a magnetic stirrer to ensure the solution was well-mixed. After allowing the bubbles to subside for 30 min, the flask was filled to 100 mL with ultrapure water. The solution was transferred to a light-protective container and stored for a maximum of 1 week at 2-8° C. A similar procedure was used to prepare the 1.0% PS20 solution using 1.0 g of PS20 in 100 mL of ultrapure water. A 1:1 (v/v) dilution of the 1.0% PS20 stock was used to make the 0.5% PS20 solution.

Preparation of 0.5% PS80 was as follows: A 10% PS20 stock was prepared by adding 10 g of PS80 in a 100 mL volumetric flask. The flask was filled with 50 mL of ultrapure water and then stirred with a magnetic stirrer until the solution was well-mixed. The solution was allowed to sit for 30 min to allow the bubbles to subside, and then the stirred was removed. The solution volume was then adjusted to 100 mL using ultrapure water. To obtain the 0.5% stock solution of PS80, 0.5 mL of 10% PS80 stock solution was adjusted to 10 mL using ultrapure water. The solutions were transferred to a light protective container and stored for a maximum of 1 week at 2-8° C.

Preparation of 0.5% P188 was as follows: A 10% P188 stock was prepared by adding 10 g of P188 in a 100 mL volumetric flask. The flask was filled with 60 mL of ultrapure water and then stirred with a magnetic stirrer until the solution was well-mixed. The solution was allowed to sit for 30 min to allow the bubbles to subside, and then the stirred was removed. The solution volume was then adjusted to 100 mL using ultrapure water. To obtain the 0.5% stock solution of P188, 0.5 mL of 10% P188 stock solution was adjusted to 10 mL using ultrapure water. The solutions were transferred to a light protective container and stored for a maximum of 1 week at 2-8° C.

A. Static IV Bag Studies:

The anti-CD79b-vc-MMAE was diluted into IV bags. In order to mimic the recommended preparation procedure in the pharmacy, an equal volume of saline was removed from the IV bag as the total volume of anti-CD79b-vc-MMAE and surfactant that would be added. Surfactants were introduced to the IV bags prior to the anti-CD79b-vc-MMAE formulation in histidine buffer, ensuring that the anti-CD79b-vc-MMAE as a surfactant-free ultrafiltration diafiltration (UFDF) pool was not exposed to saline without any surfactant in the IV bag. The IV bags were then gently rotated to allow complete mixing while avoiding any vigorous shaking and agitation of the bags containing anti-CD79b-vc-MMAE.

Preparation of anti-CD79b-vc-MMAE in saline contained in glass vials: Various amounts of saline (0.9% sodium chloride), surfactants, and immunoconjugate were added to a 15-cc Forma Vitrum glass vial and capped with 20-mm Daikyo stopper. Samples were later incubated under particular study conditions.

Sample collection: Throughout the course of a study, samples were removed using a 1-cc or 5-cc BD Falcon syringe in combination with an 18 G needle. Collected samples were stored in 10-cc PETG (Nalgene) containers.

Protein Concentration Determination by UV spectrophotometry scan: Protein concentration after dilution was determined for selected samples using an Agilent spectrophotometer. Samples collected from IV bags were diluted (if required) volumetrically so that the UV signal was between 0.1 and 1.0 AU. Absorbance was recorded at 279 nm and 320 nm. The UV concentration determination was calculated by using an extinction coefficient of 1.40 (mg/mL)-1 cm-1. The corrected A279 was obtained by subtracting A320 nm from A279 nm. This correction accounts for the turbidity of the solution and enables accurate measurement of the protein concentration.

Turbidity: The turbidity of the samples was measured by recording the average UV absorbance from 340-360 nm using a 1-cm path length cuvette in an Agilent spectrophotometer. The spectrophotometer was blanked with purified water.

Visible particles: The presence of any visible particles was visually assessed against a black and white background light box with samples in a 10-cc PETG container. Soluble aggregate content, as a measure of protein instability, was determined using an Agilent 1200/1280 high performance size exclusion chromatography (HPSEC) (Agilent Technologies, Santa Clara, Calif.) equipped with a diode array detector set at 280 nm and a Tosoh Bioscience LLC (Montgomeryville, Pa.) TSK-Gel G3000SWXL size-exclusion column (300×7.8 mm, 5 μm) at ambient temperature. Samples were eluted over 30 min with an isocratic flow rate of 0.5 mL/min using 0.2 M K3PO4, 0.25 M KCl, pH 6.2.

High Accuracy Liquid Particle Counter (HIAC): HIAC was used to perform sizing and counting of particulates while in a solution. Light obscuration was used for the quantification of visible and/or sub-visible particles (SVP) using a HIAC (Model 9703+) instrument. The following particle sizes were collected: 1.6, 2, 3, 4, 5, 6, 7, 8, 9, 10, 11, 12, 15, 20, 25 and 50 m.

Stability Studies in IV Bags at Static Storage:

For surfactant studies in IV bags, an initial study was performed under both static and agitation conditions. The dosage range tested for these studies for the anti-CD79b-vc-MMAE were designed and performed at a range of 1.8 mg/kg to 2.4 mg/kg. It was assumed that majority of patient weights would fall between 40 kg and 120 kg. Based on these assumptions, the total dose per IV bag was varied between 72 mg (low dose/low weight) to 288 mg (high dose/high weight).

Figure 2:
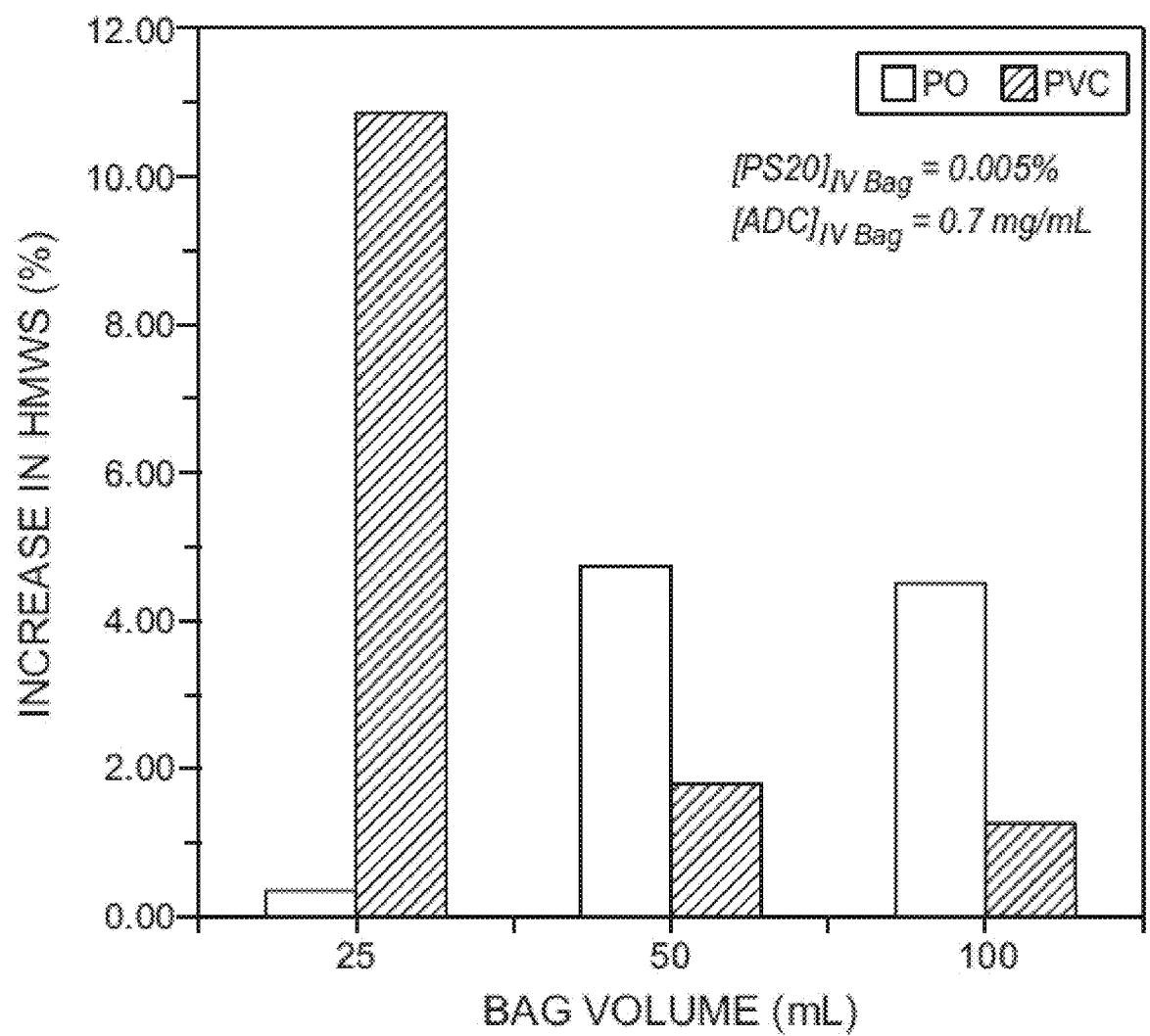
FIG. 2 depicts an increase in HMWS after 2 hours of agitation stress (100 rpm) at 30° C. with a fixed concentration of PS20 ([PS20]) in three different IV bag sizes.

FIG. 1-FIG. 2 summarize the results of IV bag performance with a fixed PS20 concentration of 0.005% in the bag and a final anti-CD79b-vc-MMAE concentration of 0.65 mg/mL. The concentration of the anti-CD79b-vc-MMAE concentration in the IV bag was chosen assuming a low dose of 1.8 mg/kg for the lowest patient weight of 40 kg patient in a 100 mL IV bag. Since 100 mL IV bags have an overfill of 10 mL, the final concentration in the IV bag was: (1.8 mg/kg×40 kg)/110 mL=0.65 mg/mL Under static storage condition at 30° C. for 22 hours, there were no significant differences between IV bag types with respect to the physical stability of anti-CD79b-vc-MMAE. All bags showed a 0.3%+0.1% increase (A) in high molecular weight species (HMWS) measured by SEC. This demonstrated that anti-CD79b-vc-MMAE was unstable at 30° C. upon dilution in 0.9% NaCl.

Surfactant and Screening Studies Under Static Storage:

For well-controlled and efficient screening of surfactant type and surfactant concentration, it was necessary to utilize a fixed protein concentration in the bag. An anti-CD79b-vc-MMAE concentration of 2.6 mg/mL in the bag was chosen based on the highest possible dose of 2.4 mg/kg for a heavy patient of 120 kg administered in a 100 mL bag, which is the recommended bag size for the clinic and has a 10% overfill volume, as seen in the following calculation: (2.4 mg/kg× 120 kg)/110 mL=2.6 mg/mL. The highest protein concentration in the bag was assumed be the worst case since higher bulk protein concentrations would drive more rapid adsorption of antibody to the air-water interface leading to higher levels of interfacially-mediated aggregation.

mediated by interfacial stress. The increase in HMWS showed a strong correlation to the storage temperature. These results correlate well with subsequent studies conducted by Beckley, N. et al., Investigation into Temperature-Induced Aggregation of an Antibody Drug Conjugate. *Bioconjugate Chemistry.*, 24, pp: 1674-1683 (2013), indicating that the formation of HMWS in antibody drug conjugates (ADCs) at higher temperatures is attributed to the increased sensitivity of the tertiary structure to thermal stress, presumably due to the presence of conjugated drugs at the interchain cysteines close to the CH2 domain.

Testing Surfactant Hybrids:

It is known that poloxamer 188 (P188) decreases the formation of HMWS in IV bags, but there can be a significant increase in sub-visible particles (SVP) upon agitation. In contrast, PS20 did not increase SVP. To further investigate these varying results between the two surfactants, a PS20-P188 hybrid at a 1:1 equal ratio by weight was used to determine if PS20 might prevent SVP formation and P188 might limit the increase in HMWS. The study was conducted in 25 mL IV bags using an anti-CD79b-vc-MMAE concentration of 2.6 mg/mL in the bag. On a mass basis, equal amounts of PS20 and P188 were added to yield a total surfactant concentration in the IV bag of either 0.05% or 0.1%. A 0.3-0.4% increase in HMWS was observed under static condition at 30° C. for 22 hours in TABLE 1 below.

TABLE 1

Hybrid PS20-P188 Surfactant study under Heat Stressed 30° C. Static Conditions

| Vol. of Bag (mL) | Temp. (° C.) | Surfactant (%) | Time (hr) | SEC (Relative Area Percent) (%) | | | Conc. (mg/mL) | Turbidity | HIAC (cumulative particles/mL) | | | |
|---|---|---|---|---|---|---|---|---|---|---|---|---|
| | | | | HMWS | Monomer | LMWS | | | 2 μm | 5 μm | 10 μm | 25 μm |
| 25 mL PVC Bag | 30° C. | 0.05% (0.025% PS20 and 0.025% P188) | 0 | 0.7 | 99.2 | 0.2 | 2.7 | 0.02 | 3309 | 498 | 54 | 8 |
| | | | 6 | 0.9 | 98.9 | 0.2 | NT | NT | NT | NT | NT | NT |
| | | | 22 | 1.2 | 98.6 | 0.2 | NT | 0.02 | 3002 | 287 | 38 | 3 |
| | | 0.1% (0.05% PS20 and 0.05% P188) | 0 | 0.7 | 99.2 | 0.2 | 2.7 | 0.05 | 1244 | 122 | 15 | 0 |
| | | | 6 | 0.8 | 99.0 | 0.2 | NT | NT | NT | NT | NT | NT |
| | | | 22 | 1.1 | 98.7 | 0.2 | NT | 0.02 | 3652 | 497 | 54 | 3 |

Effect of Temperature on Stability Under Static Storage.

Figure 3:
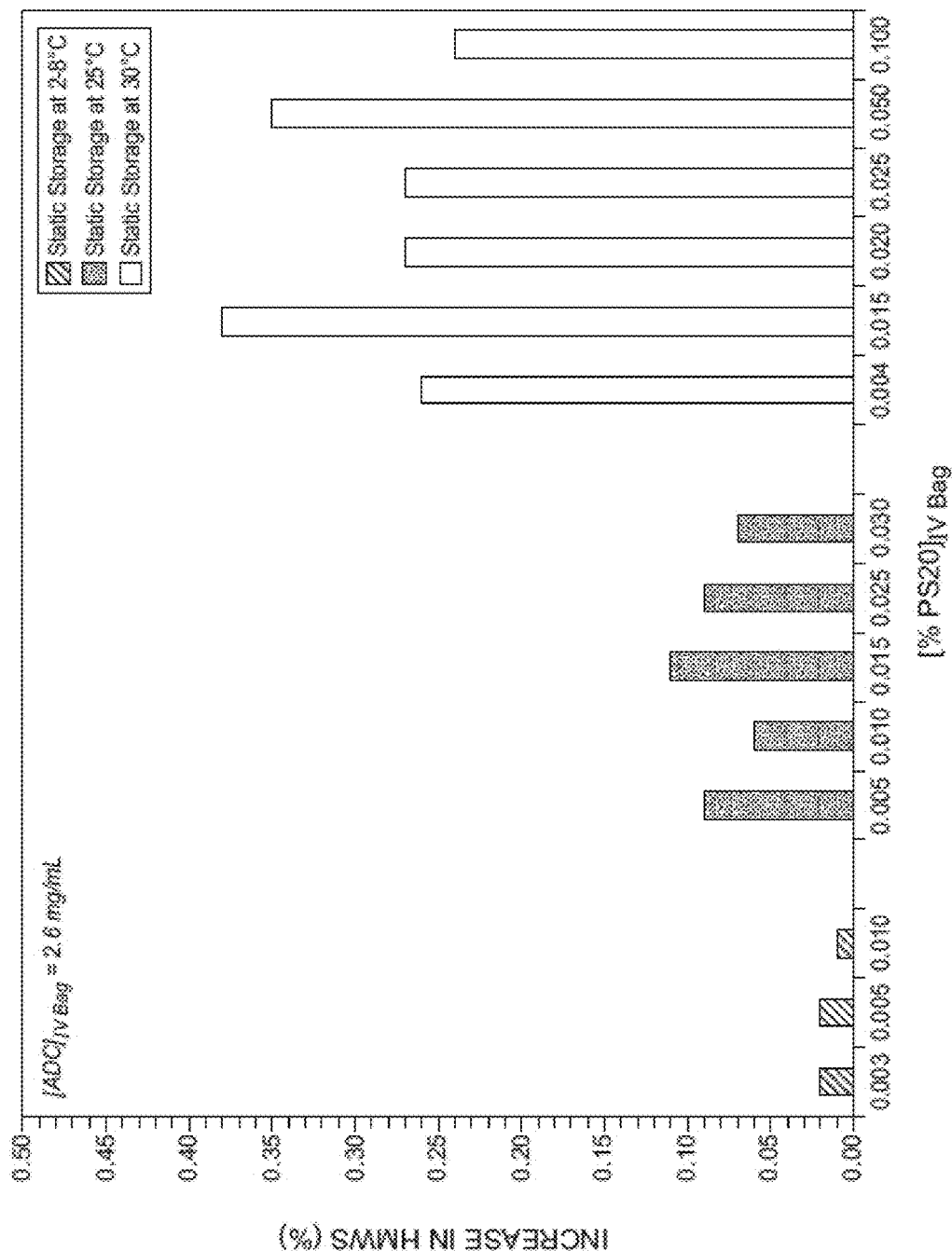
FIG. 3 depicts the effect of temperature on physical stability of anti-CD79b-vc-MMAE in saline IV bags at various concentrations of PS20 ([PS20]).

Providing an appropriate storage condition for a compounded IV bag is important for the product quality of the antibody therapeutic and was evaluated. This information is also required to prepare pharmacy manuals and product inserts to ensure proper usage of any antibody therapeutic. Various levels of PS20 in the bags were tested at temperatures of 30° C., 25° C., and 2-8° C. At 2-8° C., the tested levels of PS20 in the bag (0.003%, 0.005% and 0.01%) showed no significant changes in HMWS after 22 hours of static storage (FIG. 3). All changes (% HMWS) were <0.02%. At 25° C. and PS20 levels of 0.005%, 0.01%, 0.015%, 0.025% and 0.030% in the bag, an increase of ~0.1% HMWS was observed after 22 hours of static storage (FIG. 3). The increase in HMWS at 30° C. was much greater than that observed at 25° C. With PS20 levels of 0.004%, 0.015%, 0.02%, 0.025%, 0.05% and 0.1% in the bag after 22 hours of static storage, an increase of 0.3+0.1% was observed (FIG. 3).

Across all temperatures, the increase in HMWS was independent of the concentration of PS20 in the bag, indicating that the aggregation under static conditions was not There was a minor increase in particles above 5 μm, 10 μm, and 25 μm sizes. When 0.1% total surfactant was used in the IV bag, there was an increase in 2 μm particles. Based on the results, the surfactant hybrid did not demonstrate a substantial difference over PS20 alone.

Figure 4:
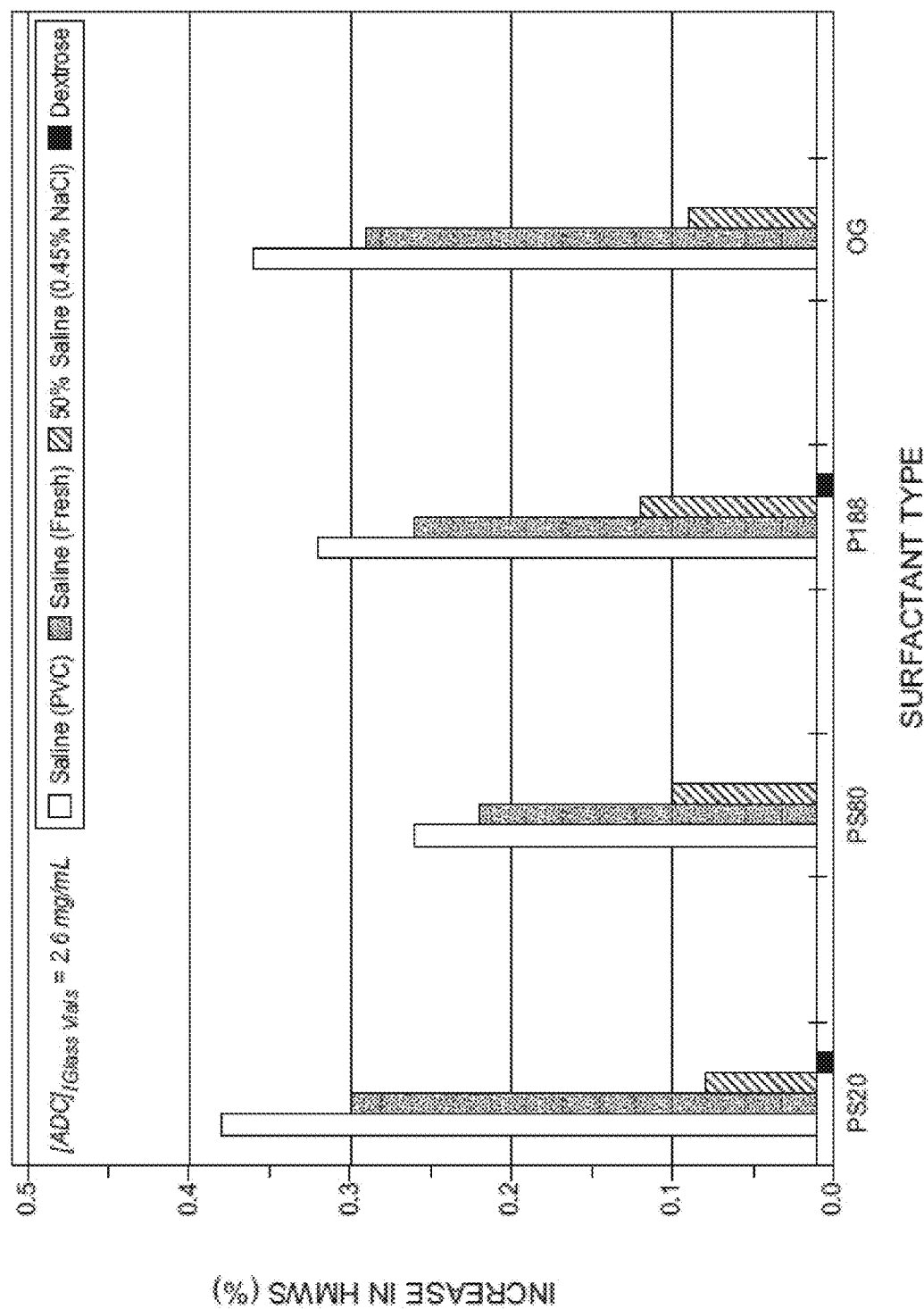
FIG. 4 depicts the effect of the type of surfactant and infusion fluid upon static storage at 30° C. for 22 hours.

Four different surfactants were evaluated for this study including PS20, PS80, P188, and octylglucoside (OG). After incubation at 30° C. for 22 hours with 0.02% surfactant and 2.6 mg/mL drug product in vials filled with saline from PVC bags, there was an increase of 0.3-0.4% HMWS, demonstrating that the aggregation was also independent of the type of surfactant used (FIG. 4).

Stability of Anti-CD79b-Vc-MMAE Under Static Storage in Vials:

Considering the physical instability of anti-CD79b-vc-MMAE in normal saline (0.9% NaCl) under static storage in an IV bag, the stability of the immunoconjugate in 5% dextrose (D5W) and half saline (0.45% w/v NaCl) was tested in vials to assess the dependence of the immunoconjugate instability on ionic strength. Solutions containing 0.02% PS20 were prepared with a fixed anti-CD79b-vc-MMAE concentration of 2.6 mg/mL. Anti-CD79b-vc- MMAE showed a significant improvement in physical stability in both half saline and D5W (FIG. 4). In the D5W solution, there was no change in HMWS while the half saline solution showed no more than 0.1% increase in HMWS after 24 hours of static storage at 30° C. Although preparation in D5W limited the aggregation of anti-CD79b-vc-MMAE, glycation of the antibody in the D5W solution is a known risk (see Fischer, S. et al., Glycation during Storage and Administration of Monoclonal Antibody Formulations. European J Pharma and Biopharm. vol. 70; pp. 42-50 (2008)). Therefore, IV delivery of anti-CD79b-vc-MMAE with 5% dextrose bags was not considered further due to the potential for glycation. Even though half saline showed a significant improvement in physical stability compared to normal saline, due to low availability of pre-made half saline bags in a global clinical and commercial setting, as well as the inconvenience and potential microbial contamination risks associated with preparation of half saline bags in pharmacies, the use of half saline for IV infusion of anti-CD79b-vc-MMAE was also not preferred.

Conclusions from Static Stability Studies in IV Bags and Glass Vials:

The static stability studies described above demonstrate that aggregation of the anti-CD79b-vc-MMAE is driven by high ionic strength environments, indicating that the rate of aggregation in formulation buffer is significantly slower than that in saline.

B. IV Bag Agitation Studies:

A series of IV bag agitation studies were conducted in order to support the transportation of compounded IV bags containing anti-CD79b-vc-MMAE in a hospital or clinical setting for dose administration. Although transportation of prepared IV bags containing therapeutic proteins is generally not recommended due to aggregation risk, there is frequently a practical need to transport IV bags in a clinical setting, especially in remote locations with limited access to pharmacies. Therefore, a minimal amount of transportation should be supported, and the impact on the drug due to agitation of the IV bag must be assessed during development. The agitation stress in IV bags during transportation can induce physical degradation to the antibody therapeutic. Physical degradation (i.e., aggregation and particle formation) of the antibody is likely mediated by adsorption to the air-liquid interface in the IV bag, which undergoes continuous regeneration during agitation. Throughout the course of the studies below, a MaxQ 4000 elliptical laboratory shaker (orbit length of 0.75 in) was utilized for the IV bag agitation studies. The IV bags were placed flat on the plane of the shaker.

Figure 5A:
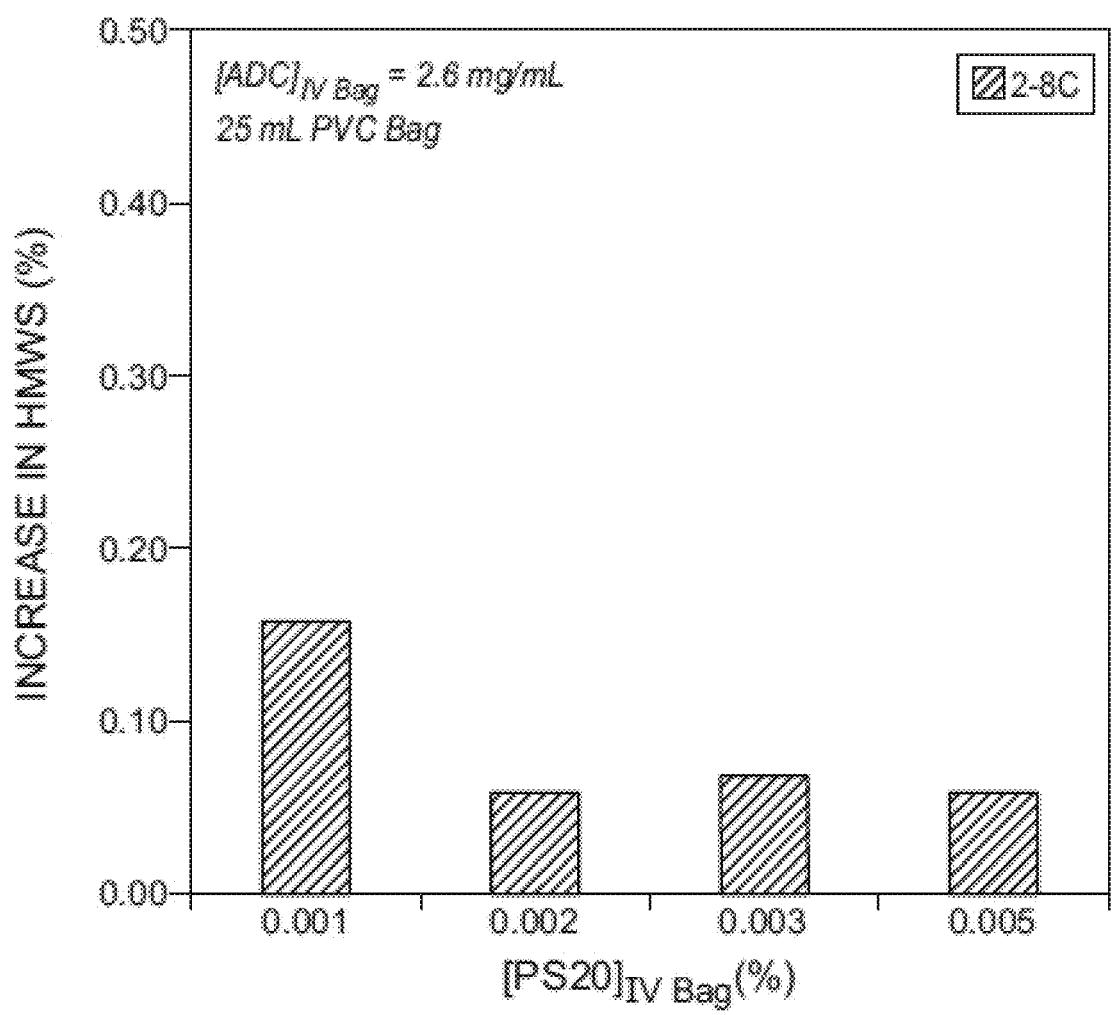
FIG. 5A depicts the effect of 2-8° C. temperature on stability of anti-CD79b-vc-MMAE upon agitation.
Figure 5B:
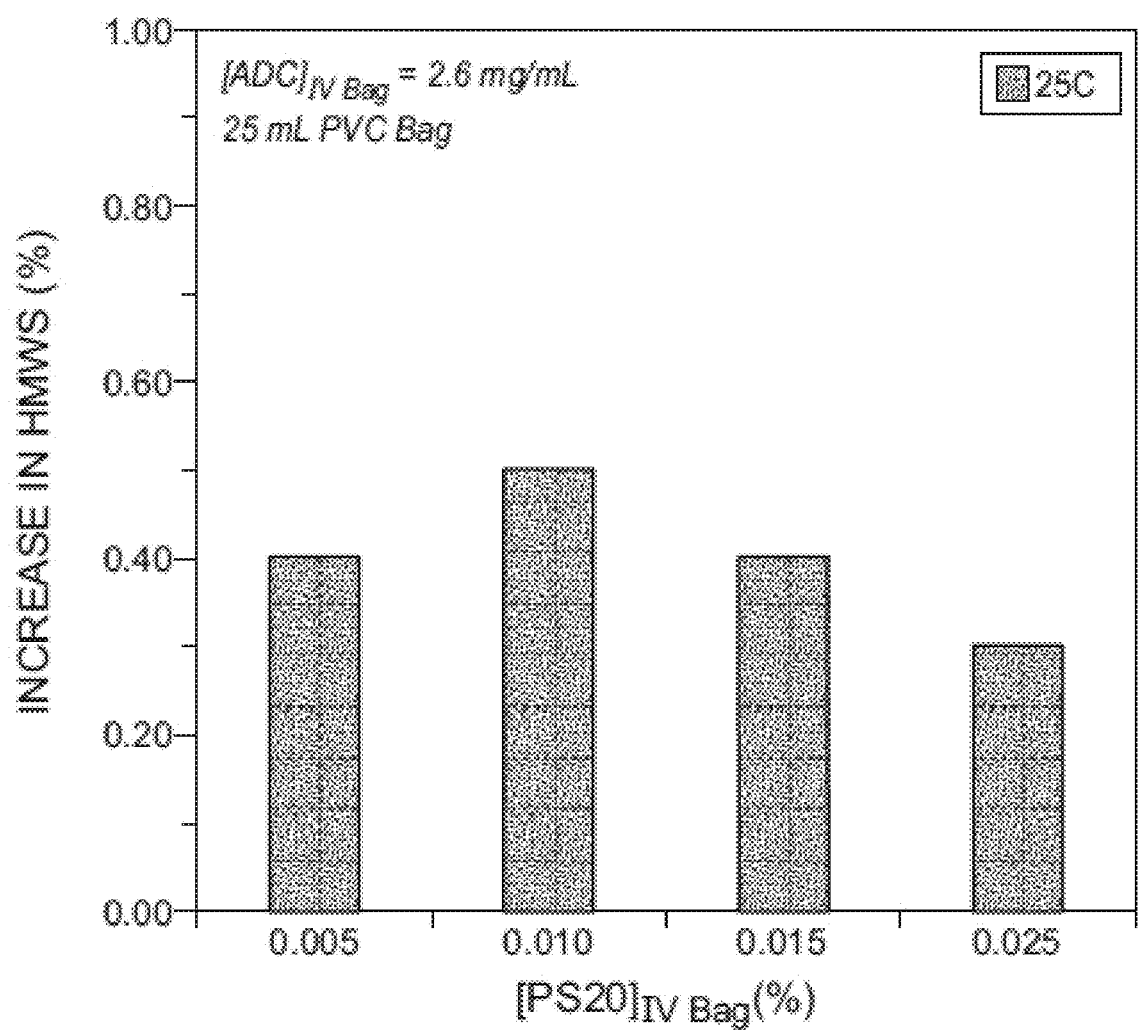
FIG. 5B depicts the effect of 25° C. temperature on stability of anti-CD79b-vc-MMAE upon agitation.
Figure 5C:
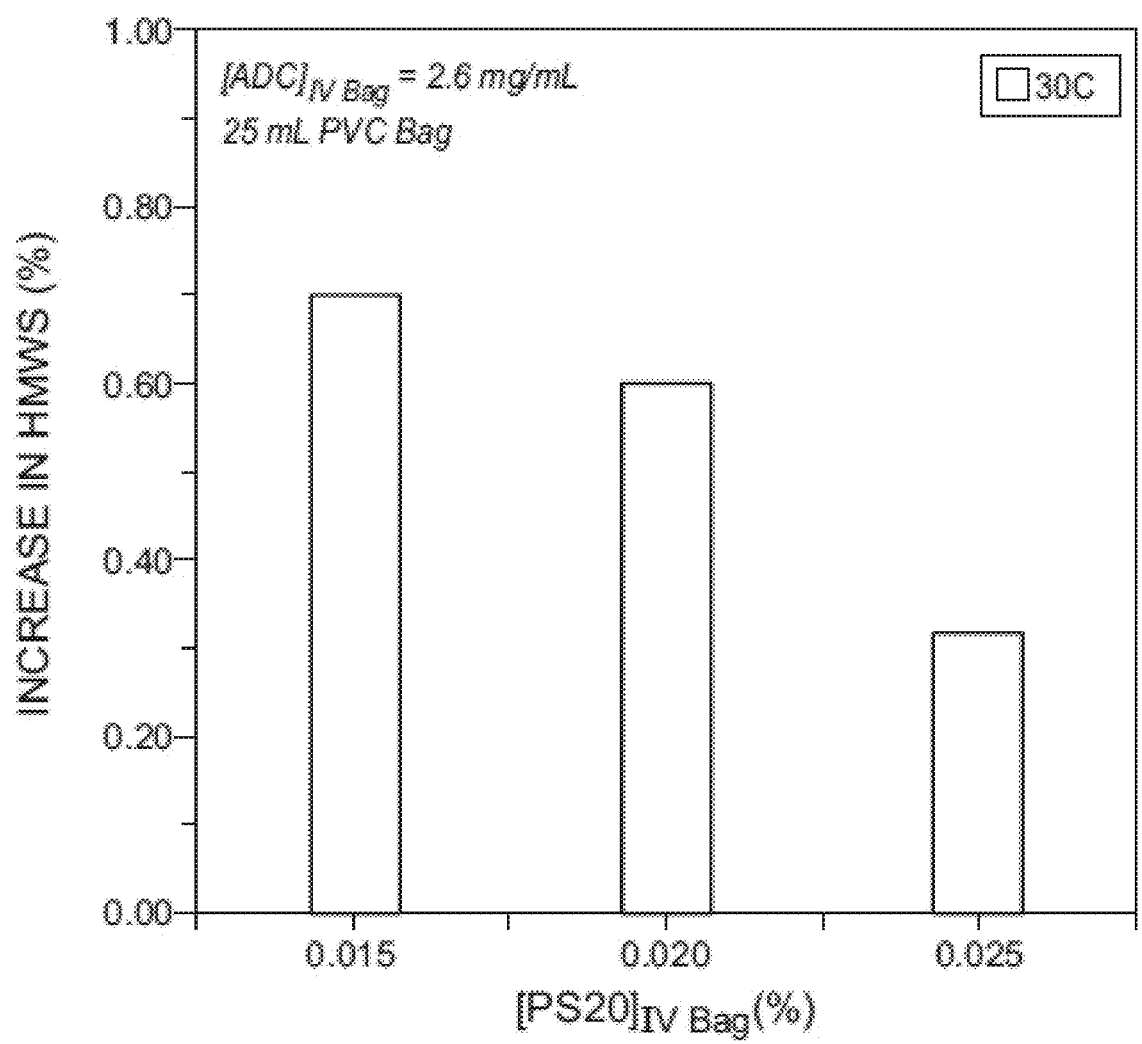
FIG. 5C depicts the effect of 30° C. temperature on stability of anti-CD79b-vc-MMAE upon agitation.

Effect of Temperature on Stability Upon Agitation in IV Bags:

Agitation studies were performed with different levels of PS20 in the bag at 2-8° C., 25° C., and 30° C. (FIG. 5A-FIG. 5C). The rate of increase in HMWS was more at 30° C. than 25° C., which was more than that tested at 2-8° C. The increase in HMWS was correlated to the temperature during agitation in the IV bag. For bags that contain PS20 concentration levels of 0.01%, 0.005% and 0.003% there was no increase in HMWS upon agitation for 2 hours at 2-8° C. (FIG. 5A). At 30° C., the increase in HMWS was dependent on the concentration of PS20 in the bag (FIG. 5C). It was noted that the increase in HMWS upon agitation across all PS20 levels at both 2-8° C. (FIG. 5A) and 25° C. was non-linear (FIG. 5B). This non-linear behavior was likely due to sampling at different time points.

Effect of Surfactant Mixture on Stability Upon Agitation in an IV Bag:

A PS20-P188 hybrid at a 1:1 equal ratio by weight was used to determine if PS20 might prevent SVP formation and P188 might limit the increase in HMWS upon agitation. The study was conducted in 25 mL IV bags using an anti-CD79b-vc-MMAE concentration of 2.6 mg/mL in the bag. On a mass basis, equal amounts of PS20 and P188 were added to yield a total surfactant concentration in the IV bag of either 0.05% or 0.1%.

When 0.05% total surfactant was used in the IV bag, a 2.9% increase in HMWS was observed after agitation at 30° C. for 2 hours (TABLE 2). There was an increasing trend in particles above 5 μm, 10 μm, and 25 μm sizes up to 1 hour and the particle counts were above the limit of detection (LOD) at 2 hours. When 0.1% total surfactant was used in the IV bag, there was an increasing trend in particles across all sizes but was significantly lower than the bag with 0.05% surfactant (TABLE 2). The increase in HMWS was also lower by about 2.8% after 2 hours of agitation compared to 0.05% total surfactant concentration in the IV bag. Based on these results the surfactant hybrid did not show a difference over PS20 alone.

TABLE 2

Hybrid PS20-P188 Surfactant study under Heat Stressed 30° C. Agitation Conditions

| Vol. of Bag (mL) | Temp. (° C.) | Surfactant (%) | Time (hr) | SEC (Relative Area Percent) (%) | | | Conc. (mg/mL) | Turbidity | HIAC (cumulative particles/mL) | | | |
|---|---|---|---|---|---|---|---|---|---|---|---|---|
| | | | | HMWS | Monomer | LMWS | | | 2 μm | 5 μm | 10 μm | 25 μm |
| 25 mL PVC Bag | 30° C. | 0.05% (0.025% PS20 and 0.025% P188) | 0 | 2.2 | 97.6 | 0.2 | NT | 0.02 | 3202 | 383 | 35 | 0 |
| | | | 1 | 3.2 | 96.7 | 0.2 | NT | 0.03 | 3737 | 485 | 48 | 0 |
| | | | 2 | 5.1 | 94.7 | 0.2 | 3.1 | 0.21 | 14666 | 979 | 76 | 0 |
| | | 0.1% (0.05% PS20 and 0.05% P188) | 0 | 1.2 | 98.6 | 0.2 | NT | 0.03 | 3396 | 476 | 53 | 3 |
| | | | 1 | 1.3 | 98.5 | 0.2 | NT | 0.03 | 3973 | 549 | 56 | 0 |
| | | | 2 | 2.3 | 97.5 | 0.2 | 2.7 | 0.03 | 3816 | 650 | 82 | 7 |

Figure 6:
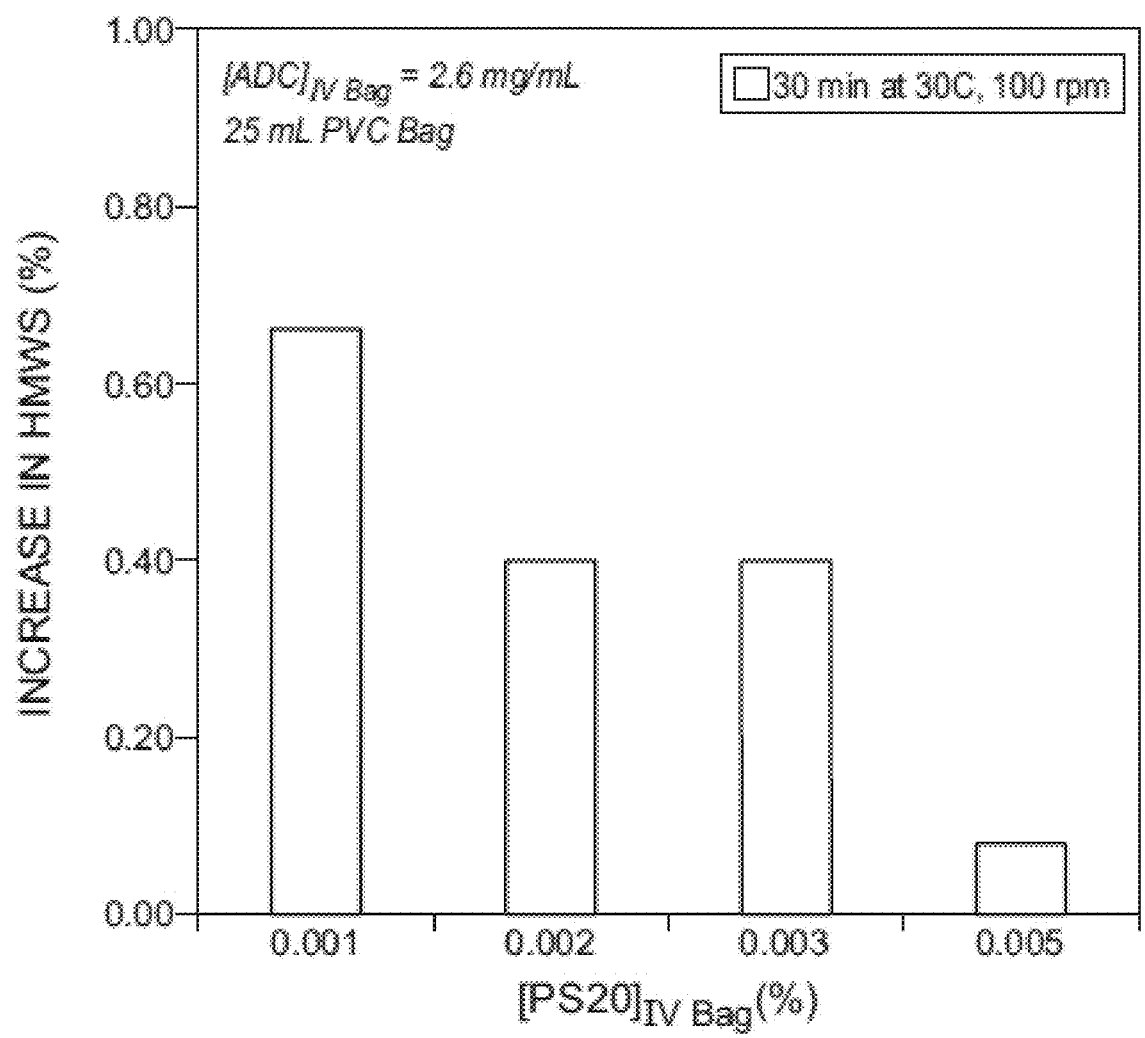
FIG. 6 depicts the physical stability of anti-CD79b-vc-MMAE using Agitation Model 1.

Short Term IV Bag Agitation at 300 C:

The purpose of this study was to investigate transportation of IV bags with diluted anti-CD79b-vc-MMAE for a short term at ambient conditions and to determine the effective concentration of PS20 in the anti-CD79b-vc-MMAAE formulation. This study subjects the bag to short-term agitation at 30° C. for 30 minutes. This shorter agitation at 30° C. could cover potential agitation that a diluted anti-CD79b-vc-MMAE could experience during transportation in a hospital or other facilities at ambient conditions. The study was performed with 0.001%, 0.002%, 0.003% and 0.005% PS20 diluted in the IV bag and agitated at 30° C. at 100 rpm. The results are shown in FIG. 6. Based on the results, there is <0.1% increase with 0.005% PS20 in the bag. Under these conditions, for the anti-CD79b-vc-MMAE, there is a direct correlation of increase in HMWS to the concentration of the PS20 in the IV bag. Based on this study, for physical stability of diluted anti-CD79b-vc-MMAE in the IV bag, the minimum amount of PS20 in the IV bag was between 0.003% and 0.005% to keep the aggregate levels below the limit of quantification.

Figure 7:
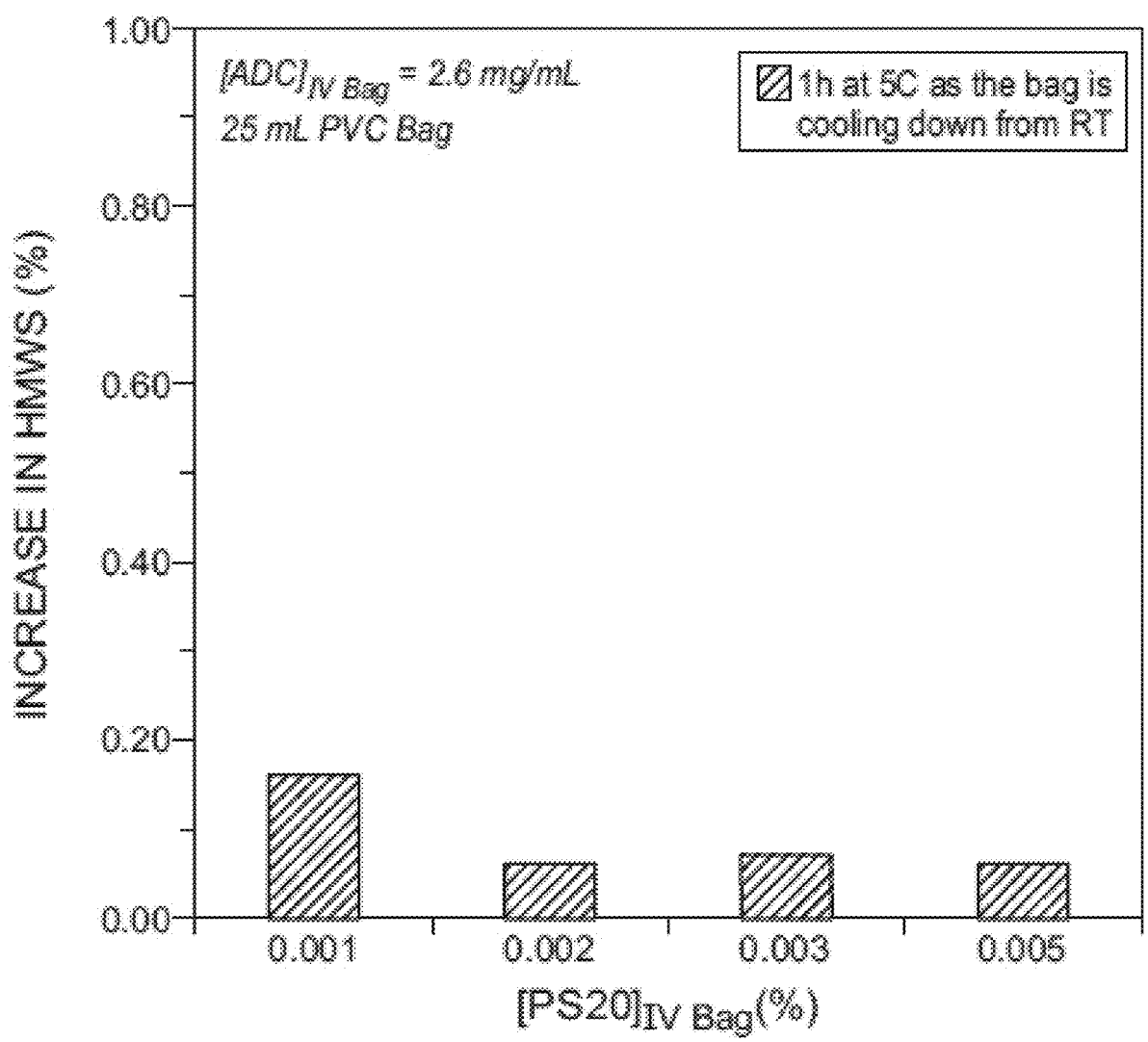
FIG. 7 depicts the physical stability of anti-CD79b-vc-MMAE using Agitation Model 2.

Agitation at 2-8° C. while the IV Bag is Cooling Down (No Pre-Chilling of the Bags):

The purpose of this study was to support transportation of compounded IV bags in a more realistic scenario. Typically, the IV bags are compounded by the pharmacists and are transported in vehicles that might or might not be pre-cooled. Prior to the start of this experiment, the bags are equilibrated to 30° C. to simulate the higher ambient temperatures that may exist in different parts of the world. This assures the stability of diluted DP even if the bags were not precooled or transported in a container that was not pre-cooled. The study was conducted with 2.6 mg/mL of anti-CD79b-vc-MMAE with four different PS20 levels in 100 mL IV bags: 0.001%, 0.002%, 0.003% and 0.005%. There is <0.1% increase in HMWS with <0.002% in the IV bag. Based on the results of this agitation model study, the minimum amount of PS20 in the IV bag was between 0.001% and 0.002% to keep the aggregate levels below the limit of quantification. Results are summarized in FIG. 7.

Conclusions:

Antibody drug conjugates (ADCs) are particularly more sensitive to saline and high ionic strength buffers than regular, unconjugated antibodies (Adem, Y., et al. *Bioconjugate Chemistry*, 25 (2014) 656-664). The anti-CD79b-vc-MMAE tested demonstrated an increase in HMWS when diluted in 0.3% saline at 30° C. for 22 hours under static storage.

Based on the two agitation models, the anti-CD79b-vc-MMAE is stable with at least 0.002% PS20 in the IV bag during agitation caused by short term transportation of 1 hour at 2-8° C. To meet the stability requirements for agitation stress during handling and transportation and short term storage, the final proposed surfactant concentration in the anti-CD79b-vc-MMAE formulation is 0.12%, which results in 0.004% in the bag for the lowest anticipated patient weight (40 kg) when combined with the use of a 100 mL IV bag. This level of surfactant was shown to be protective of the anti-CD79b-vc-MMAE for a dosage range of 1.8 mg/kg to 2.4 mg/kg. It is noted that this amount of surfactant, particularly PS20, is unexpectedly high and counterintuitive in view of the scientific literature, see Kerwin B A. Polysorbates 20 and 80 used in the Formulation of Protein Biotherapeutics: Structure and Degradation Pathways. *Journal of Pharmaceutical Sciences*. 2008; 97(8): 2924-2935. This amount of PS20 used for the anti-CD79b-vc-MMAE drug product is also unexpectedly higher as compared to another immunoconjugate, anti-CD22-vc-MMAE, for which a commercial formulation of 0.05% PS20 was established as suitable for dilution into an IV bag (data not shown).

Example 2: Mitigation of Anti-CD79b Immunoconjugate Oxidation and Linker Hydrolysis Risks Establishing the surfactant concentration suitable for IV bag delivery as discussed in Example 1 potentially added to a problem of oxidation for the anti-CD79b-vc-MMAE. It is known that higher levels of polysorbate are generally associated with higher levels of peroxide due to the autoÖxidative degradation of polysorbate. See Lam X M, Yang J Y, Cleland J L. Antioxidants for prevention of methionine oxidation in recombinant monoclonal antibody HER2. *Journal of Pharmaceutical Sciences*. 1997; 86(11):1250-1255; Donbrow M, Azaz E, Pillersdorf A. Autoxidation of polysorbates. *Journal of Pharmaceutical Sciences*. 1978; 67(12): 1676-1681; Kerwin BA. Polysorbates 20 and 80 used in the Formulation of Protein Biotherapeutics: Structure and Degradation Pathways. *Journal of Pharmaceutical Sciences*. 2008; 97(8):2924-2935.

Further, it is known that tryptophan oxidation can occur in the presence of PS20. See Lam X, et al., Site-Specific Tryptophan Oxidation Induced by Autocatalytic Reaction of Polysorbate 20 in Protein Formulation., *Pharm Res*. (2011) 28:2543-2555. Notably, for the anti-CD79b antibody used in the present disclosure, there is a tryptophan in the variable heavy chain HVR 1: GYTFSSYWIE (SEQ ID NO:4). The propensity to oxidize under AAPH stress conditions (e.g., for up to 2 weeks at 40° C. or 6 months at 25° C. or 6 months at 2-8° C.) was determined by mass spectrometry analysis of tryptic peptides following formulating the anti-CD79b-vc-MMAE with AAPH. The stressed anti-CD79b-vc-MMAE was digested with trypsin and the digested peptides were subjected to LC-MS/MS to determine the percentage of oxidation (data not shown). 68% oxidation of the HVR tryptophan was observed at by peptide mapping. This resulted in approximately a 58% potency loss for the anti-CD79b-vc-MMAE (data not shown). Therefore, it was necessary to mitigate the oxidation risk.

Figure 8:
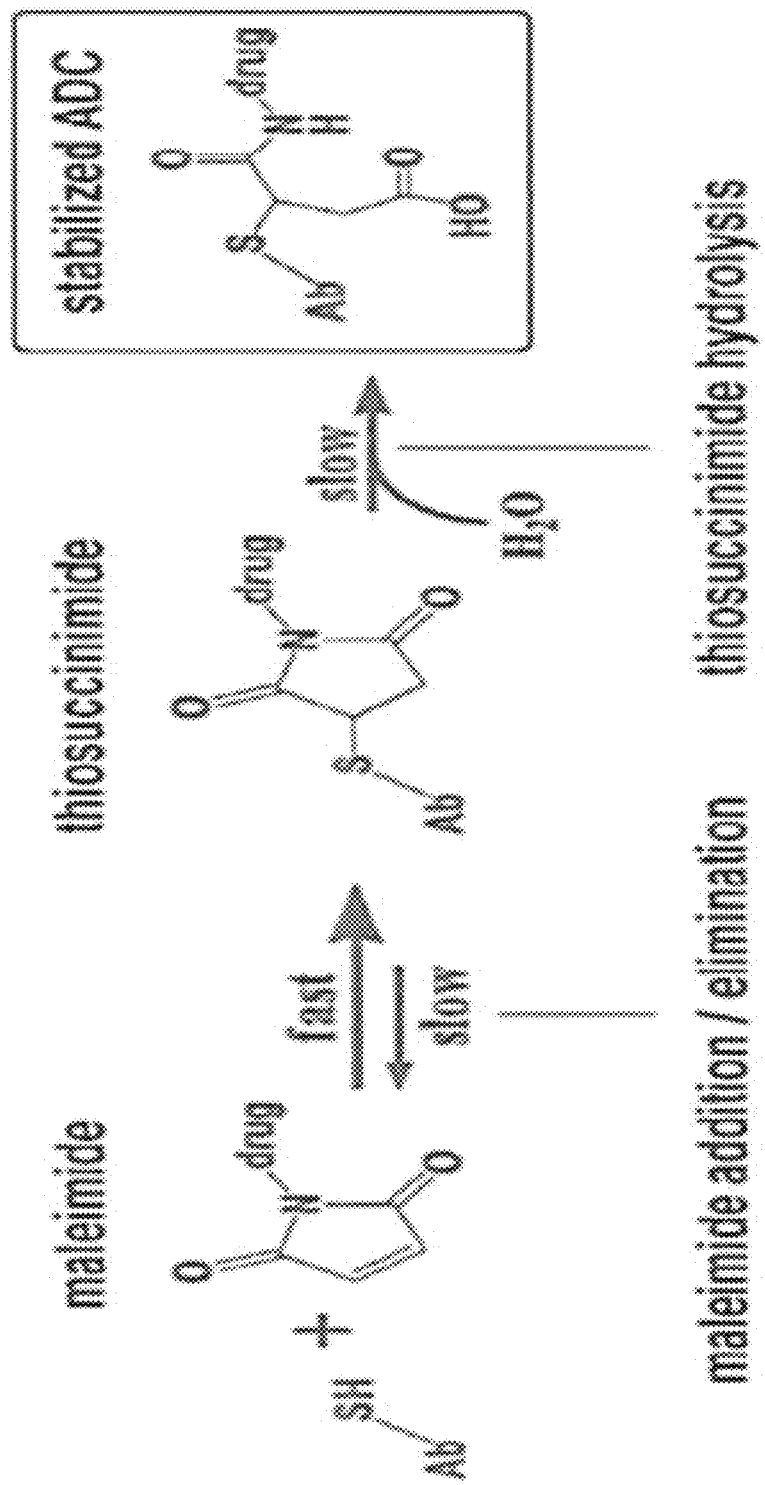
FIG. 8 depicts the hydrolysis reaction of thiosuccinimide to stabilize the immunoconjugate and prevent elimination. Maleimide elimination can be averted by hydrolysis of thiosuccinimide linkages present on an immunoconjugate.

Additional factors to be considered included how to manage succinimide hydrolysis of the immunoconjugate's linker. The present anti-CD79b-vc-MMAE immunoconjugate employed a maleimide-containing drug-linker conjugated to antibody cysteine residues to form thio-succinimide linkages. It is known that such thio-succinimide linkages can undergo two competing reactions while in plasma of a patient: (a) elimination of the maleimide, resulting in an undesirable loss of drug from the immunoconjugate; and (b) hydrolysis of the thio-succinimide ring resulting in a succinic acid derivative which cannot undergo elimination. See FIG. 8 and Lyon, R., et al Self-Stabilizing ADCs: Conjugates Prepared with Maleimido Drug-Linkers that Catalyze their own Thiosuccinimide Ring Hydrolysis., Abstract No. 4333, American Association for Cancer Research (April 2013). This is an important critical quality attribute (CQA) as it has potential impact on pharmacokinetics (pK) and safety. It was previously demonstrated that the initial liquid formulation used for early phase clinical testing in patients, e.g., a liquid formulation in a histidine acetate buffer at a pH of 5.5, demonstrated approximately a 9% increase in acidics at recommended storage conditions over 2 years (data not shown).

As a result of these three risks: increased oxidation risk due to increased PS20 concentrations; increased oxidation risk due to tryptophan oxidation which would result in potency loss; and linker hydrolysis risk which would lead to loss of the MMAE drug from the immunoconjugate and result in free drug in the patient's plasma, a lyophilized formulation was proposed to mitigate these risks to result in a longer, more stable shelf life.

A. Investigation of Alternative Buffer Species:

In order to initiate formulation development for a lyophilized product, an alternative buffer species was investigated. The buffer species used in the early clinical phase formulation, was a histidine acetate buffer. It is known that L-histidine has the potential to oxidize through a wide variety of mechanisms, of which the most common oxidation mechanism observed is photoixidation. See Mason, B., et al Oxidation of Free L-histidine by tert-Butylhydroperoxide., *Pharm Res.* (2010) 27(3):447-456. In addition, acetate can evaporate during the lyophilization process, thereby leading to pH change, which could destabilize the immunoconjugate product. Further, having acetate could be considered a potential hazard for the lyophilization process as acetate is flammable. Therefore, alternative buffer species were evaluated. Three formulations were tested as shown in TABLE 3.

TABLE 3

Buffer Species Screen and pH Range Assessment

| Protein Concentration | Buffer Species | pH |
|---|---|---|
| 22 mg/mL | Histidine/Histidine-HCL | 5.5 |
| 22 mg/mL | Sodium Succinate | 5.0 |
| 22 mg/mL | Sodium Succinate | 6.0 |

The stability of freeze-thawed anti-CD79b-vc-MMAE pharmaceutical compositions in TABLE 3 in disposable PETG containers was assessed in freeze/thaw stress experiments. Protein formulations were sterile filtered and the PETG containers filled. The containers were placed at −20° C. for T=0 and 1 week. The containers were frozen and thawed for a total of five times to room temperature. Only the T=0 and third freeze-thaw cycles were analyzed. The results are summarized in TABLE 4.

TABLE 4

Stability of freeze-thawed anti-CD79b-vc-MMAE
Anti-CD79b-VC-MMAE: 5X Freeze Thaw Study (Large Scale Tox Lot) Summary of Results

| Formulation | Freeze Thaw Cycle (X) | Visible Particulates | CAC | Concentration (mg/mL) | Turbidity (AU) | pH | SEC Peak Area Percent (%) HMWS | Monomer | LMWS | HIAC (Average Cumulative Counts/mL) >2 μm | >5 μm | >10 μm | >25 μm |
|---|---|---|---|---|---|---|---|---|---|---|---|---|---|
| 10 mM His/His-HCL 130 mM Sucrose, 0.06% PS-20, pH 5.5 | 0 | Clear (Liq) | None | 22.3 | 0.09 | 5.57 | 0.6 | 99.2 | 0.2 | 133 | 15 | 3 | 0 |
| | 1 | Clear (Liq) | None | 23.4 | 0.08 | 5.53 | 0.6 | 99.2 | 0.2 | 213 | 68 | 17 | 1 |
| | 2 | Clear (Liq) | None | 23.9 | 0.10 | 5.54 | 0.6 | 99.2 | 0.2 | n.a. | | | |
| | 3 | Clear (Liq) | None | 22.7 | 0.09 | 5.53 | 0.6 | 99.2 | 0.2 | | | | |
| | 4 | Clear (Liq) | None | 23.0 | 0.08 | 5.54 | 0.6 | 99.2 | 0.2 | | | | |
| | 5 | Clear (Liq) | None | 22.7 | 0.08 | 5.55 | 0.6 | 99.2 | 0.2 | 295 | 68 | 22 | 3 |
| 10 mM Na Succinate 130 mM Sucrose, 0.06% PS-20, pH 5.0 | 0 | Clear (Liq) | None | 20.9 | 0.08 | 5.04 | 0.6 | 99.2 | 0.2 | 10 | 2 | 0 | 0 |
| | 1 | Clear (Liq) | None | 20.6 | 0.08 | 5.06 | 0.6 | 99.2 | 0.2 | 57 | 17 | 7 | 1 |
| | 2 | Clear (Liq) | None | 20.6 | 0.08 | 5.04 | 0.6 | 99.2 | 0.2 | n.a. | | | |
| | 3 | Clear (Liq) | None | 21.0 | 0.08 | 5.06 | 0.6 | 99.2 | 0.2 | | | | |
| | 4 | Clear (Liq) | None | 21.3 | 0.08 | 5.04 | 0.6 | 99.2 | 0.2 | | | | |
| | 5 | Clear (Liq) | None | 21.5 | 0.07 | 5.06 | 0.6 | 99.1 | 0.2 | 43 | 10 | 4 | 1 |
| 10 Mm Na Succinate 130 mM Sucrose, 0.06% PS-20, pH 6.0 | 0 | Slightly Opalescent (Liq) | None | 21.0 | 0.10 | 5.99 | 0.7 | 99.1 | 0.2 | 24 | 6 | 3 | 0 |
| | 1 | Slightly Opalescent (Liq) | None | 21.3 | 0.11 | 6.01 | 0.7 | 99.1 | 0.2 | 45 | 24 | 12 | 4 |
| | 2 | Slightly Opalescent (Liq) | None | 21.1 | 0.11 | 6.02 | 0.7 | 99.1 | 0.2 | n.a. | | | |
| | 3 | Slightly Opalescent (Liq) | None | 21.4 | 0.10 | 6.04 | 0.7 | 99.1 | 0.2 | | | | |
| | 4 | Slightly Opalescent (Liq) | None | 20.9 | 0.11 | 6.02 | 0.7 | 99.1 | 0.2 | | | | |
| | 5 | Slightly Opalescent (Liq) | None | 22.1 | 0.10 | 6.03 | 0.7 | 99.1 | 0.2 | 167 | 58 | 23 | 8 |

The results demonstrate that there were no issues observed with any of the three formulations tested Therefore the use of histidine or succinate would be acceptable alternative buffer species to histidine-acetate.

Figure 9:
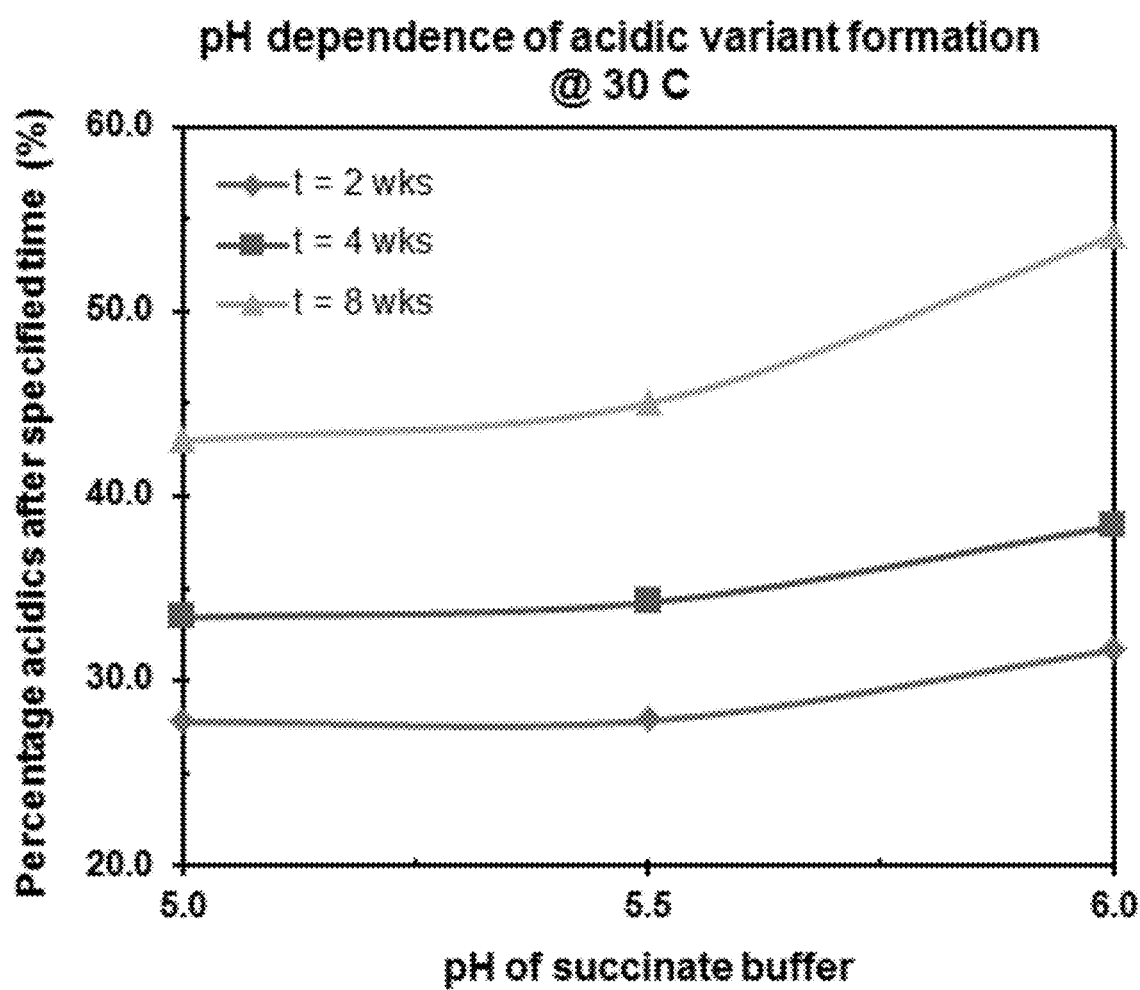
FIG. 9 depicts the effect of pH on Acidic Charge Variant Formation at 30° C. at three different time points: 2 weeks, 4 weeks and 8 weeks.
Figure 10:
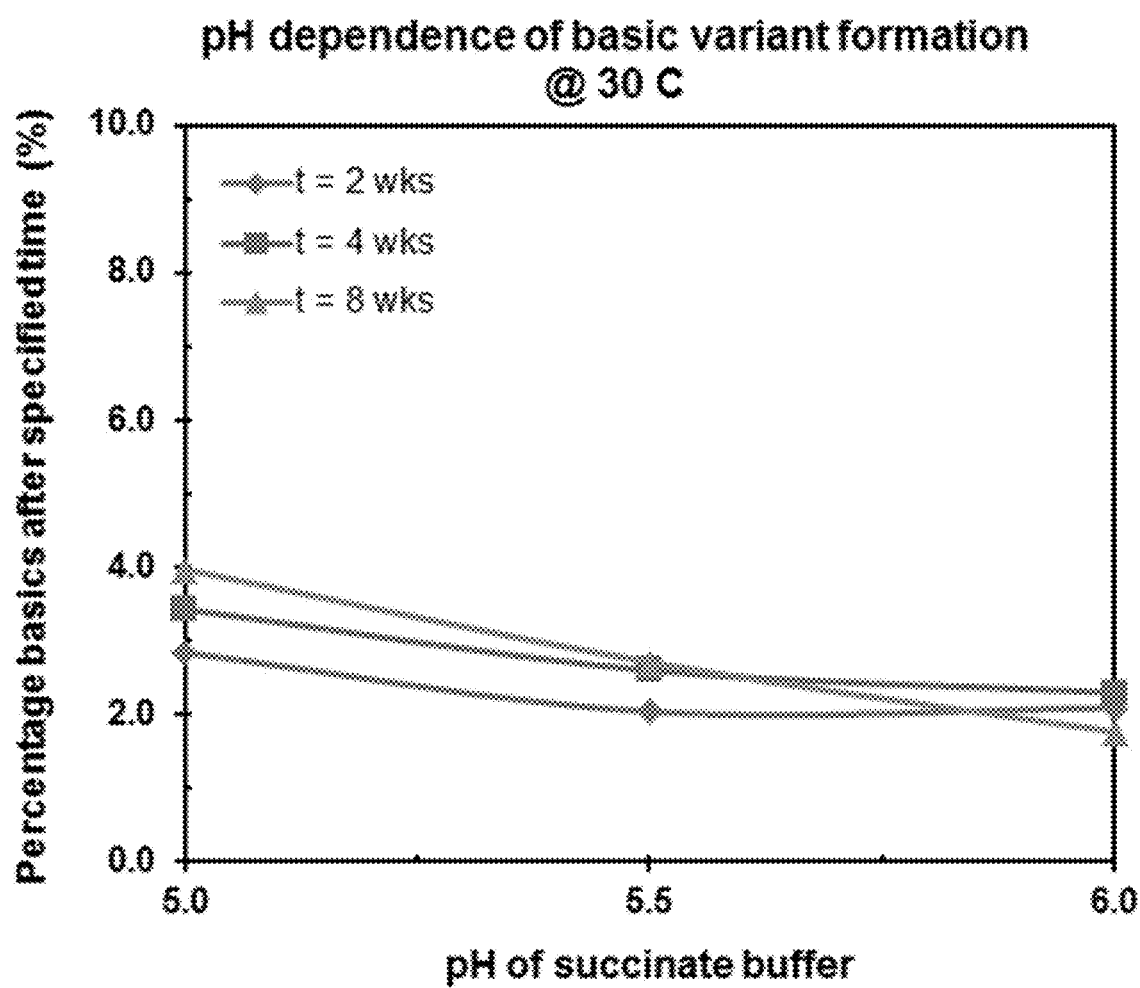
FIG. 10 depicts the effect of pH on Basic Charge Variant Formation at 30° C. at three different time points: 2 weeks, 4 weeks and 8 weeks.

Next stability screens testing the effects of pH on charge variant formation at 30 C was tested. Using the same three liquid formulations as in TABLE 3, which were stressed at 30° C. at three different time points of 2 weeks, 4 weeks and 8 weeks, charge variant distribution was assessed by an iCE280 analyzer (ProteinSimple) with PrinCE microinjector and a fluorocarbon-coated capillary cartridge of 100 μm×5 cm (ProteinSimple). To remove heavy chain C-terminal lysine residue, carboxypeptidase B (CpB) was added to each sample after the dilution step at an enzyme-to-addition of CpB and sialidase A, samples were incubated at 37° C. for 10 minutes. The incubated liquid formulation samples were mixed with the ampholyte solution consisted of a mixture of 700 μL 5-8, 15 μL of pI marker 5.12, 4 μL of pI marker 7.05. The samples were focused by introducing a potential of 1500 V for 1 minute, followed by a potential of 3000V for 5 minutes with the anolyte of 80 mM phosphoric acid, and the catholyte of 100 mM sodium hydroxide, both in 0.1% methyl cellulose. An image of the focused charge variants was obtained by passing 280 nm ultraviolet (UV) light through the capillary and into the lens of a charge-coupled device digital camera. Results are shown in FIG. 9 and FIG. 10 which demonstrated that between pH 5.0 and 5.5, there was less formation of acidic species and slightly faster formation in basic species. Thus, it appears that buffer components do not have a measurable impact on charge stability.

B. Investigation of pH Effects on Stability:

Stability screens testing the effects of pH on size variant formation at 30° C. was tested using the same three liquid formulations as in TABLE 3, which were stressed at 30° C. at three different time points of 2 weeks, 4 weeks and 8 weeks. Size variant distribution was determined by size exclusion chromatography (SEC) on an Agilent Technologies 1200 series HPLC (Santa Clara, Calif.) using a 0.25 mM potassium chloride, pH 6.2 mobile phase. The liquid formulations samples were then loaded onto a Tosoh Bioscience TSKgel G3000SWXL column (South San Francisco, Calif.). The samples were eluted over 30 minutes using a flow rate of 0.5 ml/min and the absorbance was monitored at 280 nm. Results are reported as relative peak area of the total area under the curve and shown in FIG. 11. The stability screen demonstrated that between pH 5.0 and 5.5, fewer high molecular weight species (HMWS) were observed in comparison to pH 6.0. Similar amounts of low molecule weight species (LMWS) were observed after 4 weeks at 30° C. At 8 weeks, slightly higher LMWS at 30° C. were observed. Since decreasing the pH to 5.3 appeared to reduce both charge and size variant formation, a pH 5.3 was selected.

Figure 12:
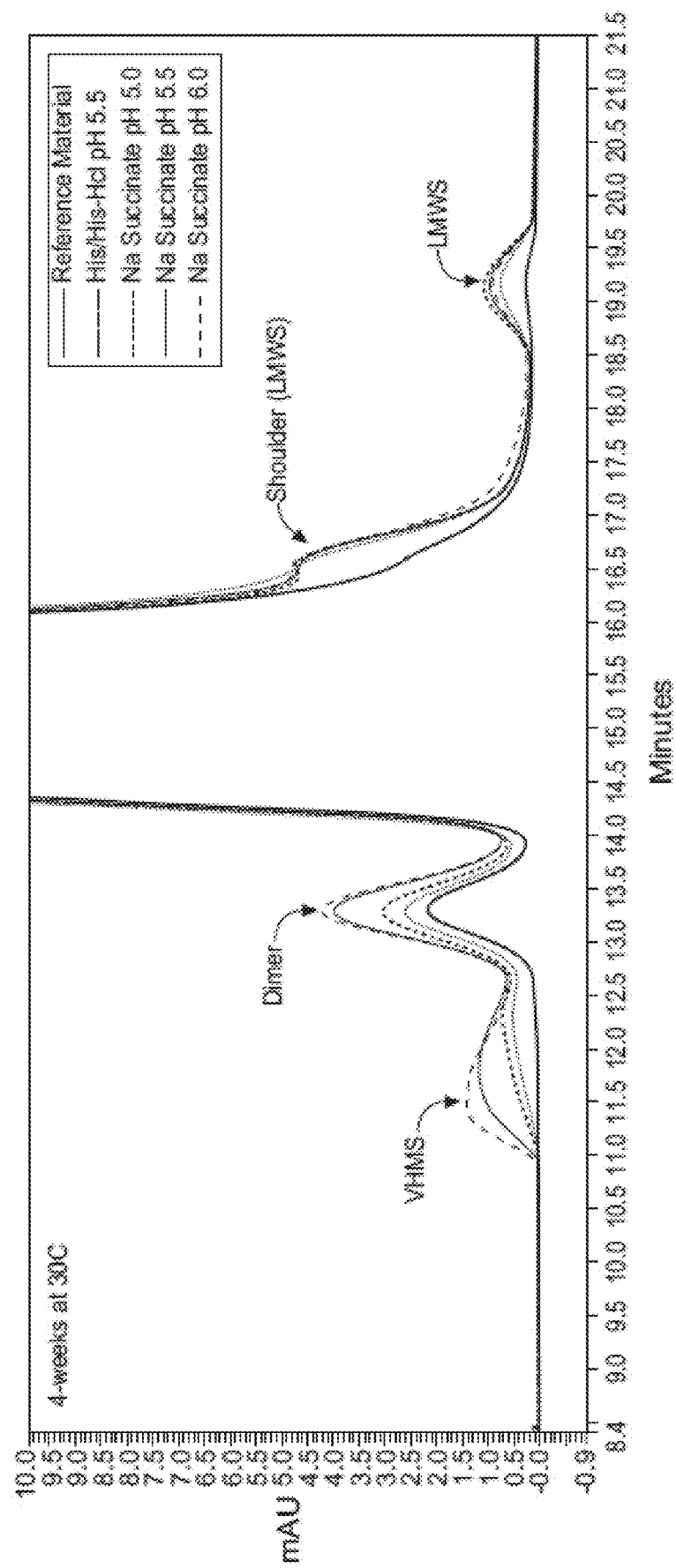
FIG. 12 depicts the effect of pH and buffer species on low molecular weight species (LMWS) stressed at 30° C. for 4 weeks.

FIG. 12 shows a chromatogram testing two buffer species: histidine/histidine-HCl at pH 5.5 compared to sodium succinate at three different pH's: 5.0, 5.5 and 6.0. Histidine buffer at pH 5.5 displayed a slightly better physical stability in liquid at 30° C. than sodium succinate at any pH tested (pH 5.0, 5.5, or 6.0). However, since the sodium succinate buffer displayed an acceptable stability in liquid, and in view of the potential for oxidation risk with histidine, the sodium succinate buffer was selected.

C. Testing Lyophilized Formulations:

A lyophilized formulation was tested to mitigate the risks described above. The general scheme for the lyophilization cycle was as shown in TABLE 5.

TABLE 5

Lyophilization Cycle for anti-CD79b-vc-MMAE

| Step | Description | Temperature (° C.) | Pressure (μm Hg) | Time (HH:MM) |
|---|---|---|---|---|
| 1 | Loading | 5 | N/A | N/A |
| 2 | Hold | 5 | N/A | 1:00 |
| 3 | Freeze Ramp | −35 | N/A | 2:00 |
| 4 | Freeze | −35 | N/A | 6:00 |
| 5 | Evacuation | N/A | 120 | N/A |
| 6 | Primary Drying Ramp | 0 | 120 | 3:00 |
| 7 | Primary Drying | 0 | 120 | 54:00 |
| 8 | Secondary Drying Ramp | 20 | 120 | 2:00 |
| 9 | Secondary Drying | 20 | 120 | 10:00 |

The cycle length was approximately 78 hours or about 3 days. The moisture content was set to be between 0.5% to 0.7%.

A lyophilized screening study was performed testing various anti-CD79b-vc-MMAE concentrations, two different buffer species, different pHs and two different surfactant levels as shown in TABLE 6.

TABLE 6

Lyophilized Screening Study - Test Formulations

| # | Protein Concentration | Buffer | Stabilizer/ Tonicifier | Surfactant | pH |
|---|---|---|---|---|---|
| 1 | 10 mg/ml | 10 mM Na Succinate | 260 mM Sucrose | 0.06% PS20 | 5.0 |
| 2 | 10 mg/ml | 10 mM Na Succinate | 260 mM Sucrose | 0.06% PS20 | 5.5 |
| 3 | 10 mg/ml | 10 mM Na Succinate | 260 mM Sucrose | 0.06% PS20 | 6.0 |
| 4 | 20 mg/ml | 10 mM Na Succinate | 260 mM Sucrose | 0.06% PS20 | 5.5 |
| 5 | 10 mg/ml | 10 mM His/ His-HCl | 260 mM Sucrose | 0.08% PS20 | 5.5 |

These test lyophilized formulations were stored at 30° C. for up to 2 months as part of the screening study.

Figure 13:
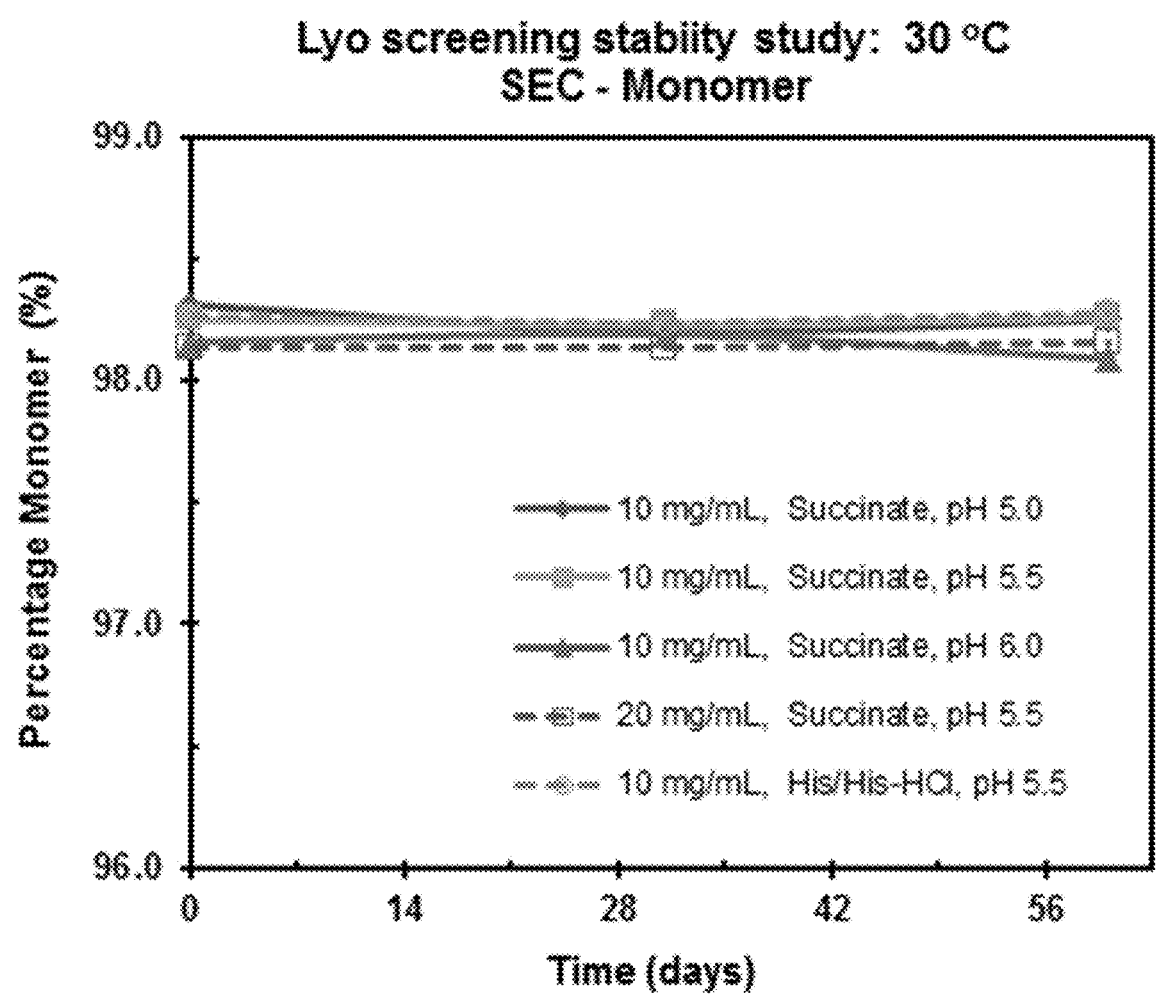
FIG. 13 depicts the stability of lyophilized formulations at 30° C. by size exclusion chromatography (SEC).
Figure 14:
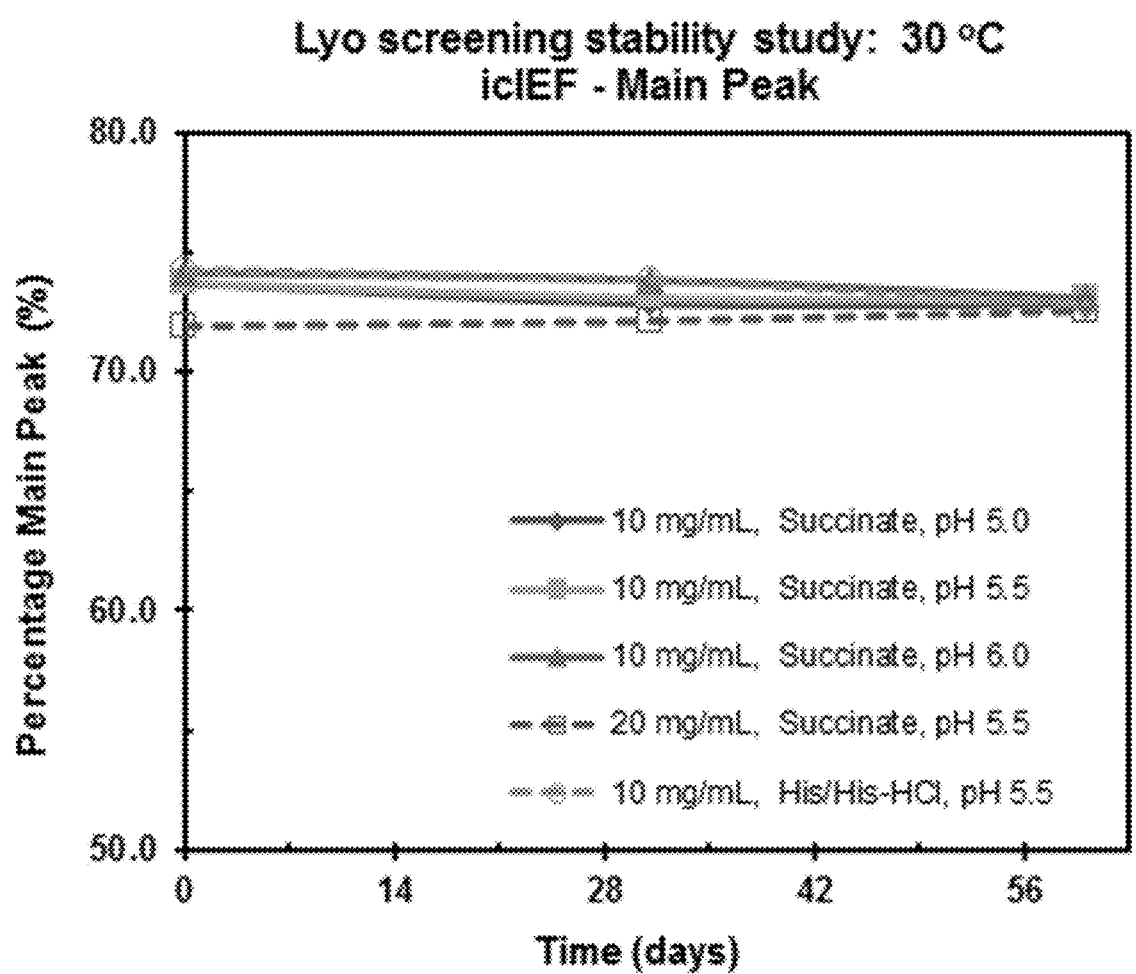
FIG. 14 depicts the stability of lyophilized formulations at 30° C. by imaged capillary isoelectric focusing (icIEF).

To quantitate any monomers developed for each tested formulation (1) to (5) as an indicator for stability, SEC analysis was employed, after reconstitution of each tested formulation to 10 mg/ml or to 20 mg/ml, as described above. FIG. 13 summarizes this study and demonstrates that over the 2 months of heat stress at 30° C., there were no changes in the percent of monomers in any of the formulations tested. Each lyophilized formulation (1) to (5) was also tested by iclEF as described above, to determine the percent main peak after 2 months of heat stress at 30° C. FIG. 14 summarizes this study and demonstrates that over the 2 months of heat stress at 30° C., there were no changes in the percent main peak in any of the formulations tested. As a result of these two studies, it was determined that the sodium succinate buffer over a pH range of 5.0 to 6.0 resulted in acceptable stability for the lyophilized formulations tested.

D. Lyophilized Cake Appearance:

An important aspect of lyophilized formulations is the actual appearance of the lyophilized cake as it is a product quality attribute. For the anti-CD79b-vc-MMAE lyophilized formulation, both the concentration of the immunoconjugate and the concentration of the stabilizer/tonicifier were tested to examine how to improve the appearance of the lyophilized cake. FIG. 15A-FIG. 15C show three lyophilized formulations with different protein to sucrose ratios tested.

Figure 16A:
FIG. 16A-FIG. 16B depict the lyophilized cake appearance with varying protein to sucrose ratios.
Figure 16B:

Indentations were seen in the bottom of the lyophilized cake for all three sucrose levels tested, which does not create an ideal lyophilized cake appearance. Nevertheless, under similar lyophilization conditions, formulations with less sucrose show smaller indentations and lower sucrose concentrations lead to lower moisture. Another lyophilized formulation was tested in which the immunoconjugate concentration was increased to 20 mg/ml while the sucrose concentration was lowered to 120 mM. FIG. 16A and FIG. 16B compares the two lyophilized cake appearances. The 20 mg/ml immunoconjugate concentration with the 120 mM sucrose combination demonstrated the most robust and uniform lyophilized cake appearance. In conducting heat stress stability studies over 4 weeks at 40° C., 25° C. and 5° C., no changes were seen in the cake structure, color or appearance, and the moisture content remained <5%.

Figure 17:
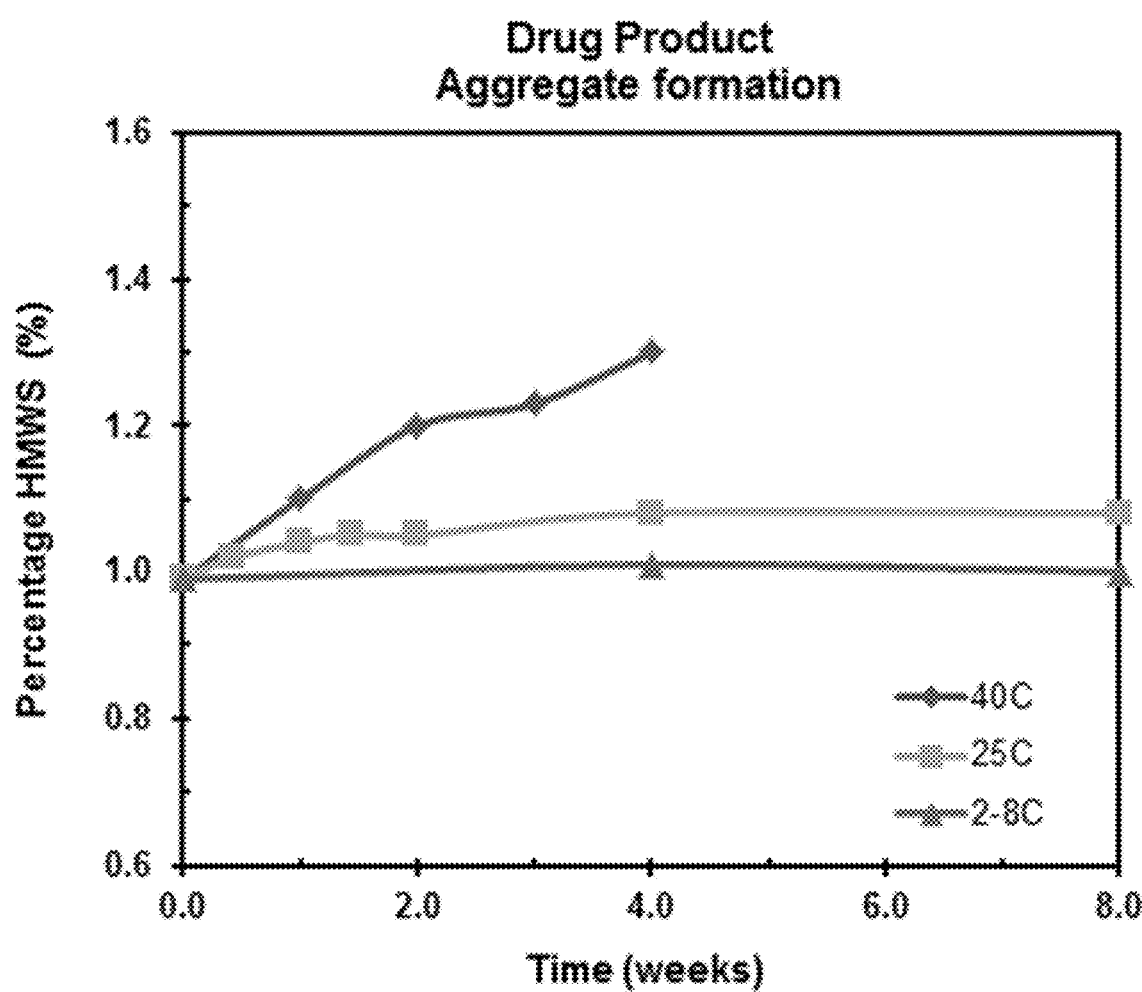
FIG. 17 depicts stability of the lyophilized anti-CD79b-vc-MMAE drug product stressed at 2-8° C., 25° C. and 40° C. to measure HMWS variants by SEC.
Figure 18:
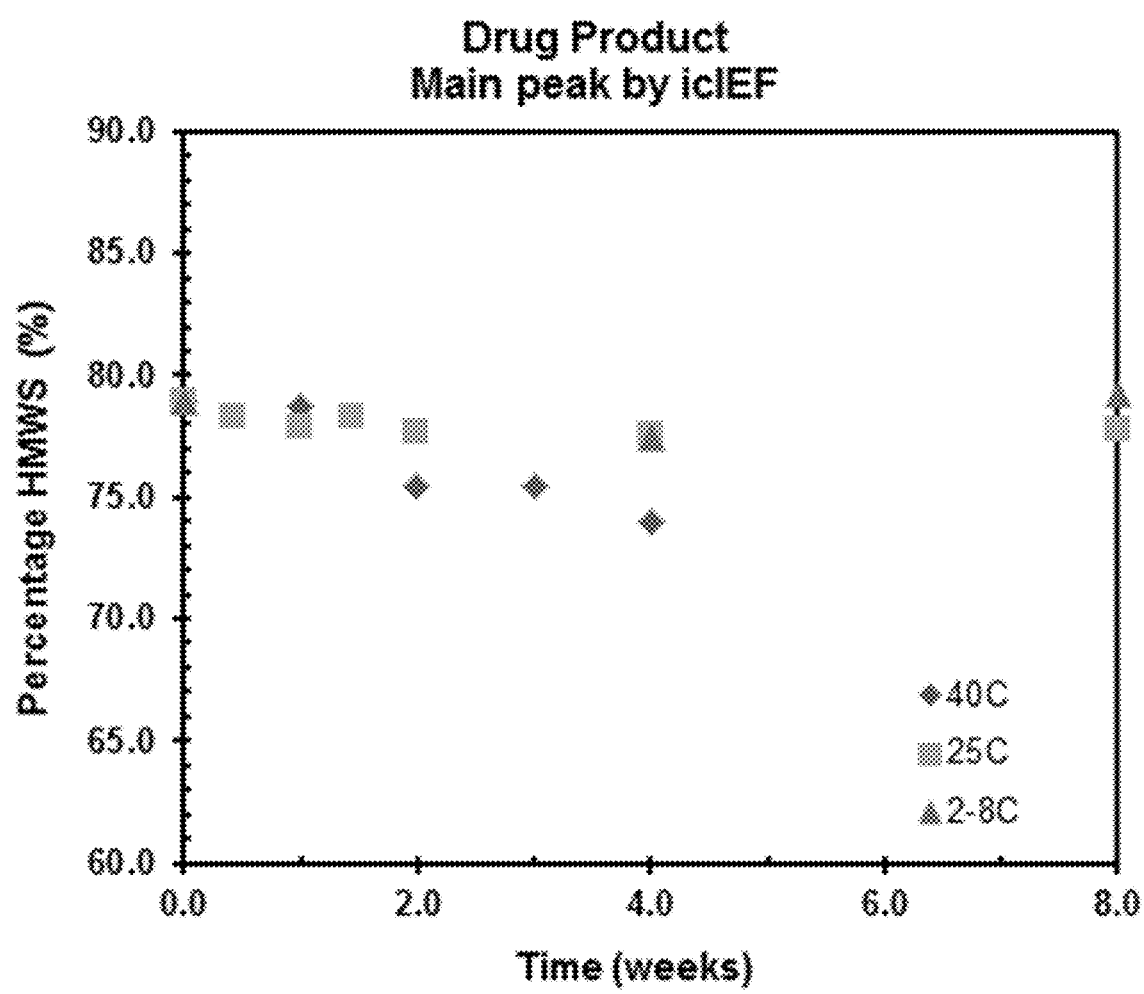
FIG. 18 depicts stability of the lyophilized anti-CD79b-vc-MMAE drug product stressed at 2-8° C., 25° C. and 40° C. to measure HMWS variants by icIEF.

E. Stability of Lyophilized Formulation:

The lyophilized formulation of the drug product: 20 mg/ml anti-CD79b-vc-MMAE, 120 mM sucrose, 0.12% PS20 in 10 mM sodium succinate at pH 5.3 was tested for stability as measured by soluble aggregate or charge variant formation. Soluble aggregates were measured by SEC, as described above. FIG. 17 shows that for the lyophilized drug product, there was less than a 0.1% increase in soluble aggregates at 25° C. and 2-8° C. over 8 weeks. An approximately 0.1% increase in dimer aggregate species per week was observed at 40° C., and the rate of this aggregation may be dependent on moisture level. Charge variants were measured by icIEF, as described above. FIG. 18 shows that for the lyophilized drug product, an approximately 5% loss in main peak and a 3.7% increase in acidics after 4 weeks at 40° C. There were no significant changes measured at 25° C. and 2-8° C. As a result, there were no changes observed for the lyophilized drug product under stressed conditions at 25° C. and 2-8° C.

TABLE 7 summarizes the final anti-CD79b-vc-MMAE formulation arrived at as a result of the many studies described in Examples 1 and 2.

TABLE 7

Summary of final anti-CD79b-vc-MMAE formulation

| | Final Commercial Drug Product Formulation | Rationale |
|---|---|---|
| Dosage Form | Lyophilized, single-use 1:1 reconstitution with SWFI | Minimize succinimide hydrolysis and oxidation risk |
| Formulation | 20 mg/ml Drug Product | Acceptable lyophilized cake appearance |
| | 10 mM sodium succinate | Lyophilization-friendly; minimize oxidation risk |
| | pH 5.3 | Minimize succinimide hydrolysis risk |
| | 120 mM sucrose | Acceptable lyophilized cake appearance |
| | 0.12% PS20 | Enable stability in IV bag |
| Administration Route/Delivery | Intravenous IV bag | Commercial convenience |

As shown TABLE 7 above, the final commercial drug product formulation contains 20 mg/ml Drug Product, which increases the protein-to-drug ratio results in an improved cake appearance when the solution is lyophilized. The 0.12% PS20 (i.e., 1.2 mg/ml) protects the protein in the formulation from interfacial stresses encountered during administration using IV bags and IV infusion sets. The pH of 5.3 minimizes the formation of acidic variants contributed by succinimide hydrolysis. The formulation in Table 7 was designed to deliver 140 mg of drug product per vial after reconstitution in 7.2 mL SWFI to support a clinical dose of 1.8 mg/kg.

Example 3: Evaluating the Robustness of the Anti-CD79b-Vc-MMAE Drug Substance and Drug Product Formulations The drug product (see TABLE 7) in the lyophilized formulation was found to be stable for at least 44 months at 2° C.-8° C. over the residual moisture content range of 0.3% (w/w) to 3.2% (w/w), as well as for at least 7 months at 25° C. over the residual moisture content range of 0.3% (w/w) to 3.2% (w/w).

Next, formulation parameters of the lyophilized drug product were varied and evaluated for practically meaningful impact on the stability of the lyophilized drug product. The five formulation parameters that were tested (and the ranges over which the parameters were varied) were: (a) protein concentration (17-23 mg/ml), (b) succinate concentration (7-23 mM), (c) sucrose concentration (90-150 mM), (d) polysorbate 20 concentration (0.9-1.5 mg/ml), and (e) pH (4.95-5.65). No practically meaningful effect on the stability of lyophilized drug product was observed following storage at 2° C.-8° C. for durations of up to nine months. Based on model-predicted degradation rates, no practically meaningful effect on the stability of lyophilized drug product is expected following storage at 2° C.-8° C. for durations of up to at least 24 months.

Reconstituted drug product solution (i.e., 20 mg/mL polatuzumab vedotin in 10 mM succinate, 120 mM sucrose, 1.2 mg/mL polysorbate 20, at pH 5.3) was found to be physicochemically stable after 72 hours of storage at 2° C.-8° C. or after 24 hours of storage at 30° C. with exposure to ambient light. No significant changes (e.g., statistically significant changes) were detected in the affinity of polatuzumab vedotin for its target (i.e., CD79b) or in the biological activity of polatuzumab vedotin.

Although the present disclosure has been described in some detail by way of illustration and example for purposes of clarity of understanding, the descriptions and examples should not be construed as limiting the scope of the present disclosure. The disclosures of all patent and scientific literature cited herein are expressly incorporated in their entirety by reference.

What is claimed is:

1. A liquid composition comprising an anti-CD79b immunoconjugate, a buffering agent, a sugar, and a surfactant, wherein:
   the anti-CD79b immunoconjugate is at a concentration of about 20 mg/ml;
   the buffering agent is a sodium succinate buffer at a concentration of about 10 mM;
   the sugar is sucrose at a concentration of about 120 mM;
   the surfactant is polysorbate 20 at a concentration of about 0.12% w/v or about 1.2 mg/ml,
   wherein the pH of the liquid composition is about 5.3, and
   wherein the anti-CD79b immunoconjugate comprises the formula:

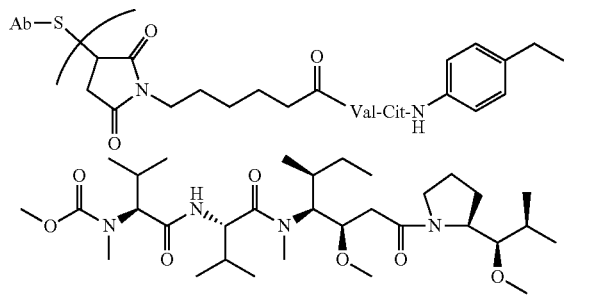

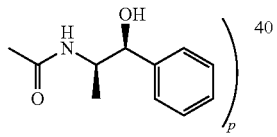

wherein:
   Ab is an anti-CD79b antibody, wherein the anti-CD79b antibody comprises a heavy chain and a light chain, wherein the light chain comprises (a) an HVR-L1 sequence of KASQSVDYEGDSFLN (SEQ ID NO: 1); (b) an HVR-L2 sequence of AASNLES (SEQ ID NO: 2); and (c) an HVR-L3 sequence of QQSNEDPLT (SEQ ID NO: 3); wherein the heavy chain comprises (a) an HVR-H1 sequence of GYTFSSYWIE (SEQ ID NO: 4); (b) an HVR-H2 sequence of GEILPGGGDTNYNEIFKG (SEQ ID NO: 5); and (c) an HVR-H3 sequence of TRRVPIRLDY (SEQ ID NO: 6);
   Val is valine; Cit is citrulline; and
   p is a value from about 1 to about 8.

2. The liquid composition of claim 1, wherein the liquid composition has been reconstituted from a lyophilized composition.

3. A liquid composition for intravenous administration comprising:
   a) between about 0.72 mg/ml and about 2.7 mg/ml of an anti-CD79b immunoconjugate;
   b) between about 0.36 mM and about 1.35 mM sodium succinate;
   c) between about 0.51 mM and about 16.24 mM sucrose; and
   d) between about 0.0432 mg/ml and about 0.162 mg/ml polysorbate 20, wherein the pH of the liquid composition is between about 5 and about 5.7, and wherein the anti-CD79b immunoconjugate comprises the formula:

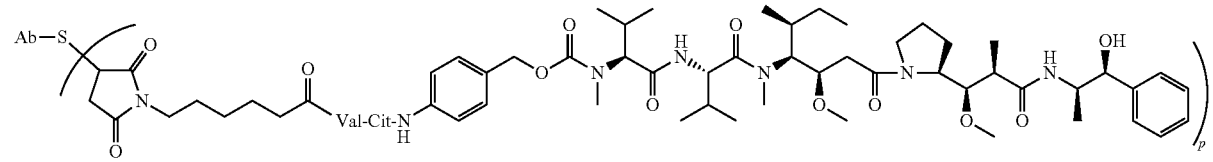

wherein:
Ab is an anti-CD79b antibody, wherein the anti-CD79b antibody comprises a heavy chain and a light chain, wherein the light chain comprises (a) an HVR-L1 sequence of KASQSVDYEGDSFLN (SEQ ID NO: 1);

15. A lyophilized composition comprising about 140-150 mg of an anti-CD79b immunoconjugate, about 8.4-9.0 mg polysorbate 20, about 8.27-8.88 mg succinic acid, about 3.80-4.08 mg sodium hydroxide, and about 288-309 mg sucrose, wherein the anti-CD79b immunoconjugate comprises the formula:

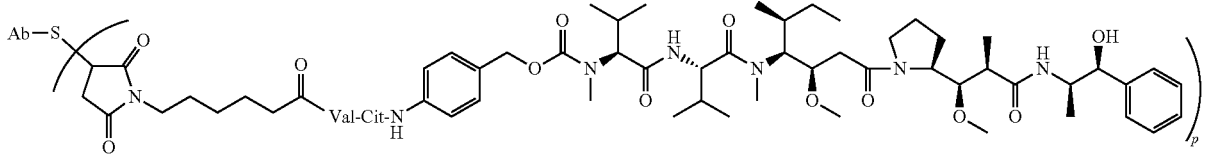

(b) an HVR-L2 sequence of AASNLES (SEQ ID NO: 2); and (c) an HVR-L3 sequence of QQSNEDPLT (SEQ ID NO: 3); wherein the heavy chain comprises (a) an HVR-H1 sequence of GYTFSSYWIE (SEQ ID NO: 4); (b) an HVR-H2 sequence of GEILPGGGDTNYNEIFKG (SEQ ID NO: 5); and (c) an HVR-H3 sequence of TRRVPIRLDY (SEQ ID NO: 6); Val is valine; Cit is citrulline; and
p is a value from about 1 to about 8.

4. The liquid composition of claim 3, comprising:
a) about 0.72 mg/ml of the anti-CD79b immunoconjugate;
b) about 0.36 mM sodium succinate;
c) about 0.51 mM sucrose; and
d) about 0.0432 mg/ml polysorbate 20,
wherein the pH of the liquid composition is between about 5.1 and about 5.4.

5. The liquid composition of claim 3, wherein the liquid composition comprises:
a) about 2.7 mg/ml of the anti-CD79b immunoconjugate;
b) about 1.35 mM sodium succinate;
c) about 16.24 mM sucrose; and
d) about 0.162 mg/ml polysorbate 20,
wherein the pH of the liquid composition is between about 5.1 and about 5.4.

6. The liquid composition of claim 3, wherein the volume of the liquid composition is between about 50 ml and about 100 ml.

7. The liquid composition of claim 6, wherein the volume of the liquid composition is 50 ml.

8. The liquid composition of claim 6, wherein the volume of the liquid composition is 100 ml.

9. The liquid composition of claim 2, wherein the lyophilized composition is a lyophilized cake.

10. The liquid composition of claim 2, wherein the liquid composition has been reconstituted with sterile water for injection (SWFI).

11. The liquid composition of claim 2, wherein the liquid composition has been reconstituted with 7.2 ml sterile water for injection (SWFI).

12. The liquid composition of claim 1, wherein the liquid composition is stable for at least 24 hours upon storage at about 30° C.

13. The liquid composition of claim 1, wherein the liquid composition is stable for at least 72 hours upon storage at about 2° C. to about 8° C.

14. A glass vial containing the liquid composition of claim 1.

wherein:
Ab is an anti-CD79b antibody, wherein the anti-CD79b antibody comprises a heavy chain and a light chain, wherein the light chain comprises (a) an HVR-L1 sequence of KASQSVDYEGDSFLN (SEQ ID NO: 1); (b) an HVR-L2 sequence of AASNLES (SEQ ID NO: 2); and (c) an HVR-L3 sequence of QQSNEDPLT (SEQ ID NO: 3); wherein the heavy chain comprises (a) an HVR-H1 sequence of GYTFSSYWIE (SEQ ID NO: 4); (b) an HVR-H2 sequence of GEILPGGGDTNYNEIFKG (SEQ ID NO: 5); and (c) an HVR-H3 sequence of TRRVPIRLDY (SEQ ID NO: 6); Val is valine; Cit is citrulline; and
p is a value from about 1 to about 8.

16. The lyophilized composition of claim 15, wherein the composition comprises about 150 mg of the anti-CD79b immunoconjugate, about 9.0 mg polysorbate 20, about 8.88 mg succinic acid, about 4.08 mg sodium hydroxide, and about 309 mg sucrose.

17. The lyophilized composition of claim 15, wherein the composition comprises about 140 mg of the anti-CD79b immunoconjugate, about 8.4 mg polysorbate 20, about 8.27 mg succinic acid, about 3.80 mg sodium hydroxide, and about 288 mg sucrose.

18. The lyophilized composition of claim 15, wherein the lyophilized composition is stable for at least 6 months upon storage at about 2° C. to about 8° C.

19. The lyophilized composition of claim 15, wherein the lyophilized composition is stable for at least 7 months upon storage at about 25° C. over a residual moisture content range of 0.3% (w/w) to 3.2% (w/w).

20. The lyophilized composition of claim 15, wherein the composition is a lyophilized cake.

21. A liquid composition produced by reconstituting the lyophilized composition of claim 15.

22. A glass vial containing the lyophilized composition of claim 15.

23. A liquid composition for intravenous administration obtained by diluting the liquid composition of claim 1 in an isotonic buffer.

24. The liquid composition of claim 23, wherein the isotonic buffer is a 0.9% sodium chloride solution, a 0.45% sodium chloride solution, or a 5% dextrose solution.

25. The liquid composition of claim 23, wherein the surfactant concentration following dilution is at least 0.004% w/v.

26. The liquid composition of claim 3, wherein the liquid composition is in an intravenous (IV) bag.

27. An intravenous (IV) bag containing the liquid composition of claim 3.

28. The liquid composition of claim 1, wherein the anti-CD79b antibody comprises a heavy chain variable domain (VH) comprising the amino acid sequence of SEQ ID NO: 7 and a light chain variable domain (VL) comprising the amino acid sequence of SEQ ID NO: 8.

29. The liquid composition of claim 1, wherein the heavy chain of the anti-CD79b antibody comprises the amino acid sequence of SEQ ID NO: 9, and wherein the light chain of the anti-CD79b antibody comprises the amino acid sequence of SEQ ID NO: 10.

30. The liquid composition of claim 1, wherein p is a value from about 2 to about 5.

31. The liquid composition of claim 1, wherein p is about 3.5.

32. The liquid composition of claim 1, wherein the anti-CD79b immunoconjugate is polatuzumab vedotin.

* * * * *

SEQUENCE LISTING

<160> NUMBER OF SEQ ID NOS: 18

<210> SEQ ID NO 1
<211> LENGTH: 15
<212> TYPE: PRT

<210> SEQ ID NO 1
<211> LENGTH: 16
<212> TYPE: PRT
<213> ORGANISM: Artificial Sequence
<220> FEATURE:
<223> OTHER INFORMATION: Synthetic Construct

<400> SEQUENCE: 1

Lys Ala Ser Gln Ser Val Asp Tyr Glu Gly Asp Ser Phe Leu Asn
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2

Ala Ala Ser Asn Leu Glu Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic Construct

<400> SEQUENCE: 3

Gln Gln Ser Asn Glu Asp Pro Leu Thr
1               5

<210> SEQ ID NO 4
<211> LENGTH: 10
<212> TYPE: PRT
<213> ORGANISM: Artificial Sequence
<220> FEATURE:
<223> OTHER INFORMATION: Synthetic Construct

<400> SEQUENCE: 4

Gly Tyr Thr Phe Ser Ser Tyr Trp Ile Glu
1               5                   10

<210> SEQ ID NO 5
<211> LENGTH: 18
<212> TYPE: PRT
<213> ORGANISM: Artificial Sequence
<220> FEATURE:
<223> OTHER INFORMATION: Synthetic Construct

<400> SEQUENCE: 5

Gly Glu Ile Leu Pro Gly Gly Gly Asp Thr Asn Tyr Asn Glu Ile Phe
1               5                   10                  15

Lys Gly

<210> SEQ ID NO 6
<211> LENGTH: 10
<212> TYPE: PRT
<213> ORGANISM: Artificial Sequence
<220> FEATURE:
<223> OTHER INFORMATION: Synthetic Construct

<400> SEQUENCE: 6

Thr Arg Arg Val Pro Ile Arg Leu Asp Tyr
1               5                   10

<210> SEQ ID NO 7
<211> LENGTH: 117

```
<212> TYPE: PRT
<213> ORGANISM: Artificial Sequence
<220> FEATURE:
<223> OTHER INFORMATION: Synthetic Construct

<400> SEQUENCE: 7
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
            20                  25                  30

Trp Ile Glu Trp Val Arg Gln Ala Pro Gly Lys Gly Leu Glu Trp Ile
        35                  40                  45

Gly Glu Ile Leu Pro Gly Gly Asp Thr Asn Tyr Asn Glu Ile Phe
    50                  55                  60

Lys Gly Arg Ala Thr Phe Ser Ala Asp Thr Ser Lys Asn Thr Ala Tyr
65              70                  75                  80

Leu Gln Met Asn Ser Leu Arg Ala Glu Asp Thr Ala Val Tyr Tyr Cys
                85                  90                  95

Thr Arg Arg Val Pro Ile Arg Leu Asp Tyr Trp Gly Gln Gly Thr Leu
            100                 105                 110

Val Thr Val Ser Ser
            115

```
<210> SEQ ID NO 8
<211> LENGTH: 112
<212> TYPE: PRT
<213> ORGANISM: Artificial Sequence
<220> FEATURE:
<223> OTHER INFORMATION: Synthetic Construct

<400> SEQUENCE: 8
```

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Glu
            20                  25                  30

Gly Asp Ser Phe Leu Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
50                  55                  60

Arg Phe Ser Gly Ser Gly Ser Gly Thr Asp Phe Thr Leu Thr Ile Ser
65              70                  75                  80

Ser Leu Gln Pro Glu Asp Phe Ala Thr Tyr Tyr Cys Gln Gln Ser Asn
                85                  90                  95

Glu Asp Pro Leu Thr Phe Gly Gln Gly Thr Lys Val Glu Ile Lys Arg
            100                 105                 110

```
<210> SEQ ID NO 9
<211> LENGTH: 446
<212> TYPE: PRT
<213> ORGANISM: Artificial Sequence
<220> FEATURE:
<223> OTHER INFORMATION: Synthetic Construct

<400> SEQUENCE: 9
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
            20                  25                  30

Trp Ile Glu Trp Val Arg Gln Ala Pro Gly Lys Gly Leu Glu Trp Ile 35                  40                  45
Gly Glu Ile Leu Pro Gly Gly Asp Thr Asn Tyr Asn Glu Ile Phe
 50                  55                  60

Lys Gly Arg Ala Thr Phe Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Thr Arg Arg Val Pro Ile Arg Leu Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 10

<211> LENGTH: 218
<212> TYPE: PRT
<213> ORGANISM: Artificial Sequence
<220> FEATURE:
<223> OTHER INFORMATION: Synthetic Construct

<400> SEQUENCE: 10

```
Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Glu
            20                  25                  30

Gly Asp Ser Phe Leu Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Leu Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 11
<211> LENGTH: 25
<212> TYPE: PRT
<213> ORGANISM: Artificial Sequence
<220> FEATURE:
<223> OTHER INFORMATION: Synthetic Construct

<400> SEQUENCE: 11

```
Glu Val Gln Leu Val Glu Ser Gly Gly Gly Leu Val Gln Pro Gly Gly
1               5                   10                  15

Ser Leu Arg Leu Ser Cys Ala Ala Ser
            20                  25
```

<210> SEQ ID NO 12
<211> LENGTH: 13
<212> TYPE: PRT
<213> ORGANISM: Artificial Sequence
<220> FEATURE:
<223> OTHER INFORMATION: Synthetic Construct

<400> SEQUENCE: 12

```
Trp Val Arg Gln Ala Pro Gly Lys Gly Leu Glu Trp Val
1               5                   10
```

<210> SEQ ID NO 13
<211> LENGTH: 11
<212> TYPE: PRT
<213> ORGANISM: Artificial Sequence
<220> FEATURE:
<223> OTHER INFORMATION: Synthetic Construct

<400> SEQUENCE: 13

Trp Gly Gln Gly Thr Leu Val Thr Val Ser Ser
1               5                   10

<210> SEQ ID NO 14
<211> LENGTH: 23
<212> TYPE: PRT
<213> ORGANISM: Artificial Sequence
<220> FEATURE:
<223> OTHER INFORMATION: Synthetic Construct

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 15
<211> LENGTH: 15
<212> TYPE: PRT
<213> ORGANISM: Artificial Sequence
<220> FEATURE:
<223> OTHER INFORMATION: Synthetic Construct

<400> SEQUENCE: 15

Trp Tyr Gln Gln Lys Pro Gly Lys Ala Pro Lys Leu Leu Ile Tyr
1               5                   10                  15

<210> SEQ ID NO 16
<211> LENGTH: 11
<212> TYPE: PRT
<213> ORGANISM: Artificial Sequence
<220> FEATURE:
<223> OTHER INFORMATION: Synthetic Construct

<400> SEQUENCE: 16

Phe Gly Gln Gly Thr Lys Val Glu Ile Lys Arg
1               5                   10

<210> SEQ ID NO 17
<211> LENGTH: 32
<212> TYPE: PRT
<213> ORGANISM: Artificial Sequence
<220> FEATURE:
<223> OTHER INFORMATION: Synthetic Construct

<400> SEQUENCE: 17

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 18
<211> LENGTH: 30
<212> TYPE: PRT
<213> ORGANISM: Artificial Sequence
<220> FEATURE:
<223> OTHER INFORMATION: Synthetic Construct

```
<400> SEQUENCE: 18

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30
```